(12) United States Patent
Debs et al.

(10) Patent No.: US 6,627,615 B1
(45) Date of Patent: *Sep. 30, 2003

(54) METHODS AND COMPOSITIONS FOR IN VIVO GENE THERAPY

(75) Inventors: Robert J. Debs, Mill Valley, CA (US); Ning Zhu, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/132,391

(22) Filed: Aug. 11, 1998

Related U.S. Application Data

(63) Continuation of application No. 08/464,899, filed as application No. PCT/US93/05366 on Jun. 4, 1993, which is a continuation-in-part of application No. 07/992,687, filed on Dec. 17, 1992, now abandoned, which is a continuation-in-part of application No. 07/927,200, filed on Aug. 6, 1992, now abandoned, which is a continuation-in-part of application No. 07/894,498, filed on Jun. 4, 1992, now abandoned, which is a continuation-in-part of application No. 08/256,004, filed as application No. PCT/US92/11004 on Dec. 17, 1992, now Pat. No. 6,001,644, which is a continuation-in-part of application No. 07/972,135, filed on Nov. 5, 1992, now Pat. No. 5,858,784, which is a continuation-in-part of application No. 07/809,291, filed on Dec. 17, 1991, now abandoned, which is a continuation-in-part of application No. 07/927,200, filed on Aug. 6, 1992, now abandoned, which is a continuation-in-part of application No. 07/894,498, filed on Jun. 4, 1992, now abandoned.

(51) Int. Cl.$^7$ .............................................. C12N 16/54

(52) U.S. Cl. .................... 514/44; 424/417; 424/420; 424/450; 435/325; 435/354; 435/375; 435/458; 435/6; 435/69.1

(58) Field of Search ........................ 435/69.1, 172.3, 435/240.2, 325, 354, 375, 6, 458; 514/44; 424/450, 417, 420

(56) References Cited

U.S. PATENT DOCUMENTS

| | | | |
|---|---|---|---|
| 3,826,255 A | 7/1974 | Havstad et al. | 128/194 |
| 4,046,146 A | 9/1977 | Rosskamp et al. | 128/266 |
| 4,253,468 A | 3/1981 | Lehmbeck | 128/726 |
| 4,268,460 A | 5/1981 | Boiarski et al. | 261/1 |
| 4,394,448 A | 7/1983 | Szoka | 435/172.3 |
| 4,510,929 A | 4/1985 | Bordoni et al. | 128/200.14 |
| 4,649,911 A | 3/1987 | Knight et al. | 128/200.4 |
| 4,804,678 A | 2/1989 | Augstein et al. | 514/456 |
| 4,946,787 A | 8/1990 | Eppstein | 435/240.2 |
| 5,032,407 A | 7/1991 | Wagner | 424/520 |
| 5,075,229 A | 12/1991 | Hanson | 435/172.3 |
| 5,240,842 A | 8/1993 | Mets | 435/172.3 |
| 5,240,846 A | 8/1993 | Collins | 435/240.1 |
| 5,264,618 A | 11/1993 | Felgner | 560/224 |
| 5,676,954 A | 10/1997 | Brigham | 424/450 |
| 5,756,353 A | 5/1998 | Debs | 435/375 |
| 5,827,703 A | * 10/1998 | Debs et al. | 435/172.3 |

FOREIGN PATENT DOCUMENTS

| | | | |
|---|---|---|---|
| DE | 3545126 A | 6/1987 | |
| EP | 0 281 246 A2 | 9/1988 | |
| EP | 0 469 632 A1 | 2/1992 | |
| GB | 354126 | 8/1931 | |
| WO | 89/02469 | 3/1989 | |
| WO | 89/12109 | 12/1989 | |
| WO | 90/06997 | 6/1990 | |
| WO | WO/90/10448 | 9/1990 | |
| WO | 90/11092 | 10/1990 | |
| WO | 90/12878 | 11/1990 | |
| WO | WO 91/02796 | 3/1991 | ........... C12N/15/12 |
| WO | 91/06309 | 5/1991 | |
| WO | WO 91/06309 | 5/1991 | ........... A61K/37/22 |
| WO | WO 91/17773 | 11/1991 | ........... A61K/47/48 |
| WO | WO 92/05252 | 4/1992 | ........... C12N/15/12 |
| WO | WO/93/04701 | 3/1993 | |
| WO | WO/93/12240 | 6/1993 | |
| WO | WO 93/24640 | 12/1993 | |

OTHER PUBLICATIONS

S. Crooke, Basic Principles of Antisense Therapeutics, Springer–Verlag, Eds. 1998:1–50.*
H. James, The Therapeutic Potential of Ribozymes, 1998; Blood/vol. 9 No. 2:371–382.*
Good et. al. ; Gene Therapy 1997; vol. 4: 45–54.*
Rossi, Controlled, targeted, intracellular expression of ribozmes: progress and problems; 1995, Tibtech, vol. 13:301–306.*
A. Branch, A good antisense molecule is hard to find; 1998; Trend in Biochemical Sciences vol. 23:45–50.*
Dzau, Victor J., et al. (1993) "Gene therapy for cardiovascular disease", *TIBTECH* 11:205–210.
Friedmann, Theodore (1989) "Progress Toward Human Gene Therapy", *Science* 244:1275–1281.
Zhu, Ning, et al., (1993) "Systemic Gene Expression After Intravenous DNA Delivery into Adult Mice", *Science*, 261:209–211.
Rosenfeld, et al. (1992) "In vivo Transfer of the Human Cystic Fibrosis Transmembrane Conductance Regulator Gene to the Airway Epithelium", *Cell*, 68:143–155.
Brigham, et al. (1989) "Expression of a Prokaryotic Gene in Cultured Lung Endothelial Cells after Lipofection with a Plasmid Vector", *Am. J. Respir. Cell. Mol. Biol.*, 1:95–100.

(List continued on next page.)

Primary Examiner—James Ketter
Assistant Examiner—Richard Schnizer
(74) Attorney, Agent, or Firm—Townsend and Townsend and Crew LLP

(57) ABSTRACT

Novel methods and compositions are provided for introducing a gene capable of modulating the genotype and phenotype into two or more tissues following systemic administration. The gene can be introduced into a mammalian host by way of an expression vector either as naked DNA or associated with lipid carriers, particularly cationic lipid carriers. Multiple individual tisssues can be transfected using naked DNA. Using a DNA: lipid carrier complex. multiple tissues and cell types can be transfected. The techniques and compositions find use in the palliation or treatment of any of a variety of genetic-based disorders.

38 Claims, 69 Drawing Sheets

OTHER PUBLICATIONS

Alton, E. et al. (1993) "Non–invasive liposome–mediated gene delivery can correct the ion transport defect in cystic fibrosis mutant mice", *Nature Genetics*, 5:135–142.

Huang, et al. (1990) "The Simian Virus 40 Small–t Intron, Present in Mamy Common Expression Vectors, Leads to Aberrant Splicing", *Molecular and Cellular Biology*, 10(4):1805–1810.

Matteucci, et al., "Synthesis of Deoxyoligonucleotides of a Polymer Support," *J. Am. Chem. Soc.*, vol. 103:3185–3191 (1981).

Volloch, et al., "Stability of Globin mRNA in Terminally Differentiating Murine Erythroleukemia Cells," *Cell* vol. 23:509–514 (1981).

Bothwell, et al., "Heavy Chain Variable Region Contribution to the NP Family of Antibodies: Somatic Mutation Evident in a γa Variable Region," *Cell*, vol. 24:625–637 (1981).

Edge, et al., "Total Synthesis of a Human Leukocyte Interferon Gene," *Nature*, vol. 292:756–762 (1981).

Schaefer–Ridder, et al., "Liposomes as Gene Carriers: Efficient Transformation of Mouse L Cells by Thymidine Kinase Gene," *Science*, vol. 215:166–168 (1981).

Gorman, et al., "Recombinant Genomes which Express Chloramphenicol Acetyltransferase in Mammalian Cells," *Molecular and Cellular Biology*, vol. 2 No. 9:1044–1051 (1982).

Gorman, et al., "The Rous Sarcoma Virus Long Terminal Repeat is a Strong Promoter when Introduced into a Variety of Eukaryotic Cells by DNA–Mediated Transfection," *PNAS (USA)*, vol. 79:6777–6781 (1982).

Long, et al., "Complete Sequence of the cDNA for Human α–Antitrypsin and the Gene for the S. Variant," *Biochemistry*, vol. 23:4828–4837 (1984).

Nambair, et al., "Total Synthesis and Cloning of a Gene Coding for the Ribonuclease S. Protein," *Science*, vol. 223:1299–1301 (1984).

Jay, et al., "Chemical Synthesis of a Biologically Active Gene for Human Immune Interferon–γ," *Journal of Biological Chemistry*, vol. 259, No. 10:6311–6317 (1984).

Kunkel, Thomas, "Rapid and Efficient Site–specific Mutagenesis without Phenotypic Selection," *PNAS (USA)*, vol. 82:488–492 (1985).

Boshart, et al., "A Very Strong Enhancer is Located Upstream of an Immediate Early Gene of Human Cytomegalovirus," *Cell*, vol. 41:521–530 (1985).

Papahadjopoulos et al., "Cochleate Lipid Cylinders: Formation by Fusion of Unilamellar Lipid Vesicles," *Biochimica et Biophysica Acta*, vol. 394:483–491 (1975).

Deamer et al., "Large Volume Liposomes by an Ether Vaporization Method," *Biochimica et Biophysica Acta*, vol. 443:629–634 (1976).

Ostro, et al., "Incorporation of High Molecular Weight RNA into Large Artificial Lipid Vesicles," *Biochemical and Biophysical Research Communications*, vol. 76, No. 3:836–842 (1977).

Enoch, et al., "Formation and Properties of 1000–A–Diameter, Single–Bilayer Phospholipid Vesicles," *PNAS (USA)*, vol. 76, No. 1:145–149 (1979).

Wilson, et al., "The Introduction of Poliovirus RNA into Cells via Lipid Vesicles (Liposomes)," *Cell*, vol. 17:77–84 (1979).

Fraley, et al., "Entrapment of a Bacterial Plasmid in Phospholipid Vesicles: Potential for Gene Transfer," *PNAS (USA)*, vol. 76, No. 7:3348–3352 (1979).

Huang, et al., "Monoclonal Antibody Covalently Coupled with Fatty Acid," *Journal of Biological Chemistry*, vol. 255, No. 17:8015–8018 (1980).

Fraley, et al., "Introduction of Liposome–Encapsulated SV40 DNA into Cells," *Journal of Biological Chemistry*, vol. 255 No. 21:10431–10435 (1980).

Leserman, et al., "Targeting to Cells of Flourescent Liposomes Covalently Coupled with Monoclonal Antibody of Protein A," *Nature*, vol. 288:602–604 (1980).

Beaucage, et al., "Deoxynucleoside Phosphoramidites—A New Class of Key Intermediates for Deoxypolynucleotide Synthesis," *Tetrahedron Letters*, vol. 22 No. 20:1859–1862 (1981).

Duckworth et al., "Rapid Synthesis of Oligodeoxyribonucleotides VI. Efficient, Mechanised Synthesis of Heptadecadeoxyribonucleotides by an Improved Solid Phase Phosphotriester Route," *Nucleic Acids Research*, vol. 9 No. 7:1691–1706 (1981).

Martin, et al., "Immunospecific Targeting of Liposomes to Cells: A Novel and Efficient Method for Covalent Attachment of Fab' Fragments via Disulfide Bonds," *Biochemistry*, vol. 20:4229–4238 (1981).

Stinski, et al., "Activation of the Major Immediate Early Gene of Human Cytomegalovirus by cis–Acting Elements in the Promoter–Regulatory Sequence and by Virus–specific Trans–acting Components," *Journal of Virology*, vol. 55 No. 2:431–441 (1985).

Cullen, B.R., "Trans–Activation of Human Immunodeficiency Virus Occurs via a Bimodal Mechanism," *Cell*, vol. 46:973–982 (1986).

Benvenisty, et al., "Direct Introduction of Genes into Rats and Expression of the Genes," *PNAS (USA)*, vol. 83:9551–9555 (1986).

Debs, et al., "Successful Treatmen with Aerosolized Pentamidine of Pneumocystis Carinii Pneumonia in Rats," *Antimicrobial Agents and Chemotherapy*, vol. 31 No. 1:37–41 (1987).

Montgomery, et al., "Aerosolised Pentamidine as Sole Therapy for Pneumocystis Carinii Pneumonia in Patients with Acquired Immunodeficiency Syndrome," *Lancet*, vol. 11:480–483 (1987).

Felgner, et al., "Lipofection: A Highly Efficient, Lipid–Mediated DNA–Transfection Procedure," *PNAS (USA)*, vol. 84:7413–7417 (1987).

Wang, et al., "pH Sensitive Immunoliposomes Mediate Target–Cell–Specific Delivery and Controlled Expression of a Foreign Gene in a Mouse," *PNAS (USA)*, vol. 84:7851–7855 (1987).

Mannino, et al., "Liposome Mediated Gene Transfer," *Biotechniques*, vol. 6 No. 7:682–690 (1988).

Sakai, et al., "Hormone–Mediated Repression: A Negative Clucocorticoid Response Element from the Bovine Prolactin Gene," *Genes and Development*, vol. 2:1144–1154 (1988).

Stamatatos, et al., "Interactions for Cationic Lipid Vesicles with Negatively Charged Phospholipid Vesicles and Biological Membranes," *Biochemistry*, vol. 27:3917–3925 (1988).

Debs, et al., "Lung–Specific Delivery of Cytokines Induces Sustained Pulmonary and Systemic Immunomodulation in Rats," *J. Immunology*, vol. 140 No. 10:3482–3488 (1988).

Wu, et al., "Receptor–Mediated Gene Delivery and Expression In Vivo," *J. Biological Chemistry*, vol. 263, No. 29:14621–14624 (1988).

Hubbard, et al., "Fate of Aerosolized Recombinant DNA–Produced α1 –Antitrypsin: Use of the Epithelial Surface of the Lower Respiratory Tract to Administer Proteins of Therapeutic Importance," *PNAS (USA)* vol. 86:680–684.

Kaneda, et al., "Increased Expression of DNA Cointroduced with Nuclear Protein in Adult Rat Liver," *Science*, vol. 243:375–378 (1989).

Malone, et al., "Cationic Liposome–Mediated RNA Transfection," *PNAS (USA)*, vol. 86:6077–6081 (1989).

Rommens, et al., "Identification of the Cystic Fibrosis Gene: Chromosome Walking and Jumping," *Science*, vol. 245:1059–1065 (1989).

Goodfellow, P.N., "Steady Steps Lead to the Gene," *Nature*, vol. 341:102–103 (1988).

Mizuno, et al., "In Vitro and In Vivo Expressionof Human Interferon–γ in Glioma Cells Transfected with its Gene Encapsulated in Liposomes," *J. Interferon Research*, vol. 9, Supp. 2:S151 (Abstract A1–8) (1989).

Huang, et al., "Intervening Sequences Increase Efficiency of RNA 3' Processing and Accumulation of Cytoplasmic RNA," *Nucleic Acids Research*, vol. 18 No. 4:937–947 (1990).

Ono, et al., "Plasmid DNAs Directly Injected into Mouse Brain with Lipofectin Can Be Incorporated and Expressed by Brain Cells," *Neuroscience Letters*, vol. 117:259–263 (1990).

Holt, et al., "Lipofectin of cDNAs in the Embryonic Vertebrate Central Nervous System," *Neuron*, vol. 4:203–214 (1990).

Uhlmann, et al., "Antisense Oligonucleotides: A New Therapeutic Principles," *Chemical Reviews*, vol. 90 No. 4:543–584 (1990).

Debs, et al., "Regulation of Gene Expression In Vivo by Liposome–Mediated Delivery of a Purified Transcription Factor," *J. Biological Chemistry*, vol. 265 No. 18:10189–10192 (1990).

R.G. Crystal, "α1–Antitrypsin transcript Deficiency, Emphysema, and Liver Disease", *The Journal of Clinical Investigation, Inc.*, 85:1343–1352 (5/90).

Ann–Bin Shyu et al., "The c–fos transcript is targeted for rapid decay by two distinct mRNA degradation pathways," *Genes & Development*, 3:60–72 (1989).

Rosenberg et al., "Gene Transfer into Human—Immunotherapy of Patients with Advanced Melanoma, Using Tumor–Infiltrating Lymphocytes Modified by Retroviral Gene Transduction", *The New England Journal of Medicine*, vol. 323, 9:570–578 (1990).

Burhans et al., "Identification of an Origin of Bidirectional DNA Replication in Mammalian Chromosomes", *Cell*, 62:955–965 (1990).

Nabel, et al., "Site–Specific Gene Expression In Vivo by Direct Gene Transfer into the Arterial Wall", *Science*, 249:1285–1288 (1990).

Verma, "Gene Therapy Treatment of Disease by Introducing Healthy Genes into the Body is Becoming Feasible. But the Therapy will not reach its full potential until the genes can be coaxed to work throughout life", *Scientific American*, pp. 68–84 (1990).

Barr, et al., "Expression of Recominant Genes in Myocardium In Vivo Follwoing Direct Injection of DNA", *Clinical Research*, 39:2:152A (1991).

Kitsis, et al., "Behaviour of Genes Directly Transferred to Rat Heart In Vivo", *Clinical Research*, vol. 39, 2:152A (1991).

Hazinski, et al., "Localization and Induced Expression of Fusion Genes in the Rat Lung", *Am. J. Resp. Cell. Molec. Biol.*, 4:206–209 (1991).

Hug, et al., "Lipsomes for the Transformation of Eukaryotic Cells", *Biochemica et Biophysica Acta*, 1097:1–17 (1991).

Palmiter et al., Heterologous Introns can Enhance Expression of Transgenes in Mice, *PNAS (USA)*, 88:478–482 (1991).

Felgner, et al., "Gene Therapeutics", *Nature*, 349:351–352 (1991).

Weatherall, "Gene Therapy Perspective", *Nature*, 349:275–276 (1991).

Fleischman, "Southwestern Internal Medicine Conference: Human Gene Therapy", *The American Journal of the Medical Sciences*, vol. 301, 5:353–363 (1991).

Kitsis, et al., "Hormonal Modulation of a Gene Injected into Rat Heart In Vivo", *PNAS (USA)*, 88:4138–4142 (1991).

Choi, et al., "A Generic Intron Increases Gene Expression in Transgenic Mice", *Molecular and Cellular Biology*, vol. 11, 6:3070–3074 (1991).

Lim, et al., "Direct In Vivo Gene Transfer into the Coronary and Peripheral Vasculatures of the Intact Dog", *Circulation*, vol. 83, 6:2007–2011 (1991).

Wu, et al., "Receptor–Mediated Gene Delivery In Vivo", *Journal of Biological Chemistry*, vol. 266, 22:14338–14342 (1991).

Acsadi, et al., "Human Dystrophin Expression in mdx Mice after Intramuscular Injection of DNA Constructs", *Nature*, 352:815–818 (1991).

Rosenberg, "Immunotherapy and Gene Therapy of Cancer", *Cancer Research (Suppl.)*, vol. 51, 18:5074S–5079S (1991).

Stone, R. Ed., "FDA Ponders Gene–Therapy Regulations", *Sciencescope*, p. 1575 (1991).

Anderson, "Human Gene Therapy", *Science*, 256:808–813 (1992).

Collins, "Cystic Fibrosis: Molecular Biology and Therapeutic Implications", *Science*, 256:774–783 (1992).

Cox, et al., "Emphysema of Early Onset Associated with a Complete Deficiency of Alpha–1–Antitrypsin (null homozygotes)[1–3]", *Am. Rev. Respir. Dis.*, 137:371–375 (1988).

Gilbert, "Sequencing End–Labeled DNA with Base–Specific Chemical Cleavages", *Methods in Enzymology*, 65:499–560 (1980).

Wright, "A New Nebuliser", *Lancet*, 2:24–25 (1958).

Mercer, et al., "Operating Characteristics of Some Compressed–Air Nebulizers", *Am. Ind. Hyg. Assoc. J.*, 29:66–78 (1968).

Raabe, "Particles Size Analysis Utilizing Grouped Data and the Log–Normal Distribution", *J. Aerosol Sci.*, 2:289–303 (1971).

Szoka, et al., "Procedure for preparation of liposomes with large internal aqueous space and high capture by reverse–phase evaporation", *PNAS (USA)*, vol. 75, 9:4194–4198 (1978).

Mercer, "Production of Therapeutic Aerosols, Principles and Techniques", *Chest*, vol. 80, Supp. 6:813–817 (1981).

Straubinger et al., "Liposomes as Carriers for Intracellular Delivery of Nucleic Acids", *Methods of Enzymology*, 101:512–527 (1983).

Gregoriadis, "Liposomes for drugs and vaccines", *Trends in Biotechnology*, vol. 3, 9:235–241 (1985).

Dobbs, "An improved method for isolating Type II cells in High Yield and Purity", *Amer. Rev. Respiratory Disease*, 134:141–145 (1986).

Debs, et al., "Selective enhancement of Pentamidine uptake in the lung by aerosolization and delivery in liposomes," *Amer. Rev. Respiratory Disease*, 135:731–737 (1986).

Lai, et al., "The essential role of microsomal deacetylase activity in the metabolic activation, DNA–(deoxyguanosin–8–yl)–2–aminofluorene adduct formation and initiation of liver tumors by N–hydroxy–2–acetylaminoflurorene in the livers of infant male B6C3F$_1$ mice", *Carcinogenesis*, 9:1295–1302 (1988).

Beardsley, et al., "Winning Candidate: A painstaking search identifies the gene for cystic fibrosis", *Sci. Am.*, 261:28–30 (1989).

Brigham, et al., "Rapid communication: in vivo transfection of murine lungs with a functioning prokaryotic gene using a liposome vehicle", *Am. J. Med. Sci.*, 298:278–281 (1989).

Montgomery, et al., "Aerosolized Pentamidine as second line therapy in patients with AIDS and *pneumocystis carinii* pneumonia", *Chest*, 95:747–751 (1989).

Debs, et al., "Biodistribution, tissue reaction and lung retention of Pentamidine aerosolized as three different salts," *Am. Rev. Respir. Dis.*, 142:1164–1167 (1990).

Leoung, et al., "Aerosolized Pentamidine for prophylaxis against *Pneumocystis carinii* pneumonia" *N. Eng. J. Med.*, 323:769–775 (1990).

Treat, et al., "Antitumor activity of liposome–encapsulated doxorubicin in advanced breast cancer: Phase II study", *J. Natl. Cancer Instit.*, 82:1706 (1990).

Rasmussen, "*Listeria monocytogenes* can be clasified into two major types according to the sequence of the listeriolysin gene", *Infect. and Immun.*, vol. 59, 11:3945–3951 (1991).

Canonico, et al., "Expression of a CMV promoter driven human α–1 antitrypsin gene in cultured lung endothelial cells and in the lungs of rabbits", *Clinical Research*, 39:219A (1991).

Holden, "Animal rights vet wins a round", *Science*, 253:964–965 (1991).

Marino, et al., "Localization of the Cystic Fibrosis Transmembrane Conductance Regulator in Pancreas", *J. Clin. Invest.*, 88:712–716 (1991).

\* cited by examiner

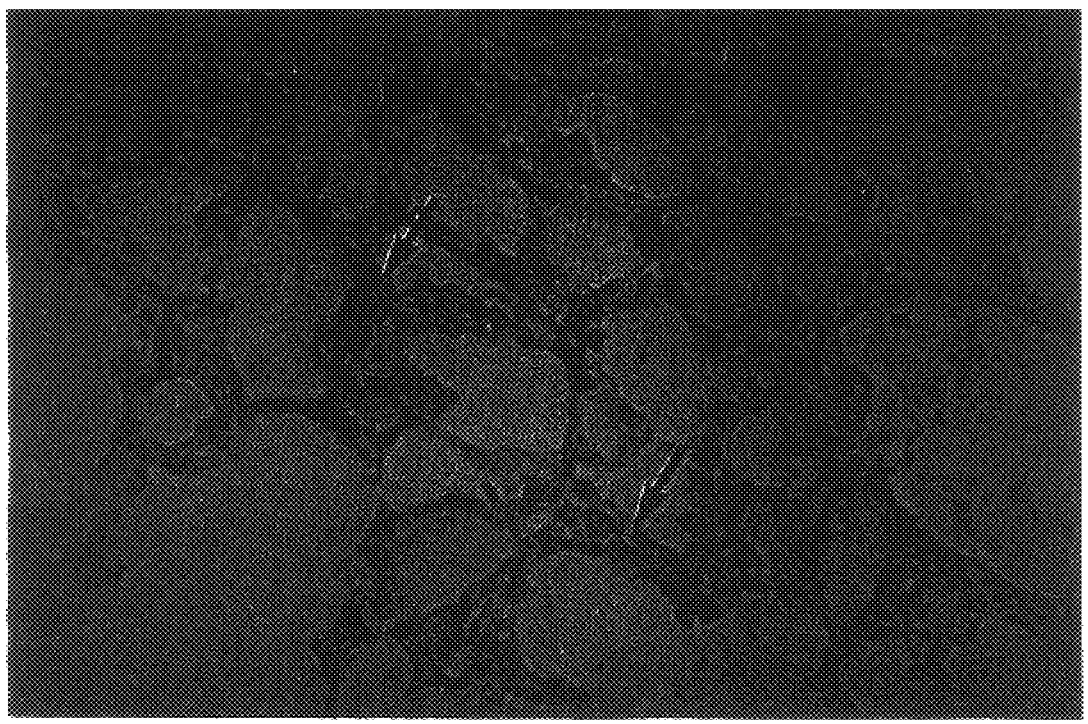
FIGURE 1A
FIGURE 1B          Control

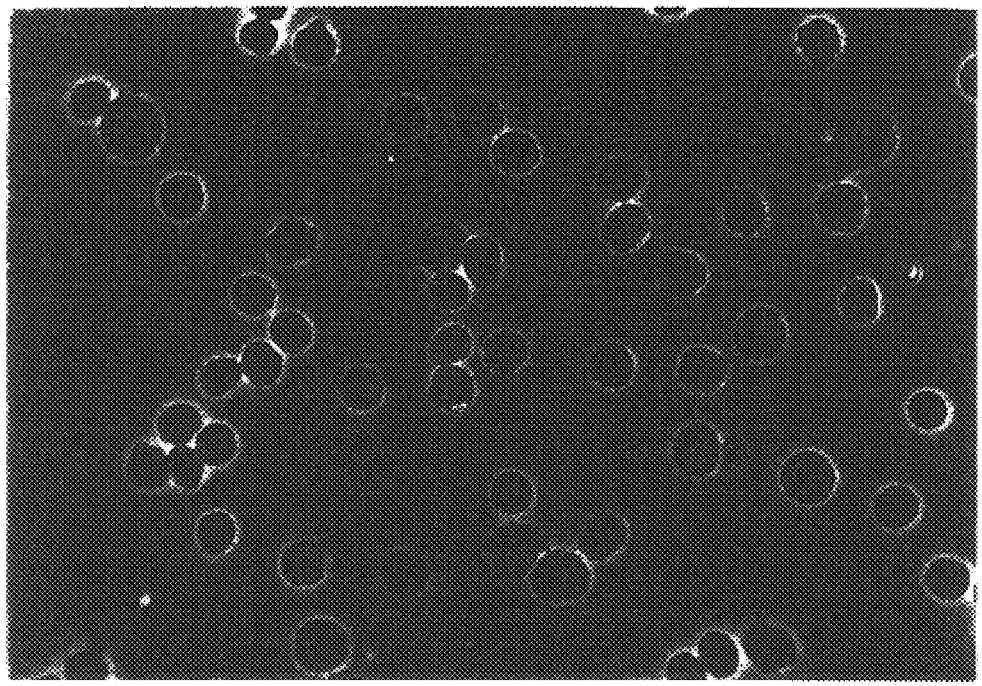
Phase Contrast　　　FIGURE 2A
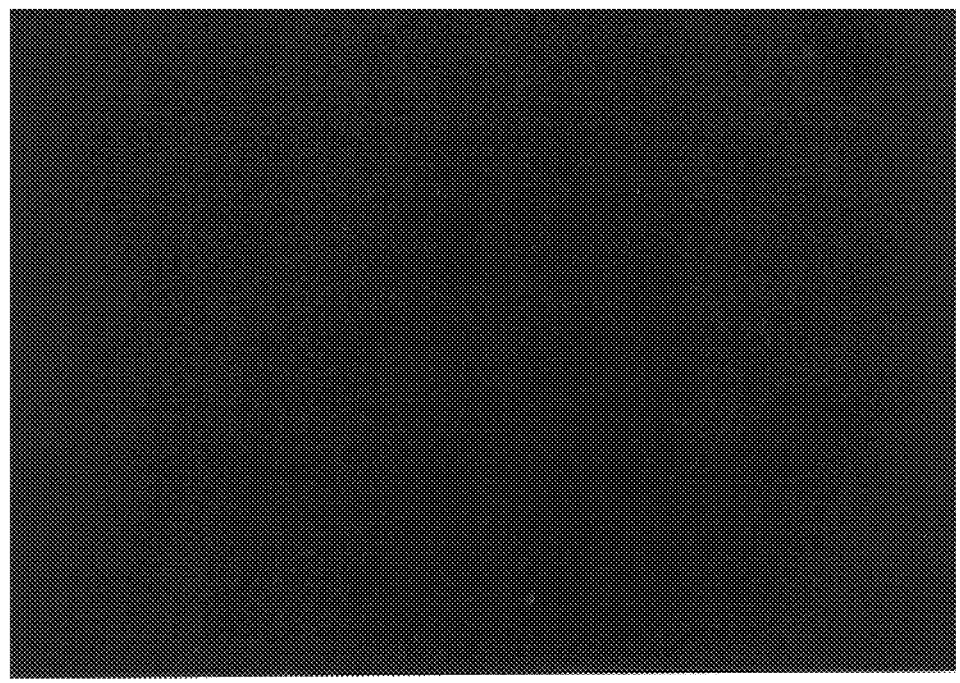
Fluorescent　　　FIGURE 2B

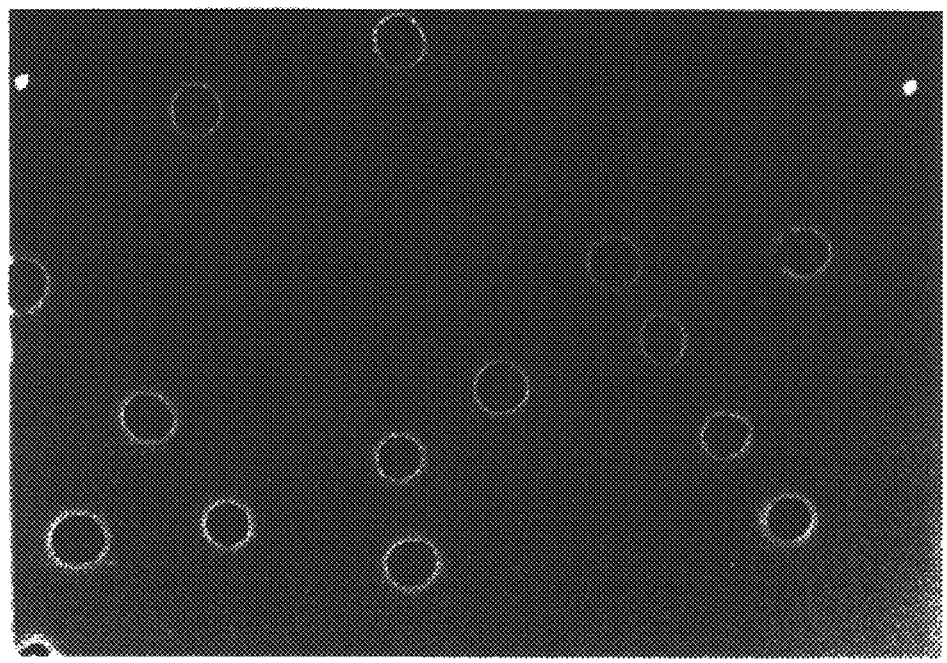
Phase Contrast    FIGURE 2C    Control
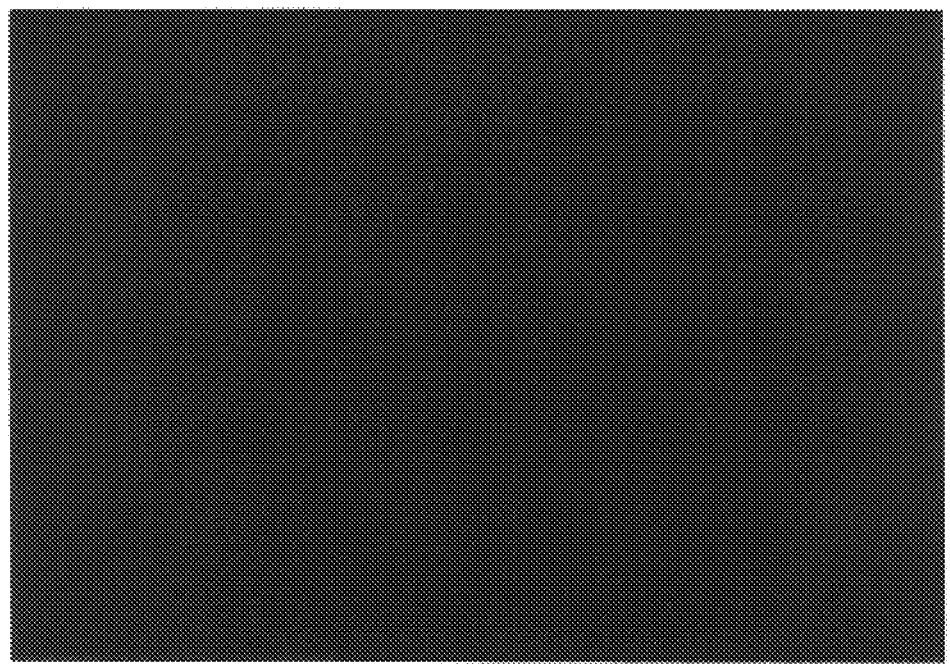
Fluorescent    FIGURE 2D    Control

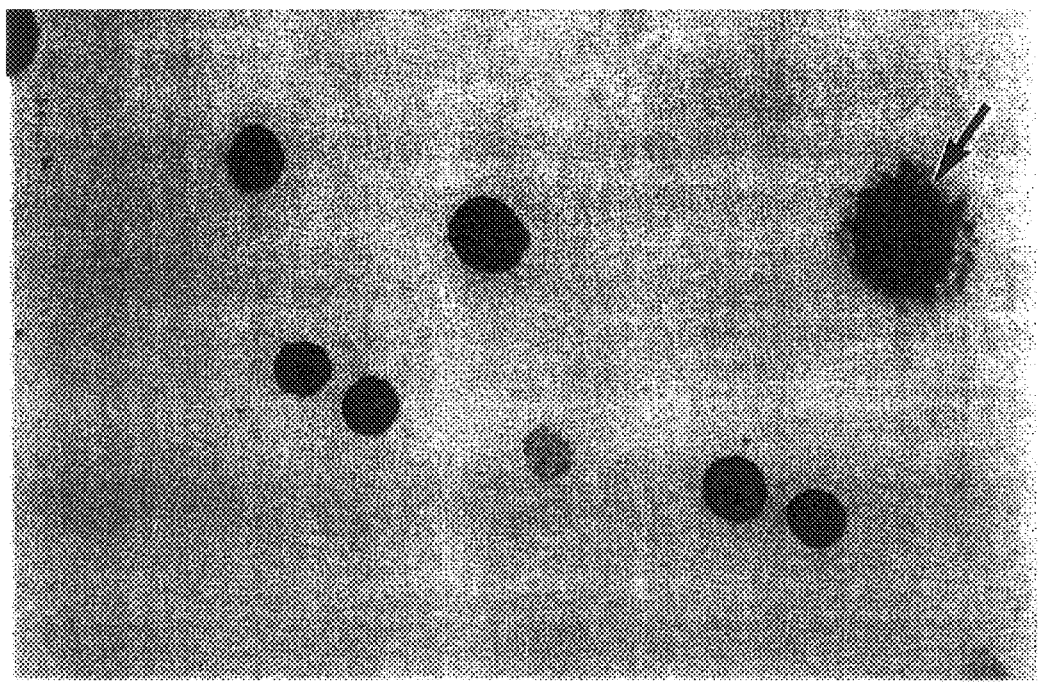
FIGURE 3A
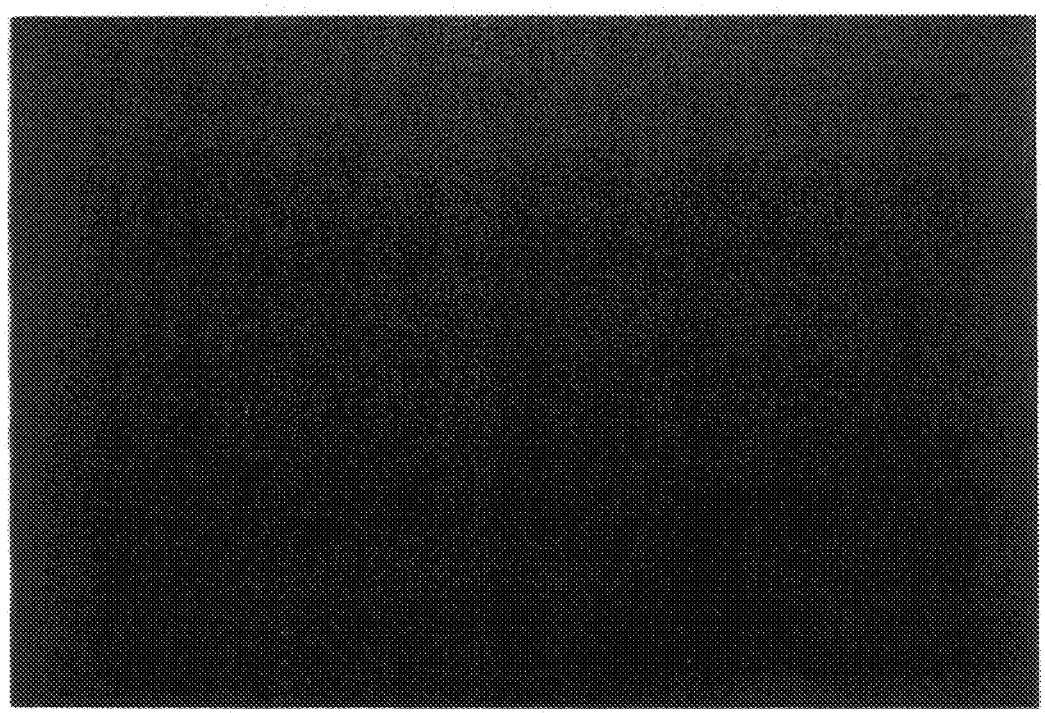
FIGURE 3B          Control

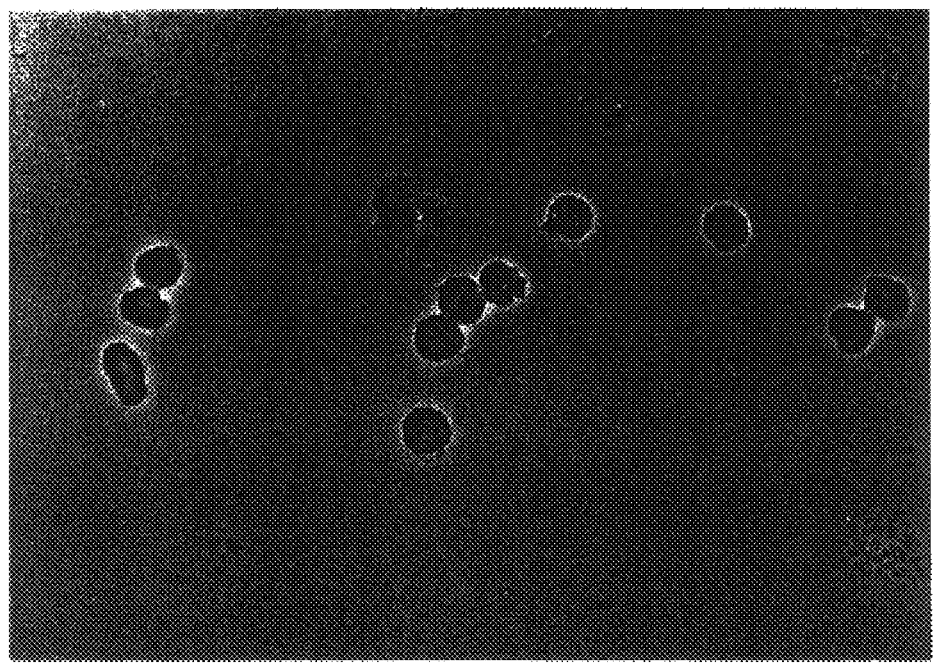
Phase Contrast  FIGURE 4A
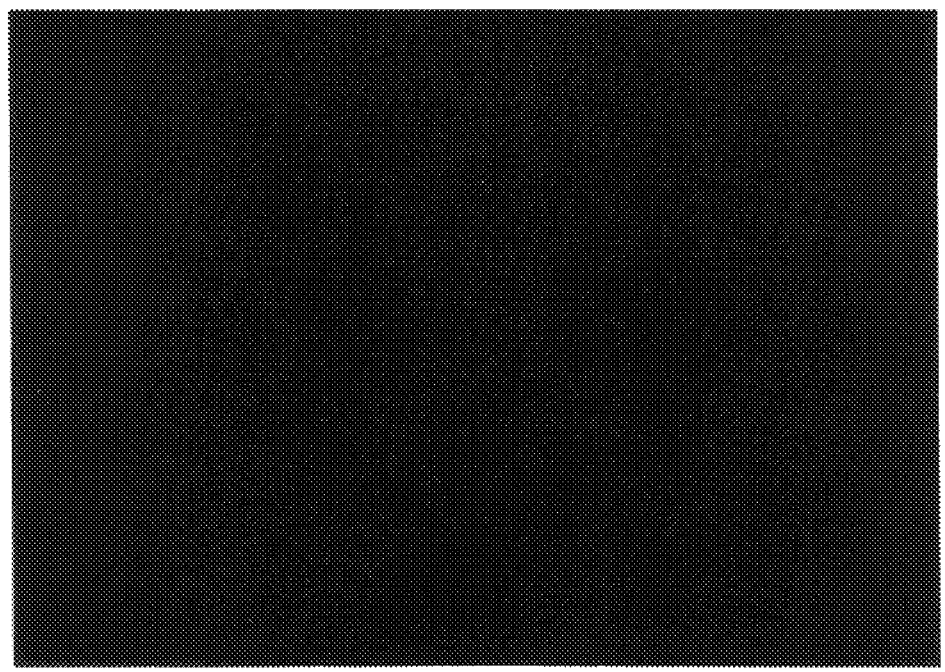
Fluorescent  FIGURE 4B

HCMV (Towne) -> Full Restriction Map

DNA sequence    616 b.p.    ggcgaccgccca ... agtgacgtaagt    linear

Positions of Restriction Endonucleases sites (unique sites underlined)

```
                                                                                                        80
                            Mae II
                            Aha II                    Mae II
                            Aat II         Mae III
                            HinC II                                         Mae III
                            | | |           | |                              |
                            | | |          26 29                             |
                                            29                               57
                                            30
GGCGACCGCCCAGCGACCCCGCCCGTTGACGTCAATAGTGACGTATGTTCCCATAGTAACGCCAATAGGGACTTTCCAT
CCGCTGGCGGGTCGCTGGGGCGGGCAACTGCAGTTATCACTGCATACAAGGGTATCATTGCGGTTATCCCTGAAAGGTA
    .         .         .         .         .         .         .         .

160
                                            Bgl I           Rsa I                    Nde I
                                             |               |                        |
                                            114             126                      141
TGACGTCAATGGGTGGAGTATTTACGGTAAACTGCCCACTTGGCAGTACATCAAGTGTATCATATGCCAAGTCCGCCCCC
ACTGCAGTTACCCACCTCATAAATGCCATTTGACGGGTGAACCGTCATGTAGTTCACATAGTATACGGTTCAGGCGGGGG
    .         .         .         .         .         .         .         .
Mae II
Aha II
Aat II
| |
| |
82
82
83
```

| Enzyme | | Enzyme | | Enzyme | | Enzyme | |
|---|---|---|---|---|---|---|---|
| Alw I | 1 | BstE II | – | Gsu I | 1 | Ncl I | – | Sca I | 2 |
| AlwN I | – | BstN I | – | Hae I | – | Nco I | – | ScrF I | 1 |
| Apa I | – | BstU I | – | Hae II | – | Nde I | – | Sec I | 1 |
| ApaL I | – | BstX I | – | Hae III | 2 | Nhe I | – | SfaN I | – |
| Ase I | – | BstY I | – | Hga I | 2 | Nla III | 2 | Sfi I | 2 |
| Asp718 | – | Bsu36 I | – | HgiA I | 1 | Nla IV | 2 | Sma I | 2 |
| Ava I | 1 | Cfr10 I | – | HgiE II | – | Not I | – | SnaB I | – |
| Ava II | – | Cla I | – | Hha I | – | Nru I | – | Spe I | 1 |
| Avr II | – | Dde I | 2 | HinC II | 2 | Nsi I | 2 | Sph I | 1 |
| BamH I | – | Dpn I | – | HinD III | – | Nsp7524 I | – | Spl I | 1 |
| Ban I | 1 | Dra I | – | Hinf I | – | NspB II | 2 | Ssp I | 1 |
| Ban II | 1 | Dra III | – | HinP I | – | NspH I | 1 | Stu I | 1 |
| Bbe I | – | Drd I | – | Hpa I | – | Pac I | – | Sty I | 1 |
| Bbv I | 2 | Dsa I | 2 | Hpa II | 2 | PaeR7 I | 2 | Taq I | – |
| Bbv II | 1 | Eae I | 1 | Hph I | 1 | PflM I | 1 | Tth111 I | 1 |
| Bcl I | – | Eag I | – | Kpn I | – | Ple I | 1 | Tth111 II | – |
| Bcn I | – | Ear I | 2 | Mae I | 7 | Pml I | – | Xba I | 1 |
| Bgl I | 2 | Eco47 III | – | Mae II | 3 | PpuM I | – | Xca I | – |
| Bgl II | – | Eco57 I | 2 | Mae III | 2 | Pst I | – | Xho I | – |
| BsaA I | 1 | EcoN I | – | Mbo I | 1 | Pvu I | – | Xcm I | – |
| Bsm I | – | EcoO109 I | – | Mbo II | – | Pvu II | – | Xma I | – |
| BsmA I | 2 | EcoR I | – | Mlu I | – | Rsa I | 5 | Xmn I | – |
| Bsp1286 I | 1 | EcoR II | 1 | Mme I | – | | | | |

| Enzyme | Site | Use | Site position (Fragment length) Fragment order |
|---|---|---|---|
| Alu I | ag/ct | 1 | 1( 471) 1 472( 145) 2 |
| Alw I | ggatc | 1 | 1( 548) 1 549( 68) 2 |
| Ava II | g/gwcc | 1 | 1( 543) 1 544( 73) 2 |
| Ban I | g/gyrcc | 1 | 1( 372) 1 373( 244) 2 |

FIG. 6A-6

| Enzyme | Site | Cut | | | | | | | |
|---|---|---|---|---|---|---|---|---|---|
| Ban II | grgcy/c | | 1 | 1( | 470) | 1 | 471( | 146) | 2 |
| Bbv II | gaagac | 2/6 | 1 | 1( | 533) | 1 | 534( | 83) | 2 |
| BsaA I | yac/gtr | | 1 | 1( | 245) | 2 | 246( | 371) | 1 |
| Bsp1286 I | gdgch/c | | 1 | 1( | 470) | 1 | 471( | 146) | 2 |
| Bsr I | actgg | 1/-1 | 1 | 1( | 202) | 2 | 203( | 414) | 1 |
| BstN I | cc/wgg | | 1 | 1( | 497) | 1 | 498( | 119) | 2 |
| Eae I | y/ggccr | | 1 | 1( | 561) | 1 | 562( | 55) | 2 |
| Eag I | c/ggccg | | 1 | 1( | 561) | 1 | 562( | 55) | 2 |
| EcoR II | /ccwgg | | 1 | 1( | 497) | 1 | 498( | 119) | 2 |
| Fnu4H I | gc/ngc | | 1 | 1( | 560) | 1 | 561( | 56) | 2 |
| Fok I | ggatg | 9/13 | 1 | 1( | 508) | 1 | 509( | 108) | 2 |
| Gdi II | yggccg | -5/-1 | 1 | 1( | 561) | 1 | 562( | 55) | 2 |
| Gsu I | ctggag | 16/14 | 1 | 1( | 498) | 2 | 499( | 118) | 2 |
| HgiA I | gwgcw/c | | 1 | 1( | 470) | 1 | 471( | 146) | 2 |
| Hph I | ggtga | 8/7 | 2 | 1( | 271) | 2 | 272( | 345) | 2 |
| Mae I | c/tag | | 2 | 1( | 190) | 2 | 191( | 426) | 2 |
| Mbo II | gaaga | 8/7 | 2 | 1( | 533) | 1 | 534( | 83) | 2 |
| Nco I | c/catgg | | 1 | 1( | 267) | 2 | 268( | 349) | 1 |
| Nde I | ca/tatg | | 2 | 1( | 140) | 2 | 141( | 476) | 1 |
| NspB II | cmg/ckg | | 1 | 1( | 558) | 1 | 559( | 58) | 2 |
| Ple I | gagtc | 4/5 | 2 | 1( | 317) | 2 | 318( | 299) | 2 |
| Sac I | gagct/c | | 1 | 1( | 470) | 1 | 471( | 146) | 2 |
| Sac II | ccgc/gg | | 1 | 1( | 558) | 1 | 559( | 58) | 2 |
| SfaN I | gcatc | 5/9 | 2 | 1( | 274) | 2 | 275( | 342) | 2 |
| SnaB I | tac/gta | | 1 | 1( | 245) | 2 | 246( | 371) | 1 |
| Sty I | c/cwwgg | | 1 | 1( | 267) | 2 | 268( | 349) | 1 |
| Bcn I | ccs/gg | | 2 | 1( | 540) | 1 | 541( | 24) | 3 | 565( | 52) | 2 |
| Bgl I | gccnnnn/nggc | | 2 | 1( | 113) | 1 | 114( | 441) | 1 | 555( | 62) | 3 |
| BsmA I | gtctc | 1/5 | 2 | 1( | 336) | 1 | 337( | 165) | 2 | 502( | 115) | 3 |
| BstU I | cg/cg | | 2 | 1( | 559) | 1 | 560( | 25) | 3 | 585( | 32) | 2 |
| Dpn I | ga/tc | | 2 | 1( | 492) | 1 | 493( | 56) | 3 | 549( | 68) | 2 |
| Dsa I | c/crygg | | 2 | 1( | 267) | 2 | 268( | 291) | 1 | 559( | 58) | 3 |
| Hae II | gg/cc | | 2 | 1( | 183) | 2 | 184( | 379) | 3 | 563( | 54) | 3 |
| Hga I | gacgc | 5/10 | 2 | 1( | 424) | 1 | 425( | 79) | 3 | 504( | 113) | 2 |

FIG. 6A-7

| Enzyme | Site | | | | | | | |
|---|---|---|---|---|---|---|---|---|
| HinC II | gty/rac | 2 | 1( | 25) | 3 | 26( | 396) | 1 | 422( | 195) | 2 |
| Hinf I | g/antc | 2 | 1( | 317) | 1 | 318( | 271) | 2 | 589( | 28) | 3 |
| Hpa II | c/cgg | 2 | 1( | 540) | 1 | 541( | 24) | 3 | 565( | 52) | 2 |
| Mbo I | /gatc | 2 | 1( | 492) | 1 | 493( | 56) | 3 | 549( | 68) | 2 |
| Msp I | c/cgg | 2 | 1( | 540) | 1 | 541( | 24) | 3 | 565( | 52) | 2 |
| Nci I | cc/sgg | 2 | 1( | 540) | 1 | 541( | 24) | 3 | 565( | 52) | 2 |
| Nla III | catg/ | 2 | 1( | 208) | 2 | 209( | 60) | 3 | 269( | 348) | 1 |
| Nla IV | ggm/ncc | 2 | 1( | 372) | 1 | 373( | 170) | 2 | 543( | 74) | 3 |
| Sau3A I | /gatc | 2 | 1( | 492) | 1 | 493( | 56) | 3 | 549( | 68) | 2 |
| Sau96 I | g/gncc | 2 | 1( | 183) | 2 | 184( | 360) | 1 | 544( | 73) | 3 |
| Sec I | c/cnngg | 2 | 1( | 267) | 2 | 268( | 291) | 1 | 559( | 58) | 3 |
| Mae III | /gtnac | 3 | 1( | 38) | 2 | 39( | 18) | 3 | 57( | 549) | 1 |
|  |  |  | 606( | 11) | 4 |  |  |  |  |  |  |
| Mnl I | cctc | 3 | 1( | 455) | 1 | 456( | 70) | 2 | 526( | 30) | 4 |
|  |  |  | 556( | 61) | 3 |  |  |  |  |  |  |
| ScrF I | cc/ngg | 3 | 1( | 497) | 1 | 498( | 43) | 3 | 541( | 24) | 4 |
|  |  |  | 565( | 52) | 2 |  |  |  |  |  |  |
| Aat II | gacgt/c | 4 | 1( | 28) | 5 | 29( | 53) | 4 | 82( | 83) | 3 |
|  |  |  | 165( | 186) | 2 | 351( | 266) | 1 |  |  |  |
| Aha II | gr/cgyc | 5 | 1( | 28) | 6 | 29( | 53) | 5 | 82( | 83) | 4 |
|  |  |  | 165( | 186) | 1 | 351( | 153) | 2 | 504( | 113) | 3 |
| Rsa I | gt/ac | 5 | 1( | 125) | 3 | 126( | 80) | 4 | 206( | 33) | 6 |
|  |  |  | 239( | 51) | 5 | 290( | 157) | 2 | 447( | 170) | 1 |
| Mae II | a/cgt | 7 | 1( | 29) | 6 | 30( | 12) | 7 | 42( | 41) | 5 |
|  |  |  | 83( | 83) | 3 | 166( | 81) | 4 | 247( | 105) | 2 |
|  |  |  | 352( | 257) | 1 | 609( | 8) | 8 |  |  |  |

98 sites found

No Sites found for the following Restriction Endonucleases

| | | | |
|---|---|---|---|
| Dra III | cacnnn/gtg | Nsp7524 I | r/catgy |
| Acc I | gt/mkac | | |

FIG. 6A-8

| | | | | | | |
|---|---|---|---|---|---|---|
| Afl II | c/ttaag | Drd I | gacnnnn/nngtc | NspH I | rcatg/y |
| Afl III | a/crygt | Ear I | ctcttc 1/4 | Pac I | ttaat/taa |
| AlwN I | cagnnn/ctg | Eco47 III | agc/gct | PaeR7 I | c/tcgag |
| Apa I | gggcc/c | Eco57 I | ctgaag 16/14 | PflM I | ccannnn/ntgg |
| ApaL I | g/tgcac | EcoN I | cctnn/nnnagg | Pml I | cac/gtg |
| Ase I | at/taat | EcoO109 I | rg/gnccy | PpuM I | rg/gwccy |
| Asp718 | g/gtacc | EcoR I | g/aattc | Pst I | ctgca/g |
| Ava I | c/ycgrg | EcoR V | gat/atc | Pvu I | cgat/cg |
| Avr II | c/ctagg | Esp I | gc/tnagc | Pvu II | cag/ctg |
| BamH I | g/gatcc | Fsp I | tgc/gca | Rsr II | cg/gwccg |
| Bbe I | ggcgc/c | Hae I | wgg/ccw | Sal I | g/tcgac |
| Bbv I | gcagc 8/12 | Hae II | rgcgc/y | Sca I | agt/act |
| Bcl I | t/gatca | HgiE II | accnnnnnggt | Sfi I | ggccnnnn/nggcc |
| Bgl II | a/gatct | Hha I | gcg/c | Sma I | ccc/ggg |
| Bsm I | gaatgc 1/-1 | HinD III | a/agctt | Spe I | a/ctagt |
| BspH I | t/catga | HinP I | g/cgc | Sph I | gcatg/c |
| BspM I | acctgc 4/8 | Hpa I | gtt/aac | Spl I | c/gtacg |
| BspM II | t/ccgga | Kpn I | ggtac/c | Ssp I | aat/att |
| BssH II | g/cgcgc | Mlu I | a/cgcgt | Stu I | agg/cct |
| BstB I | tt/cgaa | Mme I | tccrac 20/18 | Taq I | t/cga |
| BstE II | g/gtnacc | Msc I | tgg/cca | Tth111 I | gacn/nngtc |
| BstX I | ccannnn/ntgg | Mse I | t/taa | Tth111 II | caarca 11/9 |
| BstY I | r/gatcy | Nae I | gcc/ggc | Xba I | t/ctaga |
| Bsu36 I | cc/tnagg | Nar I | gg/cgcc | Xca I | gta/tac |
| Cfr10 I | r/ccggy | Nhe I | g/ctagc | Xho I | c/tcgag |
| Cla I | at/cgat | Not I | gc/ggccgc | Xcm I | ccannnnn/nnnntgg |
| Dde I | c/tnag | Nru I | tcg/cga | Xma I | c/ccggg |
| Dra I | ttt/aaa | Nsi I | atgca/t | Xmn I | gaann/nnttc |

FIG. 6A-9

*** Aligned sequences:
C1 ( 1f): |>u 1>+++++ ad169hcmv (930 bases)+++++>u 930>|
C2 ( 1f): |>u 1>+++++ townehcmv (616 bases)+++++>u 616>|

*** Alignment of first sequence with all others displayed
*** Key:
  UPPER CASE = aligned non-identical bases
  lower case = unaligned bases
  --------- = aligned identical bases
  .......... = gap ad169hcmv : AATCAATATTGGCCATTAGCCATATATTCATTGGTTATATAGCATAAATCAATATTGGC
townehcmv : ..........................................................

ad169hcmv : TATTGGCCATTGCATACGTTGTATCCATATCATAATATGTACATTTATATTGGCTCATGT
townehcmv : ..........................................................

ad169hcmv : CCAACATTACCGCCATGTTGATTATTGACTAGTTATTAATAGTAATCAATTACG
townehcmv : ..........................................................

ad169hcmv : GGGTCATTAGTTCATAGCCCATATATGGAGTTCCGCGTTACATAACTTACGGTAAATGGC
townehcmv : ..........................................................

ad169hcmv : CCGCCTGGCTGACCGCCCAACGACCCCCGCCCATTGACGTCAATAATGACGTATGTTCCC
townehcmv : ............................-------G------G--------------- ad169hcmv : ATAGTAACGCCAATAGGGACTTTCCATTGACGTCAATGGGTGGAGTATTTACGGTAAACT
townehcmv : ----------------------------------------------------------

FIG. 6B-1

```
ad169hcmv : GCCCACTTGGCAGTACATCAAGTGTATCATATGCCAAGTACGCCCCTATTGACGTCAAT
townehcmv : ------------------------------------C----------------------- ad169hcmv : GACGGTAAATGGCCCGCCTGGCATTATGCCCAGTACATGACCTTATGGGACTTTCCTACT
townehcmv : ---------------------------A--------------C-------G--------- ad169hcmv : TGGCAGTACATCTACGTATTAGTCATCGCTATTACCATGGTGATGCGGTTTTGGCAGTAC
townehcmv : ------------------------*----------------------------------- ad169hcmv : ATCAATGGGCGTGGATAGCGGTTTGACTCACGGGGATTTCCAAGTCTCCACCCCATTGAC
townehcmv : -C---------------------------------------------------------- ad169hcmv : GTCAATGGGAGTTTGTTTTGGCACCAAAATCAACGGGACTTTCCAAAATGTCGTAACAAC
townehcmv : --------------------------------------------------T--------- ad169hcmv : TCCGCCCCATTGACGCAAATGGGCGGTAdGCGTGTACGGTGGGAGGTCTATATAAGCAGA
townehcmv : C-----G-----------------------------------------------.----- ad169hcmv : GCTCGTTTAGTGAACCGTCAGATCGCCTGGAGACGCCATCCACGCTGTTTGACCTCCAT
townehcmv : ------------------------------------------------------------ ad169hcmv : AGAAGACACCGGGACCGATCCAGCCTCCGCGGCCGGGAACGGTGCATTGGAACGCGGATT
townehcmv : ------------------------------------------------------------ ad169hcmv : CCCCGTGCCAAGAGTGACGTAAGTACCGCCTATAGAGTCTATAGGCCCACCCCCTTGGCT
townehcmv : ------------------------------------------.................

ad169hcmv : TCTTATGCATGCTATACTGTTTTTGGCTTG
townehcmv : ..............................
```

FIG. 6B-2

```
LOCUS        HS5IEE        930 bp  ds-DNA             VRL       15-SEP-1989
DEFINITION   Human cytomegalovirus major immediate-early gene, enhancer.
ACCESSION    K03104
KEYWORDS     major immediate-early gene.
SOURCE       HCMV strain AD169.
  ORGANISM   Human cytomegalovirus
             Viridae; ds-DNA enveloped viruses; Herpesviridae;
             Betaherpesvirinae.
REFERENCE    1  (bases 1 to 930)
  AUTHORS    Boshart,M., Weber,F., Jahn,G., Dorsch-Haesler,K.,
             Fleckenstein,B. and Schaffner,W.
  TITLE      A very strong enhancer is located upstream of an immediate
             early gene of human cytomegalovirus
  JOURNAL    Cell 41, 521-530 (1985)
  STANDARD   full automatic
REFERENCE    2  (sites)
  AUTHORS    Zhang,X.-Y., Inamdar,N.M., Supakar,P.C., Wu,K., Ehrlich,M.
             and Ehrlich,K.C.
  TITLE      three MDBP sites in the immediate-early enhancer-promoter
             region of human cytomegalovirus
  JOURNAL    Virology 182, 865-869 (1991)
  STANDARD   full automatic
COMMENT      Draft entry and printed copy of sequence in [1] were kindly
             provided by M.Boshart, 24-OCT-1985.
             The sequence shown is a 930 bp segment of the PstI m-fragment
             from HCMV strain AD169.  The enhancer region of the HCMV gene
```

FIG. 6B-3 was defined by selecting for fragments of HCMV DNA that would restore efficient growth of enhancerless SV40.

FEATURES             Location/Qualifiers
     misc_signal     214..620
                     /note="HCMV IE enhancer region"
     mRNA            738..>930
                     /note="HCMV IE mRNA"

BASE COUNT    233 A    228 C    211 G    258 T

ORIGIN      12 bp upstream of BalI site; .750 mu.
  1 AATCAATATT GGCCATTAGC CATATTATTC ATTGGTTATA TAGCATAAAT CAATATTGGC
 61 TATTGGCCAT TGCATACGTT GTATCCATAT CATAAATATGT ACATTTATAT TGGCTCATGT
121 CCAACATTAC CGCCATGTTG ACATTGATTA TTGACTAGTT ATTAATAGTA ATCAATTACG
181 GGGTCATTAG TTCATAGCCC ATATATGGAG TTCCGCGTTA CATAACTTAC GGTAAATGGC
241 CCGCCTGGCT GACCGCCCAA CGACCCCCGC CCATTGACGT CAATAATGAC GTATGTTCCC
301 ATAGTAACGC CAATAGGGAC TTTCCATTGA CGTCAATGGG TGGAGTATTT ACGGTAAACT
361 GCCCACTTGG CAGTACATCA AGTGTATCAT ATGCCAAGTA CGCCCCCTAT TGACGTCAAT
421 GACGGTAAAT GGCCCGCCTG GCATTATGCC CAGTACATGA CCTTATGGGA CTTTCCTACT
481 TGGCAGTACA TCTACGTATT AGTCATCGCT ATTACCATGG TGATGCGGTT TTGGCAGTAC
541 ATCAATGGGC GTGGATAGCG GTTTGACTCA CGGGGATTTC CAAGTCTCCA CCCCATTGAC
601 GTCAATGGGA GTTTGTTTTG GCACCAAAAT CAACGGGACT TTCCAAAATG TCGTAACAAC
661 TCCGCCCCAT TGACGCAAAT GGGCGGTAGG CGTGTACGGT GGGAGGTCTA TATAAGCAGA
721 GCTCGTTTAG TGAACCGTCA GATCGCCTGG AGACGCCATC CACGCTGTTT TGACCTCCAT
781 AGAAGACACC GGGACCGATC CAGCCTCCGC GGCCGGGAAC GGTGCATTGG AACGCGGATT
841 CCCCGTGCCA AGAGTGACGT AAGTACCGCC TATAGAGTCT ATAGGCCCAC CCCCTTGGCT
901 TCTTATGCAT GCTATACTGT TTTTGGCTTG

FIG. 6B-4

| | | |
|---|---|---|
| LOCUS | HS5MIE1 | 616 bp ds-DNA        VRL    15-SEP-1989 |
| DEFINITION | Human cytomegalovirus (Towne) major immediate-early (IE) gene, exon 1. | |
| ACCESSION | K01484 K01090 | |
| KEYWORDS | major immediate-early gene. | |
| SEGMENT | 1 of 4 | |
| SOURCE | Human cytomegalovirus (strain Towne) passed in primary human foreskin fibroblasts, DNA [1], clone pXEP22 [2]. | |
| ORGANISM | Human cytomegalovirus Viridae; ds-DNA enveloped viruses; Herpesviridae; Betaherpesvirinae. | |
| REFERENCE | 1 (bases 460 to 616) | |
| AUTHORS | Stenberg,R.M., Thomsen,D.R. and Stinski,M.F. | |
| TITLE | Structural analysis of the major immediate early gene of human cytomegalovirus | |
| JOURNAL | J. Virol. 49, 190-199 (1984) | |
| STANDARD | full automatic | |
| REFERENCE | 2 (bases 1 to 490) | |
| AUTHORS | Thomsen,D.R., Stenberg,R.M., Goins,W.F. and Stinski,M.F. | |
| TITLE | Promoter-regulatory region of the major immediate early gene of human cytomegalovirus | |
| JOURNAL | Proc. Natl. Acad. Sci. U.S.A. 81, 659-663 (1984) | |
| STANDARD | full automatic | |

FIG. 6B-5

COMMENT    IE region 1 gene is also known as the major IE gene.
Cytomegalovirus immediate-early gene expression is dominated
in vivo by the expression of a single gene. At least three
promoters influence transcription of the virus after
infection. When a complete set of promoter-regulatory
regions were present (IE regions 1, 2 and 3 or IE region 1
and an adenovirus major late promoter), transcription was
qualitatively higher from IE region 1.

Based on these data, [1] proposes that the upstream sequence
of the IE region 1 gene competes more efficiently for RNA
polymerase II or other host cell proteins necessary for in
vitro transcription.

Consensus CAAT and TATA boxes were found at positions 429-433
and 462-467, a polyadenylation signal was found at positions
2198-2203.

Fourteen direct repeats were found in the promoter-regulatory
region (four 16-bp repeats, four 18-bp repeats, four 19-bp
repeats and two 21-bp repeats).

Draft entry and clean copy sequences [1], [2] kindly provided
by P.R. Witte and M.F. Stinski (10-FEB-1986].

FIG. 6B-6

```
FEATURES             Location/Qualifiers
     prim_transcript 490..>616
                     /note="major IE mRNA"
     intron          611..>616
                     /note="major IE mRNA intron A"
BASE COUNT      28       144 A    165 C    162 G    145 T
ORIGIN          bp upstream of HincII site; 0.752 map units.
    1 GGCGACCGCC CAGGGACCCC CGCCCGTTGA CGTCAATAGT GACGTATGTT CCCATAGTAA
   61 CGCCAATAGG GACTTTCCAT TGACGTCAAT GGGTGGAGTA TTTACGGTAA ACTGCCCACT
  121 TGGCAGTACA TCAAGTGTAT CATATGCCAA GTCCGCCCCC TATTGACGTC AATGACGGTA
  181 AATGGCCCGC CTAGCATTAT GCCCAGTACA TGACCTTACG GGAGTTTCCT ACTTGGCAGT
  241 ACATCTACGT ATTAGTCATC GCTATTACCA TGGTGATGCG GTTTTGGCAG TACACCAATG
  301 GGCGTGGATA GCGGTTTGTT TTGGCACCAA AATCAACGGG ACTTTCCAAA ATGTCGTAAT
  361 GGAGTTTGTT TTGGCACCAA AATCAACGGG ACTTTCCAAA ATGTCGTAAT AACCCCGCCC
  421 CGTTGACGCA AATGGGCGGT AGGCGTGTAC GGTGGGAGGT CTATATAGCA GAGCTCGTTT
  481 AGTGAACCGT CAGATCGCCT GGAGACGCCA TCCACGCTGT TTTGACCTCC ATAGAAGACA
  541 CCGGGACCGA TCCAGCCTCC GCGGCCGGGA ACGGTGCATT GGAACGCGGA TTCCCCGTGC
  601 CAAGAGTGAC GTAAGT
```

FIG. 6B-7

HCMV (AD169) -> Full Restriction Map

DNA sequence    930 b.p.    aatcaatattgg ... gtttttggcttg    linear

Positions of Restriction Endonucleases sites (unique sites underlined)

```
          Hae III
          Msc I                                                      Hae III
          Hae I                                                      Msc I
          Eae I                                                      Hae I
Ssp I     | |                                    Ssp I               Eae I              Mae II
|         |||                                    |                   |||                |                               80
AATCAATATATTATTCATTGGTTATATATAGCATAAATCAATATTGGTTATATATAGCATAAATCAATATTGGCTATTGGCCATTGCATAACGTT
TTAGTTATATAAGTAACCAATATATATCGTATTTAGTTATATAAGTAACCAATATATATCGTATTTAGTTATAACCGATAACCGGTAACGTATGCAA
|         |||                                    |                   |||                |
5         10                                     52                  64                  76
          10                                                         64
          10                                                         64
          11                                                         65

Mme I                      HinC II              Mae I
                               Rsa I        Nla III           Nla III  Nla III              Spe I
                               |            |                 |        ||                   ||                         160
GTATCCATATCATATAATATATGTACATTTATATATTGGCTCATGTTGACATTTATATATTGGCTCATGTTGACATTGATTATTGACTAGTT
CATAGGTATAGTATATTATATACATGTAACATATATAACCGAGTACAGGTTGTAATGGCGGTACAACTGTAACTAATAACTGATCAA
                               |            |                 |        ||                   ||
                               99           116               134      137                 154
                                            120                                            155
```

FIG. 6C-1

```
                                                                          Bgl I
                                                                          Sau96 I
                                              Mae III                     Hae III
                                              BstU I                      | | |
Mse I                                         | |                         238
Age I                                         214                         238
| |                                           217                         239
ATTAATAGTAATCAATTACGGGGTCATTAGTTCATAGCCCATATATGGAGTTCCGCGTTACATATAACTTACGGTAAATGGC
TAATTATCATTAGTTAAGTTAATGCCCAGTAATCAAGTATCGGGTATATACCTCAAGGCGCAATGTATTGAATGCCATTACCG
161
162                                                                      240

Mae III
                                       Mae II                | |
                                       Aha II                304
             Mae II                    Aat II
             Aha II                    | |
ScrF I       Aat II                    276
EcoR II      | |                       276
BstN I       244                       277
| | |        244
CCGCCTGGCTGACCGCCCAACGACCCCCGCCATTGACGTCAATAAATGACGTATGTTCCCATAGTAACGCCAATAGGGAC
GGCGGACCGACTGGCGGGTTGCTGGGGGCGGTAACTGCAGTTATTTACTGCATACAAGGGTATCATTGCGGTTATCCCTG
244
244
244                                                                      320

Bgl I           Rsa I              Nde I    Rsa I
                                        | |             | |                | |      | |
             Mae II                     361            373                388      398
             Aha II
             Aat II
             | | |
TTTCCATTGACGTCAATGGGTGGAGTATTTACGGTAAACTGCCCACTTGGCAGTACATCAAGTGTATCATATGCCAAGTA
AAAGGTAACTGCAGTTACCCACCTCATAAATGCCATTTGACGGGTGAACCGTCATGTAGTTCACATAGTATACGGTTCAT
329
329
330                                                                      400
```

```
                                        Nla III
                                        Sph I
                                        NspH I
                                        Nsp7524 I
      BstX I                            Nsi I
      Sau96 I    Sty I                   | | |
      Hae III    Sec I                   | | |
      |  |        |                      | | |
ATAGGCCCACCCCCTTGGCTTCTTATGCATGCTATACTGTTTTTGGCTTG   930
TATCCGGGTGGGGGAACCGAAGAATACGTACGATATGACAAAACCGAAC
 |  |        |                      | | |
884  884     893                    905
   887       893                      907
                                      907
                                      908
```

Restriction Endonucleases site usage

| Enzyme | # | Enzyme | # | Enzyme | # | Enzyme | # | Enzyme | # |
|---|---|---|---|---|---|---|---|---|---|
| Aat II | 4 | BspH I | - | EcoR V | - | Mnl I | 3 | Rsr II | - |
| Acc I | - | BspM I | - | Esp I | - | Msc I | 2 | Sac I | 1 |
| Afl II | - | BspM II | - | Fnu4H I | 1 | Mse I | 1 | Sac II | 1 |
| Afl III | - | Bsr I | 1 | Fok I | 1 | Msp I | 2 | Sal I | - |
| Aha II | 5 | BssH II | - | Fsp I | - | Nae I | - | Sau3A I | 2 |
| Alu I | 1 | BstB I | - | Gdi II | 1 | Nar I | - | Sau96 I | 4 |
| Alw I | 1 | BstE II | - | Gsu I | 1 | Nci I | 2 | Sca I | - |
| AlwN I | - | BstN I | 3 | Hae I | 2 | Nco I | 1 | ScrF I | 5 |
| Apa I | - | BstU I | 3 | Hae II | - | Nde I | 1 | Sec I | 3 |
| ApaL I | - | BstX I | 1 | Hae III | 6 | Nhe I | - | SfaN I | 1 |
| Ase I | 1 | BstY I | - | Hga I | 2 | Nla III | 5 | Sfi I | - |
| Asp718 | - | Bsu36 I | - | HgiA I | 1 | Nla IV | 2 | Sma I | - |
| Ava I | - | Cfr10 I | - | HgiE II | - | Not I | - | SnaB I | 1 |
| Ava II | 1 | Cla I | - | Hha I | - | Nru I | - | Spe I | 1 |
| Avr II | - | Dde I | - | HinC II | 1 | Nsi I | 1 | Sph I | 1 |
| BamH I | - | Dpn I | 2 | HinD III | - | Nsp7524 I | 1 | Spl I | - |
| Ban I | 1 | Dra I | - | Hinf I | 3 | NspB II | 1 | Ssp I | 2 |

| Enzyme | Count | Enzyme | Count | Enzyme | Count | Enzyme | Count | Enzyme | Count |
|---|---|---|---|---|---|---|---|---|---|
| Ban II | 1 | Dra III | - | HinP I | - | NspH I | 1 | Stu I | - |
| Bbe I | - | Drd I | - | Hpa I | - | Pac I | - | Sty I | 2 |
| Bbv I | - | Dsa I | 2 | Hpa II | 2 | PaeR7 I | - | Taq I | - |
| Bbv II | 1 | Eae I | 3 | Hph I | 1 | PflM I | - | Tth111 I | - |
| Bcl I | - | Eag I | 1 | Kpn I | - | Ple I | 2 | Tth111 II | - |
| Bcn I | 2 | Ear I | - | Mae I | 1 | Pml I | - | Xba I | - |
| Bgl I | 4 | Eco47 III | - | Mae II | 8 | PpuM I | - | Xca I | - |
| Bgl II | - | Eco57 I | - | Mae III | 4 | Pst I | - | Xho I | - |
| BsaA I | 1 | EcoN I | - | Mbo I | 2 | Pvu I | - | Xcm I | - |
| Bsm I | - | Eco0109 I | - | Mbo II | 1 | Pvu II | - | Xma I | - |
| BsmA I | 2 | EcoR I | - | Mlu I | - | Rsa I | 8 | Xmn I | - |
| Bsp1286 I | 1 | EcoR II | 3 | Hme I | 1 | | | | |

| Enzyme | Site | | Use | Site position (Fragment length) Fragment order | | | | | |
|---|---|---|---|---|---|---|---|---|---|
| Alu I | ag/ct | | 1 | 1( 719) 1 | 720( 211) 2 | | | | |
| Alw I | ggatc | 4/5 | 1 | 1( 796) 1 | 797( 134) 2 | | | | |
| Ase I | at/taat | | 1 | 1( 160) 2 | 161( 770) 1 | | | | |
| Ava II | g/gwcc | | 1 | 1( 791) 1 | 792( 139) 2 | | | | |
| Ban I | g/gyrcc | | 1 | 1( 619) 1 | 620( 311) 2 | | | | |
| Ban II | grgcy/c | | 1 | 1( 718) 1 | 719( 212) 2 | | | | |
| Bbv II | gaagac | 2/6 | 1 | 1( 781) 1 | 782( 149) 2 | | | | |
| BsaA I | yac/gtr | | 1 | 1( 492) 1 | 493( 438) 2 | | | | |
| Bsp1286 I | gdgch/c | | 1 | 1( 718) 1 | 719( 212) 2 | | | | |
| Bsr I | actgg | 1/-1 | 1 | 1( 449) 2 | 450( 481) 1 | | | | |
| BstX I | ccannnnn/ntgg | | 1 | 1( 866) 1 | 867( 44) 2 | | | | |
| Eag I | c/ggccg | | 1 | 1( 809) 1 | 810( 121) 2 | | | | |
| Fnu4H I | gc/ngc | | 1 | 1( 808) 1 | 809( 122) 2 | | | | |
| Fok I | ggatg | 9/13 | 1 | 1( 756) 1 | 757( 174) 2 | | | | |
| Gdi II | yggccg | -5/-1 | 1 | 1( 809) 1 | 810( 121) 2 | | | | |
| Gsu I | ctggag | 16/14 | 1 | 1( 746) 1 | 747( 184) 2 | | | | |
| HgiA I | gwgcw/c | | 1 | 1( 718) 1 | 719( 212) 2 | | | | |
| HinC II | gty/rac | | 1 | 1( 136) 2 | 137( 794) 1 | | | | |
| Hph I | ggtga | 8/7 | 1 | 1( 518) 1 | 519( 412) 2 | | | | |
| Mae I | c/tag | | 1 | 1( 154) 2 | 155( 776) 1 | | | | |
| Mbo II | gaaga | 8/7 | 1 | 1( 781) 1 | 782( 149) 2 | | | | |
| Mme I | tccrac | 20/18 | 1 | 1( 119) 2 | 120( 811) 1 | | | | |
| Mse I | t/taa | | 1 | 1( 161) 2 | 162( 769) 1 | | | | |
| Nco I | c/catgg | | 1 | 1( 514) 1 | 515( 416) 2 | | | | |
| Nde I | ca/tatg | | 1 | 1( 387) 2 | 388( 543) 1 | | | | |
| Nsi I | atgca/t | | 1 | 1( 904) 1 | 905( 26) 2 | | | | |
| Nsp7524 I | r/catgy | | 1 | 1( 906) 1 | 907( 24) 2 | | | | |
| NspB II | cmg/ckg | | 1 | 1( 806) 1 | 807( 124) 2 | | | | |
| NspH I | rcatg/y | | 1 | 1( 906) 1 | 907( 24) 2 | | | | |
| Sac I | gagct/c | | 1 | 1( 718) 1 | 719( 212) 2 | | | | |
| Sac II | ccgc/gg | | 1 | 1( 806) 1 | 807( 124) 2 | | | | |
| SfaN I | gcatc | 5/9 | 1 | 1( 521) 1 | 522( 409) 2 | | | | |
| SnaB I | tac/gta | | 1 | 1( 492) 1 | 493( 438) 2 | | | | |
| Spe I | a/ctagt | | 1 | 1( 153) 2 | 154( 777) 1 | | | | |
| Sph I | gcatg/c | | 1 | 1( 906) 1 | 907( 24) 2 | | | | |
| Bcn I | ccs/gg | | 2 | 1( 788) 1 | 789( 24) 3 | 813( 118) 2 | | | |
| BsmA I | gtctc | 1/5 | 2 | 1( 583) 1 | 584( 166) 3 | 750( 181) 2 | | | |
| Dpn I | ga/tc | | 2 | 1( 740) 1 | 741( 56) 3 | 797( 134) 2 | | | |
| Dsa I | c/crygg | | 2 | 1( 514) 1 | 515( 292) 2 | 807( 124) 3 | | | |
| Eae I | wgg/ccw | | 2 | 1( 9) 3 | 10( 54) 2 | 64( 867) 1 | | | |
| Hga I | gacgc | 5/10 | 2 | 1( 671) 1 | 672( 80) 3 | 752( 179) 2 | | | |
| Hpa II | c/cgg | | 2 | 1( 788) 1 | 789( 24) 3 | 813( 118) 2 | | | |
| Mbo I | /gatc | | 2 | 1( 740) 1 | 741( 56) 3 | 797( 134) 2 | | | |
| Msc I | tgg/cca | | 2 | 1( 9) 3 | 10( 54) 2 | 64( 867) 1 | | | |
| Hsp I | c/cgg | | 2 | 1( 788) 1 | 789( 24) 3 | 813( 118) 2 | | | |
| Nci I | cc/sgg | | 2 | 1( 788) 1 | 789( 24) 3 | 813( 118) 2 | | | |
| Nla IV | ggn/ncc | | 2 | 1( 619) 1 | 620( 171) 2 | 791( 140) 3 | | | |
| Ple I | gagtc | 4/5 | 2 | 1( 564) 1 | 565( 310) 2 | 875( 56) 3 | | | |
| Sau3A I | /gatc | | 2 | 1( 740) 1 | 741( 56) 3 | 797( 134) 2 | | | |
| Ssp I | aat/att | | 2 | 1( 4) 3 | 5( 47) 2 | 52( 879) 1 | | | |
| Sty I | c/cwwgg | | 2 | 1( 514) 1 | 515( 378) 2 | 893( 38) 3 | | | |

| Enzyme | Site | | | | | | | |
|---|---|---|---|---|---|---|---|---|
| BstN I | cc/wgg | | 3 | 1( 243) 2 | 244( 193) 3 | 437( 309) 1 | 746( 185) 4 | |
| BstU I | cg/cg | | 3 | 1( 213) 2 | 214( 594) 1 | 808( 25) 4 | 833( 98) 3 | |
| Eae I | y/ggccr | | 3 | 1( 9) 4 | 10( 54) 3 | 64( 746) 1 | 810( 121) 2 | |
| EcoR II | /ccwgg | | 3 | 1( 243) 2 | 244( 193) 3 | 437( 309) 1 | 746( 185) 4 | |
| Hinf I | g/antc | | 3 | 1( 564) 1 | 565( 272) 2 | 837( 38) 4 | 875( 56) 3 | |
| Hnl I | cctc | 7/7 | 3 | 1( 702) 1 | 703( 71) 3 | 774( 30) 4 | 804( 127) 2 | |
| Sec I | c/cnngg | | 3 | 1( 514) 1 | 515( 292) 2 | 807( 86) 3 | 893( 38) 4 | |
| Aat II | gacgt/c | | 4 | 1( 275) 2 | 276( 53) 5 | 329( 83) 4 | 412( 186) 3 | |
|  |  |  |  | 598( 333) 1 |  |  |  | |
| Bgl I | gccnnnn/nggc | | 4 | 1( 238) 2 | 239( 122) 4 | 361( 71) 5 | 432( 371) 1 | |
|  |  |  |  | 803( 128) 3 |  |  |  | |
| Hae III | /gtnac | | 4 | 1( 216) 2 | 217( 87) 4 | 304( 349) 1 | 653( 201) 3 | |
|  |  |  |  | 854( 77) 5 |  |  |  | |
| Sau96 I | g/gncc | | 4 | 1( 237) 2 | 238( 193) 3 | 431( 361) 1 | 792( 92) 4 | |
|  |  |  |  | 884( 47) 5 |  |  |  | |
| Aha II | gr/cgyc | | 5 | 1( 275) 1 | 276( 53) 6 | 329( 83) 5 | 412( 186) 2 | |
|  |  |  |  | 598( 154) 4 | 752( 179) 3 |  |  | |
| Nla III | catg/ | | 5 | 1( 115) 3 | 116( 18) 6 | 134( 322) 2 | 456( 60) 4 | |
|  |  |  |  | 516( 392) 1 | 908( 23) 5 |  |  | |
| ScrF I | cc/ngg | | 5 | 1( 243) 2 | 244( 193) 3 | 437( 309) 1 | 746( 43) 5 | |
|  |  |  |  | 789( 24) 6 | 813( 118) 4 |  |  | |
| Hae III | gg/cc | | 6 | 1( 10) 7 | 11( 54) 5 | 65( 173) 3 | 238( 193) 2 | |
|  |  |  |  | 431( 380) 1 | 811( 73) 4 | 884( 47) 6 |  | |
| Mae II | a/cgt | | 8 | 1( 75) 6 | 76( 201) 2 | 277( 12) 9 | 289( 41) 8 | |
|  |  |  |  | 330( 83) 4 | 413( 81) 5 | 494( 105) 3 | 599( 258) 1 | |
|  |  |  |  | 857( 74) 7 |  |  |  | |
| Rsa I | gt/ac | | 8 | 1( 98) 4 | 99( 274) 1 | 373( 25) 9 | 398( 55) 6 | |
|  |  |  |  | 453( 33) 8 | 486( 51) 7 | 537( 157) 3 | 694( 169) 2 | |
|  |  |  |  | 863( 68) 5 |  |  |  | |

141 sites found

No Sites found for the following Restriction Endonucleases

| | | | | | |
|---|---|---|---|---|---|
| Acc I | gt/mkac | Dde I | c/tnag | Nru I | tcg/cga |
| Afl II | c/ttaag | Dra I | ttt/aaa | Pac I | ttaat/taa |
| Afl III | a/crygt | Dra III | cacnnn/gtg | PaeR7 I | c/tcgag |
| AlwN I | cagnnn/ctg | Drd I | gacnnnn/nngtc | PflM I | ccannnn/ntgg |
| Apa I | gggcc/c | Ear I | ctcttc 1/4 | Pml I | cac/gtg |
| ApaL I | g/tgcac | Eco47 III | agc/gct | PpuM I | rg/gwccy |
| Asp718 | g/gtacc | Eco57 I | ctgaag 16/14 | Pst I | ctgca/g |
| Ava I | c/ycgrg | EcoN I | cctnn/nnnagg | Pvu I | cgat/cg |
| Avr II | c/ctagg | EcoO109 I | rg/gnccy | Pvu II | cag/ctg |
| BamH I | g/gatcc | EcoR I | g/aattc | Rsr II | cg/gwccg |
| Bbe I | ggcgc/c | EcoR V | gat/atc | Sal I | g/tcgac |
| Bbv I | gcagc 8/12 | Esp I | gc/tnagc | Sca I | agt/act |
| Bcl I | t/gatca | Fsp I | tgc/gca | Sfi I | ggccnnnn/nggcc |
| Bgl II | a/gatct | Hae II | rgcgc/y | Sma I | ccc/ggg |
| Bsm I | gaatgc 1/-1 | HgiE II | accnnnnnnggt | Spl I | c/gtacg |
| BspH I | t/catga | Hha I | gcg/c | Stu I | agg/cct |
| BspM I | acctgc 4/8 | HinD III | a/agctt | Taq I | t/cga |
| BspM II | t/ccgga | HinP I | g/cgc | Tth111 I | gacn/nngtc |
| BssH II | g/cgcgc | Hpa I | gtt/aac | Tth111 II caarca 11/9 |  |
| BstB I | tt/cgaa | Kpn I | ggtac/c | Xba I | t/ctaga |
| BstE II | g/gtnacc | Mlu I | a/cgcgt | Xca I | gta/tac |
| BstY I | r/gatcy | Nae I | gcc/ggc | Xho I | c/tcgag |
| Bsu36 I | cc/tnagg | Nar I | gg/cgcc | Xcm I | ccannnnn/nnnntgg |
| Cfr10 I | r/ccggy | Nhe I | g/ctagc | Xma I | c/ccggg |
| Cla I | at/cgat | Not I | gc/ggccgc | Xmn I | gaann/nnttc |

FIG. 6C-10

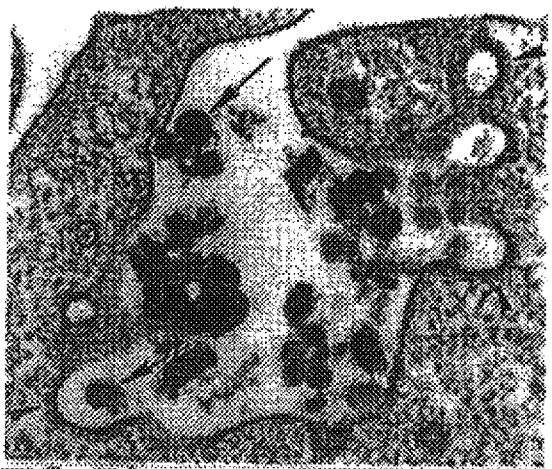
FIG. 7A
FIG. 7B
FIG. 7C
FIG. 7D
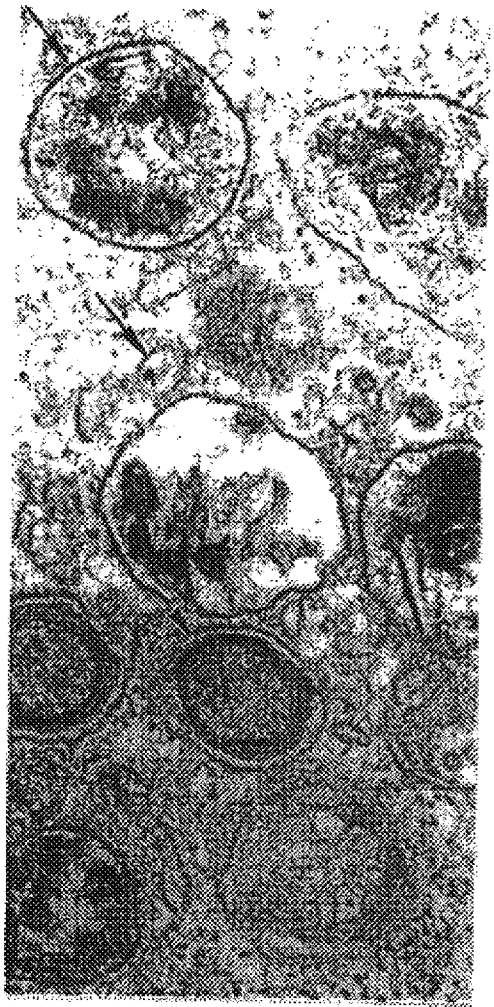
FIG. 7E
FIG. 7F

FIGURE 8C  Control

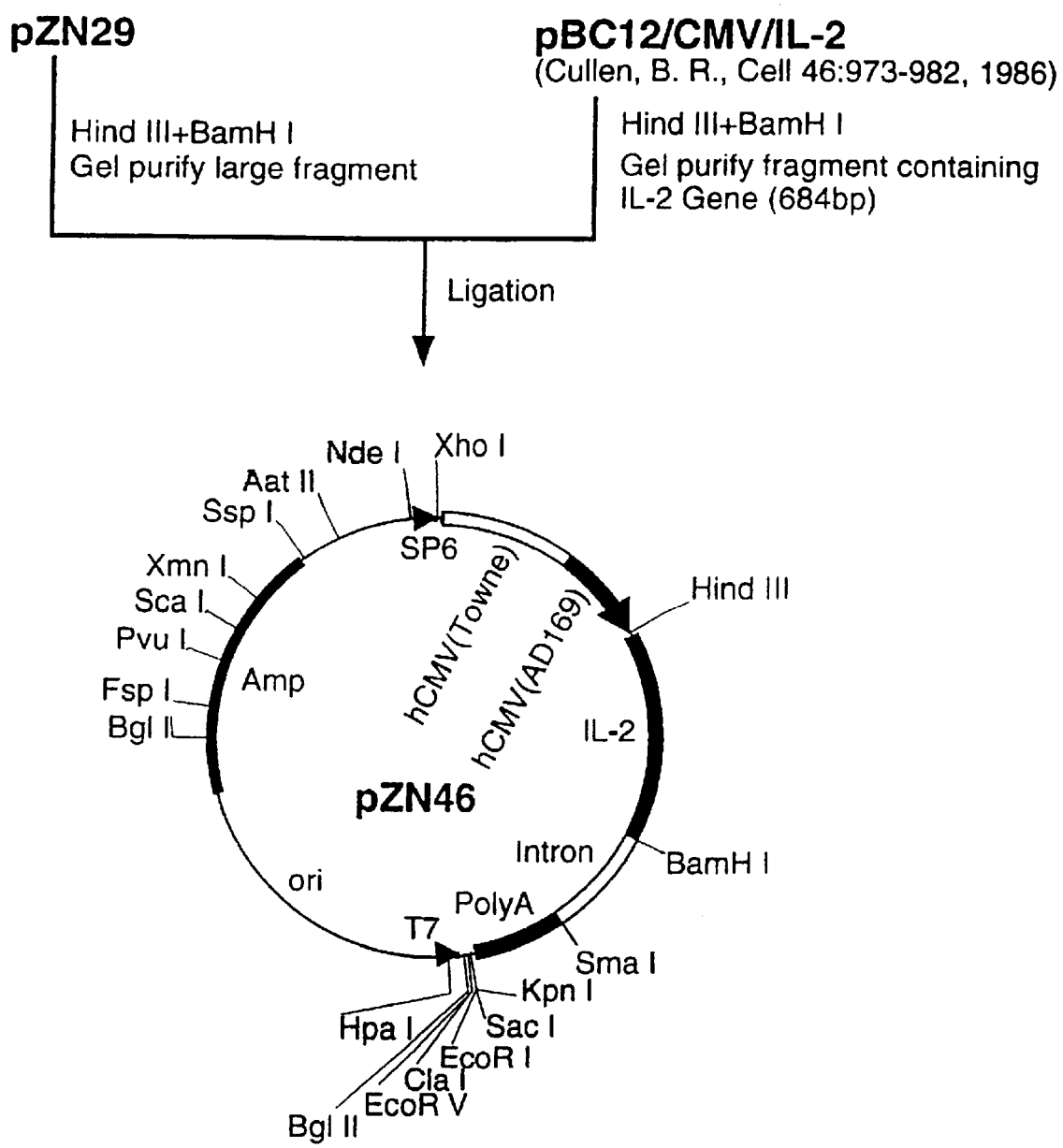
FIG. IOD

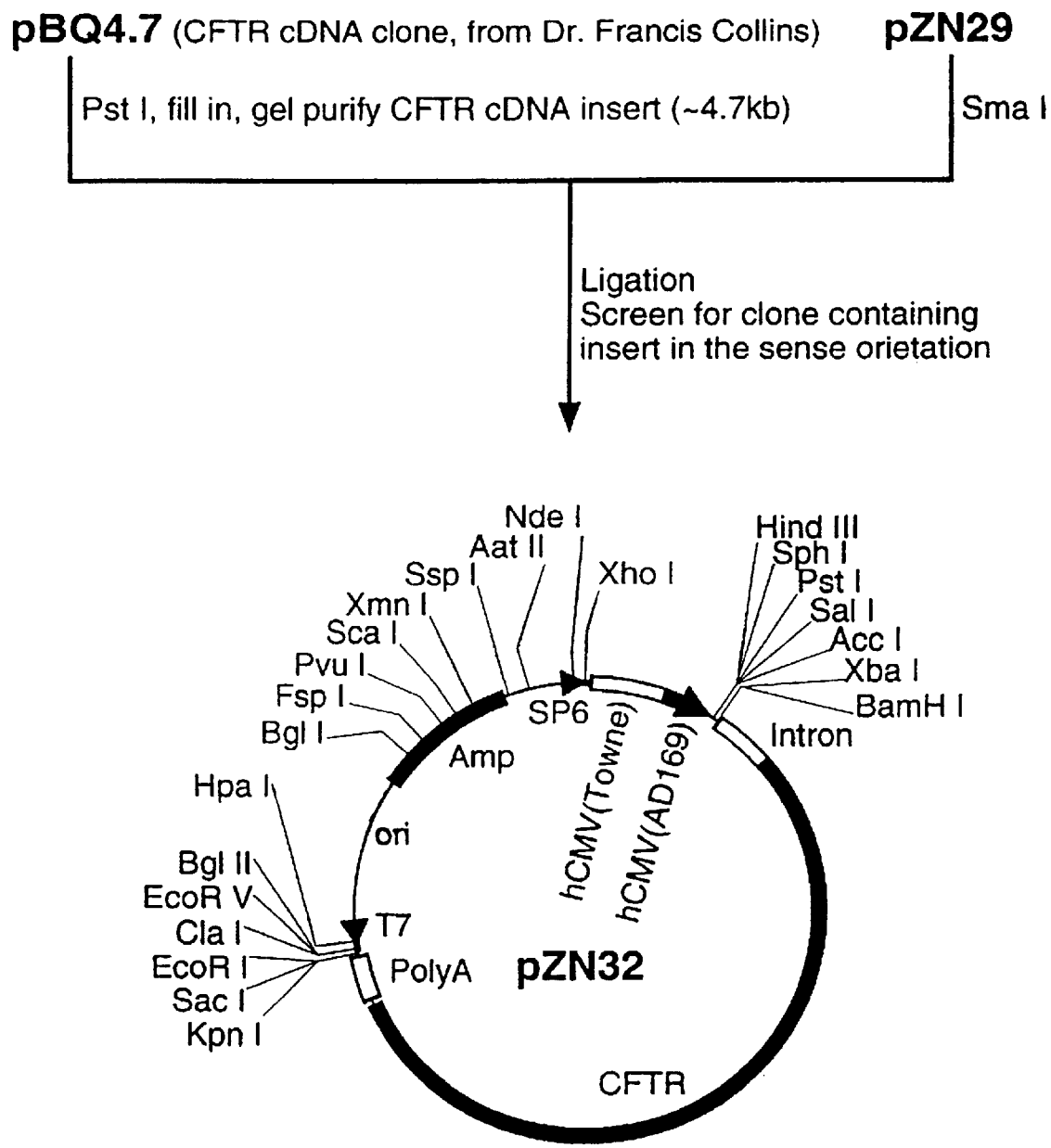
FIG. II

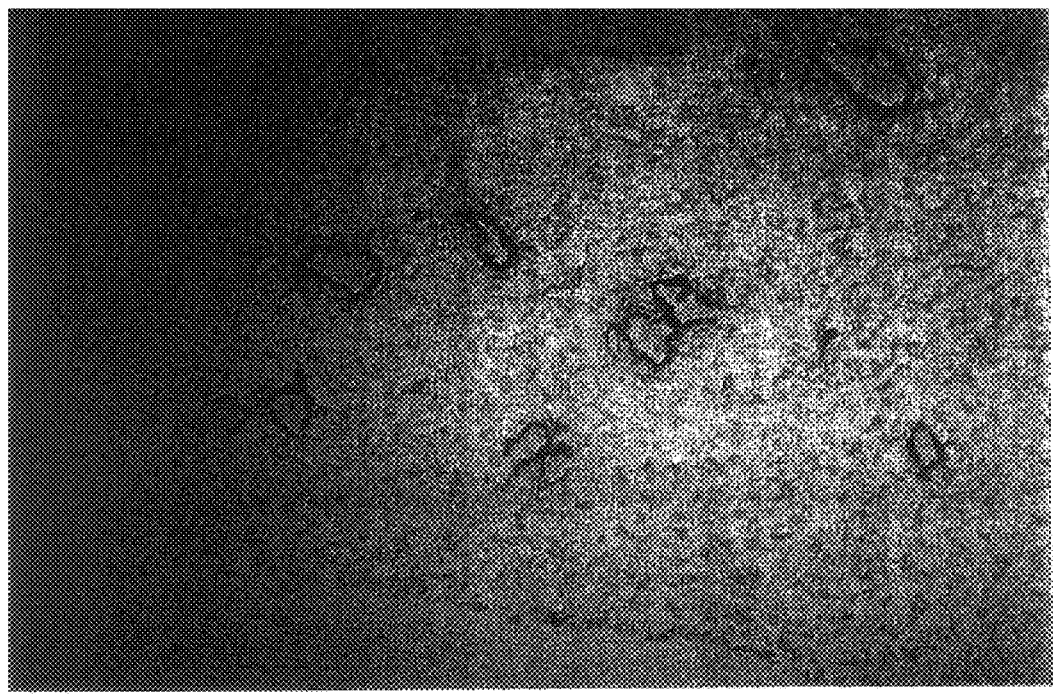
FIGURE 12A  50X
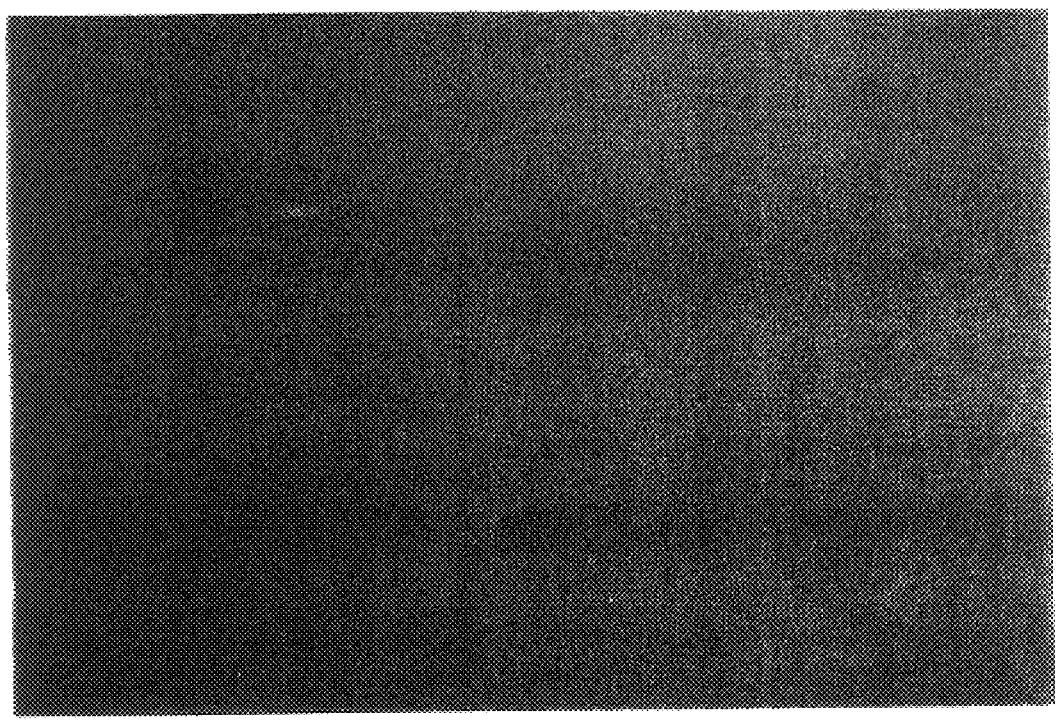
FIGURE 12B  Control 50X

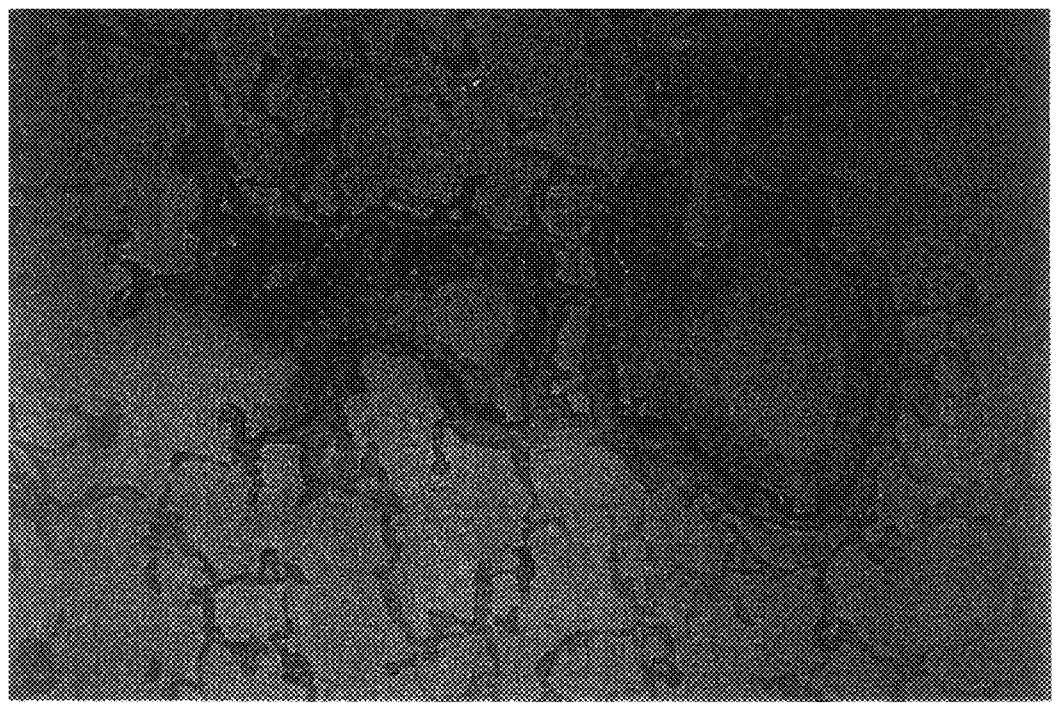
FIGURE 12C 100X
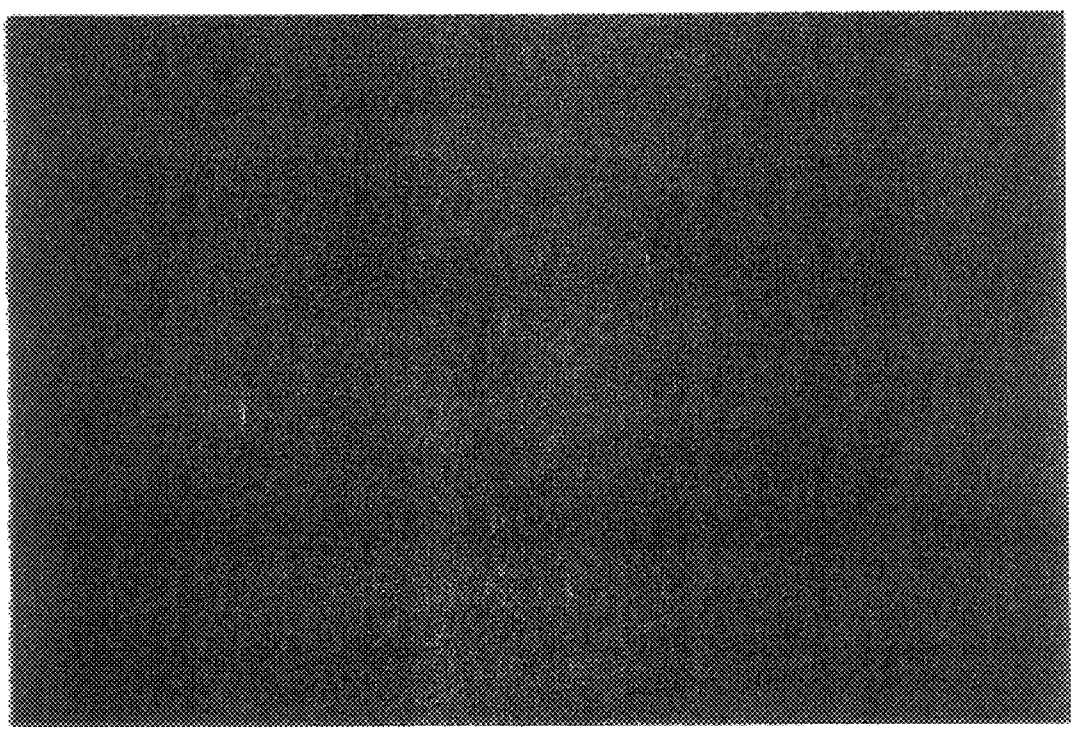
FIGURE 12D Control 100X

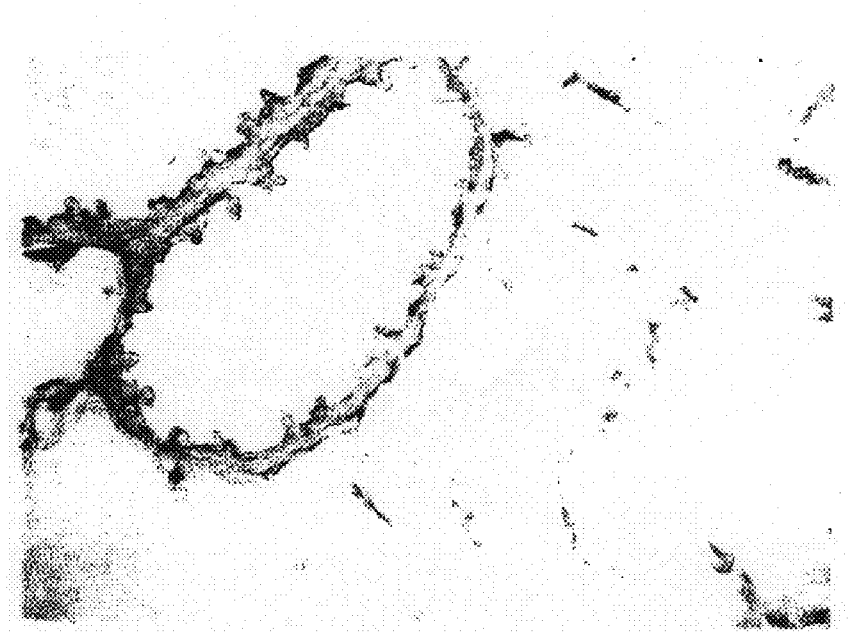
FIGURE 16C    Control

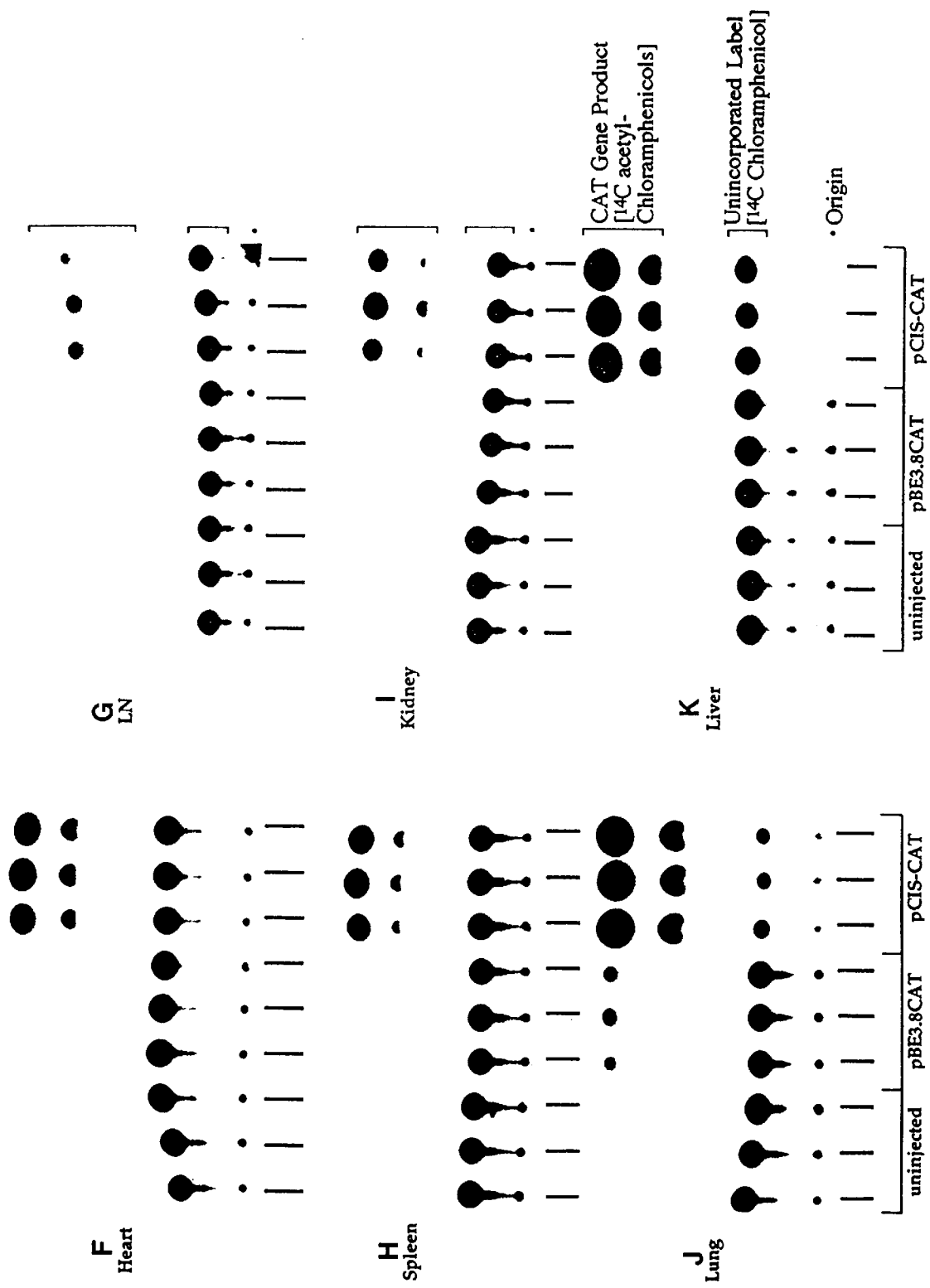
FIGURE 16(F-K)

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 616

(B) TYPE: nucleic acid
            (C) STRANDEDNESS: single
            (D) TOPOLOGY: linear (xi) SEQUENCE DESCRIPTION: SEQ ID NO: 1:

GGCGACCGCC CAGCGACCCC CGCCCGTTGA CGTCAATAGT GACGTATGTT CCCATAGTAA      60

CGCCAATAGG GACTTTCCAT TGACGTCAAT GGGTGGAGTA TTTACGGTAA ACTGCCTACT     120

TGGCAGTACA TCAAGTGTAT CATATGCCAA GTCCGCCCCC TATTGACGTC AATGACGGTA     180

AATGGCCCGC CTAGCATTAT GCCCAGTACA TGACCTTACG GGAGTTTCCT ACTTGGCAGT     240

ACATCTACGT ATTAGTCATC GCTATTACCA TGGTGATGCG GTTTTGGCAG TACACCAATG     300

GGCGTGGATA GCGGTTTGAC TCACGGGGAT TTCCAAGTCT CCACCCCATT GACGTCAATG     360

GGAGTTTGTT TTGGCACCAA AATCAACGGG ACTTTCCAAA ATGTCGTAAT AACCCCGCCC     420

CGTTGACGCA AATGGGCGGT AGGCGTGTAC GGTGGGAGGT CTATATAGCA GAGCTCGTTT     480

AGTGAACCGT CAGATCGCCT GGAGACGCCA TCCACGCTGT TTTGACCTCC ATAGAAGACA     540

CCGGGACCGA TCCAGCCTCC GCGGCCGGGA ACGGTGCATT GGAACGCGGA TTCCCCGTGC     600

CAAGAGTGAC GTAAGT                                                    616

(2) INFORMATION FOR SEQ ID NO: 2:

(i) SEQUENCE CHARACTERISTICS:
            (A) LENGTH: 930
            (B) TYPE: nucleic acid
            (C) STRANDEDNESS: single
            (D) TOPOLOGY: linear (xi) SEQUENCE DESCRIPTION: SEQ ID NO: 2:

AATCAATATT GGCCATTAGC CATATTATTC ATTGGTTATA TAGCATAAAT CAATATTGGC      60

TATTGGCCAT TGCATACGTT GTATCCATAT CATAATATGT ACATTTATAT TGGCTCATGT     120

CCAACATTAC CGCCATGTTG ACATTGATTA TTGACTAGTT ATTAATAGTA ATCAATTACG     180

GGGTCATTAG TTCATAGCCC ATATATGGAG TTCCGCGTTA CATAACTTAC GGTAAATGGC     240

CCGCCTGGCT GACCGCCCAA CGACCCCCGC CCATTGACGT CAATAATGAC GTATGTTCCC     300

ATAGTAACGC CAATAGGGAC TTTCCATTGA CGTCAATGGG TGGAGTATTT ACGGTAAACT     360

GCCCACTTGG CAGTACATCA AGTGTATCAT ATGCCAAGTA CGCCCCCTAT TGACGTCAAT     420

GACGGTAAAT GGCCCGCCTG GCATTATGCC CAGTACATGA CCTTATGGGA CTTTCCTACT     480

TGGCAGTACA TCTACGTATT AGTCATCGCT ATTACCATGG TGATGCGGTT TTGGCAGTAC     540

ATCAATGGGC GTGGATAGCG GTTTGACTCA CGGGGATTTC CAAGTCTCCA CCCCATTGAC     600

GTCAATGGGA GTTTGTTTTG CACCAAAAT CAACGGGACT TTCCAAAATG TCGTAACAAC      660

TCCGCCCCAT TGACGCAAAT GGGCGGTAGG CGTGTACGGT GGGAGGTCTA TATAAGCAGA     720

GCTCGTTTAG TGAACCGTCA GATCGCCTGG AGACGCCATC CACGCTGTTT TGACCTCCAT     780

AGAAGACACC GGGACCGATC CAGCCTCCGC GGCCGGGAAC GGTGCATTGG AACGCGGATT     840

CCCCGTGCCA AGAGTGACGT AAGTACCGCC TATAGAGTCT ATAGGCCCAC CCCCTTGGCT     900

TCTTATGCAT GCTATACTGT TTTTGGCTTG                                     930

(2) INFORMATION FOR SEQ ID NO: 3:

(i) SEQUENCE CHARACTERISTICS:
            (A) LENGTH: 616
            (B) TYPE: nucleic acid
            (C) STRANDEDNESS: single
            (D) TOPOLOGY: linear (xi) SEQUENCE DESCRIPTION: SEQ ID NO: 3:

```
GGCGACCGCC CAGCGACCCC CGCCCGTTGA CGTCAATAGT GACGTATGTT CCCATAGTAA      60

CGCCAATAGG GACTTTCCAT TGACGTCAAT GGGTGGAGTA TTTACGGTAA ACTGCCCACT     120

TGGCAGTACA TCAAGTGTAT CATATGCCAA GTCCGCCCCC TATTGACGTC AATGACGGTA     180

AATGGCCCGC CTAGCATTAT GCCCAGTACA TGACCTTACG GGAGTTTCCT ACTTGGCAGT     240

ACATCTACGT ATTAGTCATC GCTATTACCA TGGTGATGCG GTTTTGGCAG TACACCAATG     300

GGCGTGGATA GCGGTTTGAC TCACGGGGAT TTCCAAGTCT CCACCCCATT GACGTCAATG     360

GGAGTTTGTT TTGGCACCAA AATCAACGGG ACTTTCCAAA ATGTCGTAAT AACCCCGCCC     420

CGTTGACGCA AATGGGCGGT AGGCGTGTAC GGTGGGAGGT CTATATAAGCA GAGCTCGTTT    480

AGTGAACCGT CAGATCGCCT GGAGACGCCA TCCACGCTGT TTTGACCTCC ATAGAAGACA     540

CCGGGACCGA TCCAGCCTCC GCGGCCGGGA ACGGTGCATT GGAACGCGGA TTCCCCGTGC     600

CAAGAGTGAC GTAAGT                                                    616
```

(2) INFORMATION FOR SEQ ID NO: 4:

(i) SEQUENCE CHARACTERISTICS:
        (A) LENGTH: 930
        (B) TYPE: nucleic acid
        (C) STRANDEDNESS: single
        (D) TOPOLOGY: linear (xi) SEQUENCE DESCRIPTION: SEQ ID NO: 4:

```
AATCAATATT GGCCATTAGC CATATTATTC ATTGGTTATA TAGCATAAAT CAATATTGGC      60

TATTGGCCAT TGCATACGTT GTATCCATAT CATAATATGT ACATTTATAT TGGCTCATGT     120

CCAACATTAC CGCCATGTTG ACATTGATTA TTGACTAGTT ATTAATAGTA ATCAATTACG     180

GGGTCATTAG TTCATAGCCC ATATATGGAG TTCCGCGTTA CATAACTTAC GGTAAATGGC     240

CCGCCTGGCT GACCGCCCAA CGACCCCCGC CCATTGACGT CAATAATGAC GTATGTTCCC     300

ATAGTAACGC CAATAGGGAC TTTCCATTGA CGTCAATGGG TGGAGTATTT ACGGTAAACT     360

GCCCACTTGG CAGTACATCA AGTGTATCAT ATGCCAAGTA CGCCCCCTAT TGACGTCAAT     420

GACGGTAAAT GGCCCGCCTG GCATTATGCC CAGTACATGA CCTTATGGGA CTTTCCTACT     480

TGGCAGTACA TCTACGTATT AGTCATCGCT ATTACCATGG TGATGCGGTT TTGGCAGTAC     540

ATCAATGGGC GTGGATAGCG GTTTGACTCA CGGGGATTTC CAAGTCTCCA CCCCATTGAC     600

GTCAATGGGA GTTTGTTTTG GCACCAAAAT CAACGGGACT TTCCAAAATG TCGTAACAAC     660

TCCGCCCCAT TGACGCAAAT GGGCGGTAGG CGTGTACGGT GGGAGGTCTA TATAAGCAGA     720

GCTCGTTTAG TGAACCGTCA GATCGCCTGG AGACGCCATC CACGCTGTTT TGACCTCCAT     780

AGAAGACACC GGGACCGATC CAGCCTCCGC GGCCGGGAAC GGTGCATTGG AACGCGGATT     840

CCCCGTGCCA AGAGTGACGT AAGTACCGCC TATAGAGTCT ATAGGCCCAC CCCCTTGGCT     900

TCTTATGCAT GCTATACTGT TTTTGGCTTG                                     930
```

METHODS AND COMPOSITIONS FOR IN VIVO GENE THERAPY

This application is a continuation and claims the benefit of U.S. patent application Ser. No. 08/464,899, filed Jan. 22, 1996, which is a National Stage Application of PCT/US93/05366, filed Jun. 4, 1993, which is a continuation-in-part of U.S. patent application Ser. No. 07/992,687, filed Dec. 17, 1992, (now abandoned) and which is also a continuation-in-part of U.S. patent application Ser. No. 07/927,200, filed Aug. 6, 1992, (now abandoned) and which is also a continuation-in-part of U.S. patent application Ser. No. 07/894,498, filed Jun. 4, 1992, (now abandoned), the disclosures of which are incorporated by reference; this application is also a continuation-in-part and claims the benefit of U.S. patent application Ser. No. 08/256,004, filed Aug. 22, 1994, (now U.S. Pat. No. 6,001,644) which was a National Stage application of PCT/US92/11004, filed Dec. 17, 1992, which is a CIP of application U.S. Ser. No. 07/972,135, filed Nov. 5, 1992, now U.S. Pat. No. 5,858,784, which is a CIP of application U.S. Ser. No. 07/809,291, filed Dec. 17, 1991, now abandoned. PCT/US92/11004, filed Dec. 17, 1992, is also a CIP of application U.S. Ser. No. 07/927,200, filed Aug. 6, 1992, now abandoned, which is a CIP of application U.S. Ser. No. 07/894,498, filed Jun. 4, 1992, now abandoned.

INTRODUCTION

1. Technical Field

The present invention relates to methods and compositions for systemic introduction of exogenous genetic material into mammalian, particularly human, cells in vivo.

2. Background

An ever-expanding array of genes for which abnormal expression is associated with life-threatening human diseases is being cloned and identified. The ability to express such cloned genes in humans will ultimately permit the prevention and/or cure of many important human diseases, diseases which now either are treated poorly or are untreatable by currently available therapies. As an example, in vivo expression of cholesterol-regulating genes, genes which selectively block the replication of HIV, or of tumor-suppressing genes in human patients should dramatically improve treatment of heart disease, HIV, and cancer, respectively. However, currently available gene delivery strategies have been unable to produce either a high level of or generalized transgene expression in vivo in a wide variety of tissues after systemic administration to a mammalian host. This inability has precluded the development of effective gene therapy for most human diseases.

Approaches to gene therapy include both different goals and different means of achieving those goals. The goals generally include gene replacement, gene correction and gene augmentation. In gene replacement, a mutant gene sequence is specifically removed from the genome and replaced with a normal, functional gene. In gene correction, a mutant gene sequence is corrected without any additional changes in the target genome. In gene augmentation, the expression of mutant genes in defective cells is modified by introducing foreign normal genetic sequences.

The means to reach the above goals used by others, have included "ex vivo" transfection of a target cell followed by introduction of the transformed cells into a suitable organ in the host mammal. Ex vivo techniques include transfection of cells in vitro with either naked DNA or DNA liposome conjugates, followed by introduction into a host organ ("ex vivo" gene therapy). The criteria for a suitable target organ or tissue include that the target organ or tissue is easily accessible, that it can be manipulated in vitro, that it is susceptible to genetic modification methods and ideally, it should contain either non-replicating cells or cycling stem cells to perpetuate a genetic correction. Further, it should be possible to reimplant the genetically modified cells into the organism in a functional and stable form. Exemplary of a target organ which meets these criteria is the mammalian bone marrow. A further criterion for ex vivo gene therapy, if for example a retroviral vector is used, is that the cells be pre-mitotic; post-mitotic cells are refractory to infection with retroviral vectors. Although this has not been reported, in some instances it may be possible to transfect cells from other than the target organ or tissue using ex vivo gene therapy if the corrective gene product can be secreted and exert the desired effect on/in the target cell following circulation in blood or other body fluids.

There are several drawbacks to ex vivo therapy; for example, if only differentiated, replicating cells are infected, the newly introduced gene function will be lost as those cells mature and die. Ex vivo approaches also can be used to transfect only a limited number of cells and cannot be used to transfect cells which are not removed first from the body. The above methods generally involve integration of new genetic material into the cell genome and thus constitute permanent changes.

Liposomes have been used effectively, particularly to introduce drugs, radiotherapeutic agents, enzymes, viruses, transcription factors and other cellular effectors into a variety of cultured cell lines and animals. The agent to be introduced is typically entrapped within the liposome, or lipid vesicle, or the agent may be bound to the outside of the vesicle. Successful clinical trials examining the effectiveness of liposome-mediated drug delivery have been completed. Several strategies have been devised to increase the effectiveness of liposome-mediated drug delivery by targeting liposomes to specific tissues and specific cell types. However, while the basic methodology for using liposome-mediated vectors is well developed, the technique has not been perfected for liposome-based transfection vectors for in vivo gene therapy.

In vivo expression of transgenes as reported by others has been restricted to injection of transgenes directly into a specific tissue, such as direct intratracheal, intramuscular or intraarterial injection of naked DNA or of DNA-cationic liposome complexes, or to ex vivo transfection of host cells, with subsequent reinfusion. The expression is low and generally has been limited to one tissue, typically the tissue that was injected (for example muscle); liver or lung where iv injection has been used; or lung where intratracheal injection has been used, and less than 1% of all cells within these tissues were transfected. In some cases, transfection of cells has been obtained in tissues afferent to the site of intravenous administration.

Currently available gene delivery strategies consistently have failed to produce a high level and/or generalized transgene expression in vivo. It therefore would be of interest to develop compositions and delivery methods for in vivo gene therapy that provide for a high level of transcription of the transgene and/or expression in a variety of cell and tissue types for the in vivo treatment, prevention, or palliation of numerous human diseases. Also of interest, is the use of gene modulation as an alternate means of gene therapy. In gene modulation, expression of an already expressed gene is increased by introducing exogenous normal genetic sequences and decreased by introducing antisense genes or gene fragments, or by introducing vectors that can produce ribozymes that can cleave specific mRNAs. Gene modulation can also be achieved by the introduction of exogenous normal genetic sequences that code for proteins that modulate the extent of gene expression, or affect the processing, assembly or secretion of gene products.

Relevant Literature

A large number of publications relate to in vivo and ex vivo transfection of mammals. In some cases, only transcription of a transgene has been achieved, in others, the data appear to show only a low level of expression and/or expression in a limited number of tissues or cell types. The following are examples of the publications in this area.

A variety of approaches for introducing functional new genetic material into cells, both in vitro and in vivo have been attempted (Friedmann, (1989) Science, 244:1275–1281). These approaches include integration of the gene to be expressed into modified retroviruses (Friedmann, (1989) supra; Rosenberg, (1991) Cancer Research, 51(18), Suppl.: 5074S–5079S); integration into non-retrovirus vectors (Rosenfeld, et al., (1992) Cell, 68:143–155; Rosenfeld, et al., (1991) Science, 252:431–434); or delivery of a transgene linked to a heterologous promoter-enhancer element via liposomes (Friedmann, (1989), supra; Brigham, et al., (1989) Am. J. Med. Sci., 298:278–281; Nabel, et al., (1990) Science, 249:1285–1288; Hazinski, et al., (1991) Am. J. Resp. Cell Molec. Biol., 4:206–209; and Wang and Huang, (1987) Proc. Natl. Acad. Sci. (USA), 84:7851–7855); coupled to ligand-specific, cation-based transport systems (Wu and Wu, (1988) J. Biol. Chem., 263:14621–14624) or the use of naked DNA expression vectors (Nabel et al., (1990), supra); Wolff et al., (1990) Science, 247:1465–1468). Direct injection of transgenes into tissue produces only localized expression (Rosenfeld, (1992) supra); Rosenfeld et al., (1991) supra; Brigham et al., (1989) supra; Nabel, (1990) supra; and Hazinski et al., (1991) supra). The Brigham et al. group (Am. J. Med. Sci., (1989) 298:278–281 and Clinical Research, (1991) 39 (abstract)) have reported in vivo transfection only of lungs of mice following either intravenous or intratracheal administration of a DNA liposome complex. An example of a review article of human gene therapy procedures is: Anderson, (1992) Science 256:808–813.

PCT/US90/01515 (Felgner et al.) is directed to methods for delivering a gene coding for a pharmaceutical or immunogenic polypeptide to the interior of a cell of a vertebrate in vivo. Expression of the transgenes is limited to the tissue of injection. PCT/US90/05993 (Brigham) is directed to a method for obtaining expression of a transgene in mammalian lung cells following either iv or intratracheal injection of an expression construct. PCT 89/02469 and PCT 90/06997 are directed to ex vivo gene therapy, which is limited to expressing a transgene in cells that can be taken out of the body such as lymphocytes. PCT 89/12109 is likewise directed to ex vivo gene therapy. PCT 90/12878 is directed to an enhancer which provides a high level of expression both in transformed cell lines and in transgenic mice using ex vivo transfection. PCT/US92/08806 is directed to particle-mediated transformation of mammalian unattached cells. EP application 91301819.8 is directed to the use of recombinant techniques to produce cystic fibrosis transmembrane conductance regulator (CFTR).

SUMMARY OF THE INVENTION

Methods and compositions are provided for introduction of a transgene into a plurality of mammalian tissues in vivo. The method includes the step of incorporating a transfection cassette comprising a nucleotide sequence of interest into a largely non-integrating plasmid and introducing the plasmid into a mammalian host, other than by directly introducing it into a specific tissue. The transfection cassette comprises as operably joined components, a transcriptional and initiation regulatory region, a nucleic acid sequence of interest, and a transcriptional termination regulatory region, wherein said regulatory regions are functional in the cells of a mammalian host, and wherein said nucleic acid sequence of interest is free of introns. Optionally, the transcriptional cassette is complexed with a cationic lipid carrier. The method finds use to modulate the phenotype of mammalian cells.

DESCRIPTION OF THE DRAWINGS

FIG. 1A shows photomicrographs of sections of mouse lung from a mouse injected with a transfection cassette, or FIG. 1B a control mouse. The photomicrograph in 1A shows a section of mouse lung 48 hours following iv injection of pZN27:DDAB:Cholesterol expression vector-cationic lipid carrier complexes. The plasmid contained sequences for the expression of CAT (chloramphenicol acyl transferase). The lipid carrier composition was 1 to 1 molar DDAB:Cholesterol. The carrier: plasmid ratio was 5 nmoles cationic lipid to 1 $\mu$g DNA. A dose of 100 $\mu$g DNA was injected per mouse. This field shows alveoli and alveolar lining cells, the majority (50–70%) of which stain red positively for the presence of CAT protein when probed with anti-CAT antibody and visualized using alkaline phosphatase (indicated by arrows). The treated animals' lungs stain uniformly with diffuse involvement of alveolar and vascular endothelial cells. Airway epithelial staining is also seen indicating airway cells are also transfected. The CAT protein normally is not present in mammalian cells and therefore the presence of CAT protein in these cells indicates that they have been transfected in vivo. The photomicrograph in 1B shows a section of mouse lung from a control animal treated with iv-injected lipid carrier only, and probed with anti-CAT antibody. Cells do not show significant staining, although low-level background staining is detectable in some alveolar macrophages (indicated by arrows), which possess endogenous alkaline phosphatase activity.

FIG. 2A shows a phase contrast micrograph of mouse T lymphocytes isolated 48 hours after intraperitoneal (ip) injection of DNA-cationic lipid carrier complexes. Lipid carriers were DDAB:DOPE, 1 to 1 molar. DNA-cationic lipid carrier complexes were 1 mg pCIS-CAT with 1 $\mu$mole cationic lipid. 1 mg DNA was injected ip. Cells were incubated with anti CAT mouse monoclonal antibody, followed by Texas red-conjugated goat anti mouse IgG. FIG. 2B shows a fluorescence micrograph of the same field showing that essentially all T lymphocytes present removed from the treated animal were stained red by immunofluorescence demonstrating expression of the transfected CAT gene following ip injection of DNA/cationic lipid carrier complexes FIG. 2C shows a phase contrast micrograph of T lymphocytes isolated from an uninjected control mouse. FIG. 2D shows a fluorescence micrograph of the same field, showing that there is no CAT gene expression in these lymphocytes from control animals.

FIG. 3A shows hematopoietic bone marrow-derived cells from a mouse treated with a DNA:lipid carrier complex DDAB:Cholesterol:pZN51 intravenously 48 hours earlier. Cells were stained for CAT protein as in FIG. 1. The photomicrograph shows that approximately 70 percent of the bone marrow-derived cells, including primitive or blast cells are stained red (blast cell indicated by arrow) and are transfected in vivo. Lipid carriers were 1:1 DDAB:Cholesterol. DNA:cationic lipid ratio was 1 µg of DNA to 5 nmoles cationic lipid. 100 µg of DNA was injected iv into each mouse. FIG. 3B shows isolated bone marrow cells from an untreated control mouse. The photomicrograph shows no red staining indicating no CAT gene expression in untreated animals.

In FIG. 4A is shown a phase contrast micrograph of freshly isolated human CD4$^+$ T lymphocytes 48 hours after transfection. FIG. 4B shows a fluorescence micrograph of the same field which demonstrates that essentially 100% of the T lymphocytes stain positively for CAT protein, i.e., they have been transfected.

FIG. 7 (panels a–f) shows electron micrographs which demonstrates that cationic lipid carrier: DNA complexes (DOTMA:DOPE:pRSV-CAT) are internalized by CV-1 (African Green Monkey Kidney) cells via classical receptor-mediated endocytosis following binding to cell surface receptors. For construction of pRSVCAT see Gorman et al., (1982) *Proc. Nat. Acad. Sci. USA* 79:6777–6781. Lipid carriers were 1:1 DOTMA:DOPE. 20 µg DNA were complexed with 20 nmoles cationic lipid, and added to 2×10$^6$ cells. The arrows in panel (a) show particles binding to clathrin-coated pits; panel (b), the particles that have been ingested and are present in endosomes.

FIGS. 8A–8C show photomicrographs of a histochemical analysis of lungs from B-16 melanoma-bearing animals which received an intravenous injection of CMV-CAT cationic lipid carrier:DNA complexes. Lipid carriers were DOTAP:Cholesterol, 1 to 1 molar ratio. Cationic lipid: DNA ratio was 6 nanomoles: 1 µg DNA. The plasmid used was pZN20 (see FIG. 5). 100 µg DNA was injected per mouse. The immunohistochemical analysis for CAT protein revealed intense red staining of many focal parenchymal tumors (FIG. 8A indicated by arrows) and tumor emboli within blood vessels (FIG. 8B indicated by arrows), indicating that large numbers of B16 melanoma tumor cells in the lung, as well as blood-borne metastases, are transfected after iv injection. FIG. 8C shows that in tissue from B16 melanoma-bearing mice which did not receive an injection of DNA-lipid carrier complexes, no CAT protein is present in the surrounding normal lung or in any of the lung tumor cells.

FIGS. 10A–10D show the construction of plasmid pZN46, encoding human IL-2.

FIG. 11 shows the construction of plasmid pZN32, encoding human CFTR.

FIGS. 12A–12E shows photomicrographs of immunohistochemically stained (for CFTR protein) frozen sections of lung tissue from mice treated by intravenous administration of either pZN32:cationic lipid carrier complexes or lipid carrier alone (control mice). FIGS. 12A, 12C, and 12E are lung sections from mice treated with DNA lipid carrier complexes at 50×, 100×, and 250× magnification, respectively. FIGS. 12B and 12D are lung sections from control mice at 50× and 100× magnification show that there is no detectable CFTR expression in lungs of control mice. Lipid carriers were 1 to 1 molar DDAB:Cholesterol (SUV). Lipid carrier-DNA complexes were 5 nanomoles cationic lipid to 1 µg DNA. 100 µg DNA was injected per mouse. Animals were sacrificed 24 hrs after injection. The figures show that >70% of both airways and airway lining cells stain intensely red, indicating that they are expressing the CFTR gene.

FIG. 14 shows the construction of plasmids pZN60, pZN61, pZN62 and pZN63, all encoding CAT.

FIGS. 16A–16E show photomicrographs of frozen lung section that have been immunohistochemically stained for CAT protein. Mice were injected iv by tail vein with pZN27 (16A) which shows positive red staining for CAT is endothelial, alveolar and airway cells within the lung. In contrast, liposome complexes of the CAT gene linked to the natural CFTR promoter (pBE3.8CAT) showed CAT expression primarily in airway epithelial cells (16B). A lung section from an uninjected control animal did not show red staining, indicating no CAT expression in untransfected cells (16C). FIG. 16D shows a high magnification photomicrograph of alveoli from a pZN27 treated mouse, and shows a high level of positive red staining for CAT gene product in both alveolar and epithelial cells. FIG. 16E shows a high magnification photomicrograph of alveoli from a pBE3.8CAT injected mouse, and shows no significant CAT gene expression in either alveolar or endothelial cells. One hundred µg of plasmid was injected iv complexed with DDAB:Cholesterol as SUVs. Animals were sacrificed after 24 hrs.

FIGS. 16F–16K show autoradiographs of the thin layer chromatographs of CAT activity in heart (16F), lymph nodes (16G) spleen (16H), kidney (16I), lung (16J), and liver (16K) in tissue from uninjected mice (lanes 1–3), mice injected IV with pBE3.8CAT (Chou, et al., (1991) *J. Biol. Chem.*, 266:24471–24476 (lanes 4–6), or mice injected with pCIS-CAT (lanes 7–9). Lipid carriers were DDAB:Cholesterol, 1:1 SUV (1 µg DNA to 5 nmoles cationic lipid; 100 µg injected per mouse.

DESCRIPTION OF THE SPECIFIC EMBODIMENTS

Figure 5A:
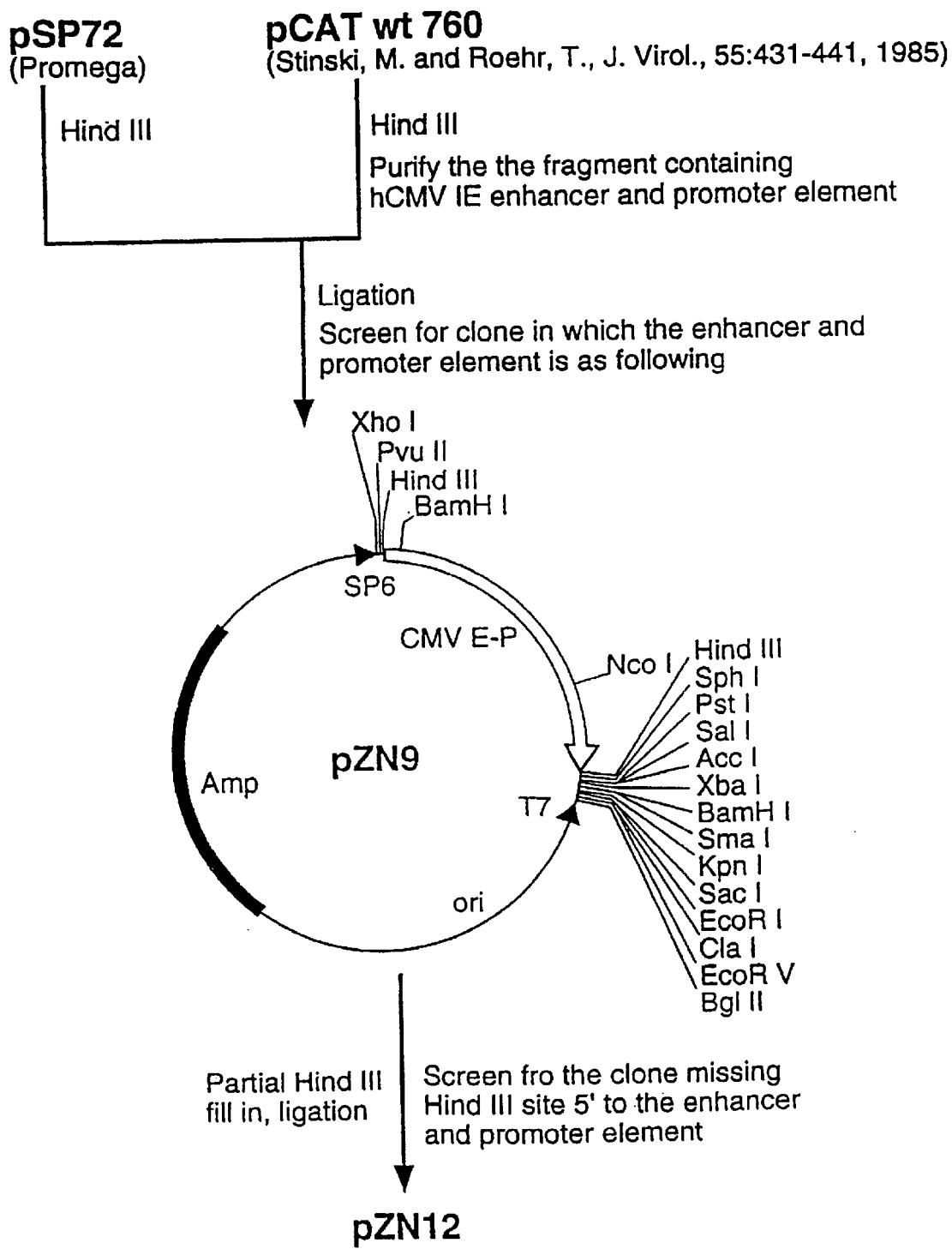
FIG. 5 shows construction of plasmid pZN20.
Figure 5B:
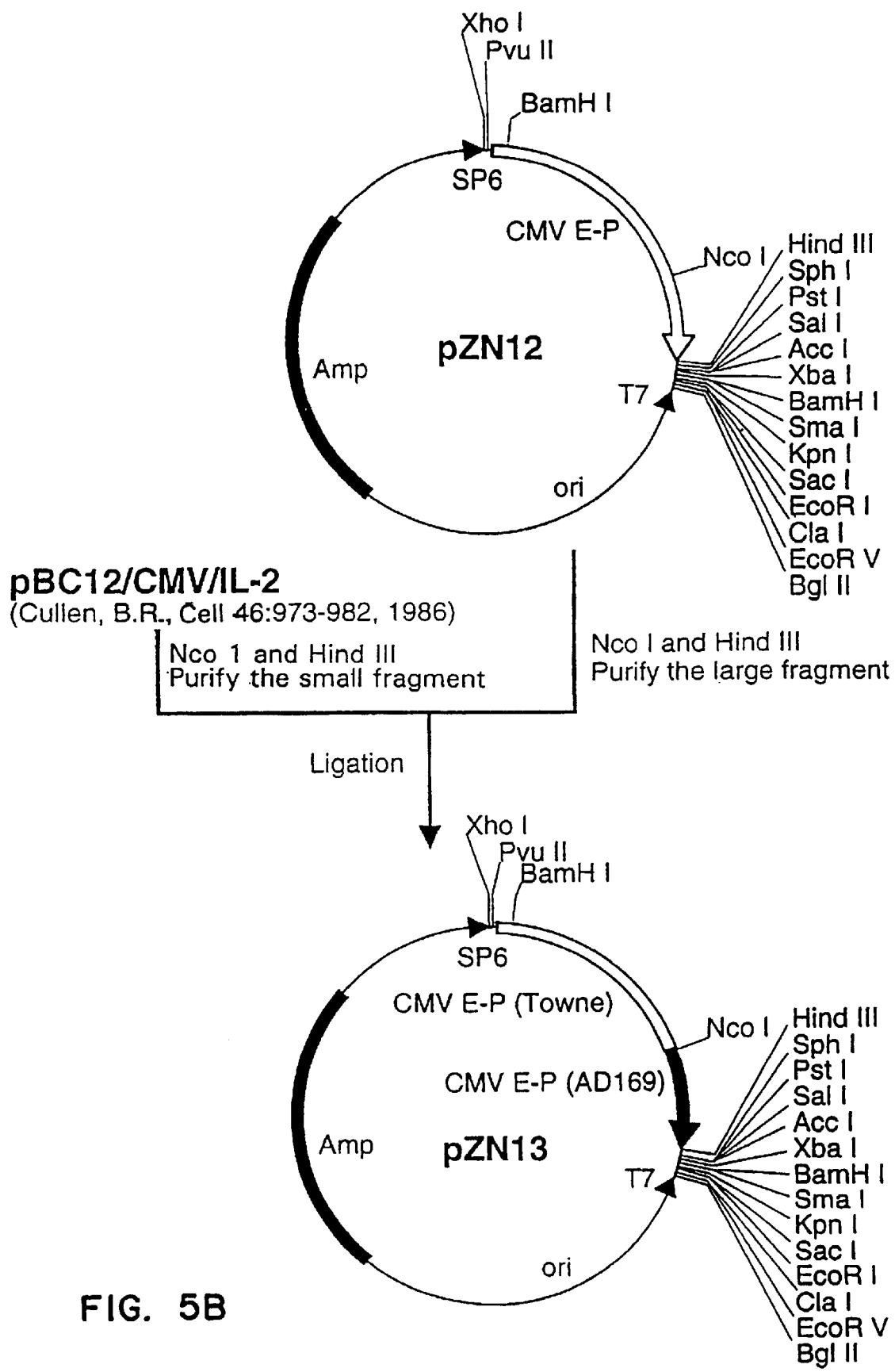
Figure 5C:
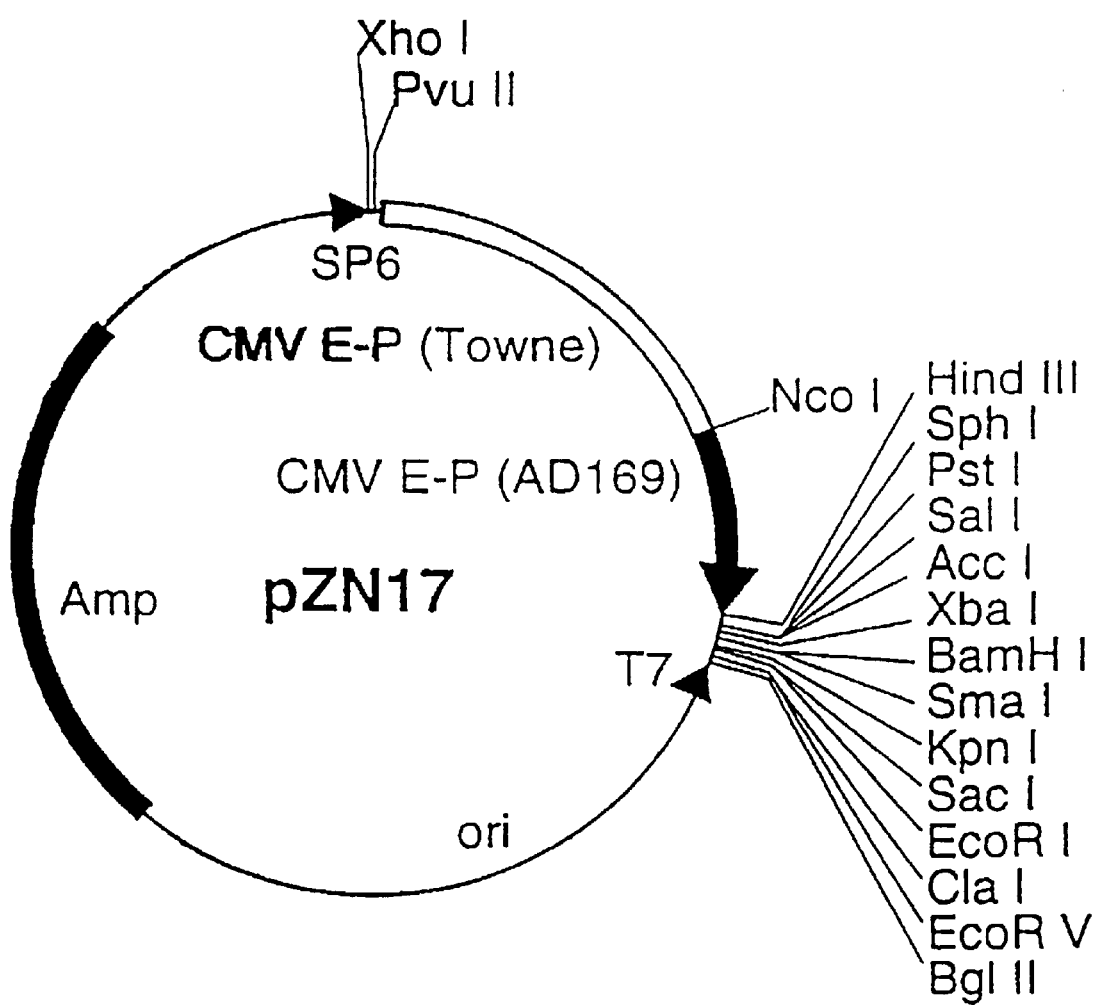
Figure 5D:
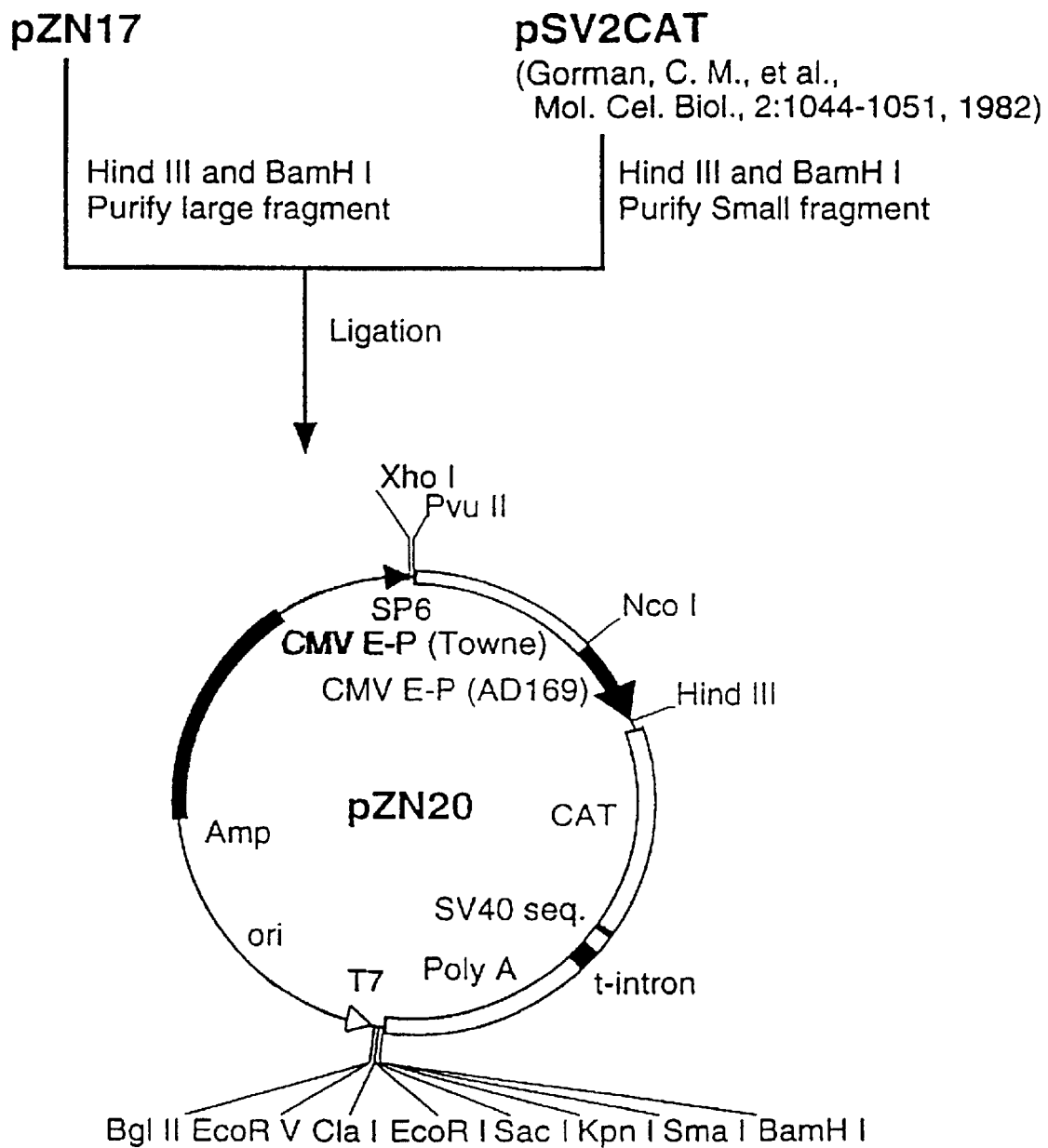

In accordance with the subject invention, nucleic acid constructs together with methods of preparation and use are provided which provide for in viva change of and/or modulation of phenotype of cells in a plurality of tissues of a mammalian host, following introduction of the constructs into the host at a dose sufficient to cause transfection of tissues and cells contacted by the nucleic acid. The components of the transfection vector generally will include as operably linked components in the direction of transcription, a transcriptional initiation region, a DNA sequence of interest and a transcriptional termination region, wherein the transcriptional regulatory regions are functional in the host mammal's cells that are targeted for transfection. optionally, an intron may be included in the construct, preferably 5' to the coding sequence. Generally, the construct does not become integrated into the host cell genome and is introduced into the host as part of a non-integrating plasmid where it is maintained primarily in an extrachromosomal or episomal form. The constructs can be either naked nucleic acid or nucleic acid associated with a lipid carrier. By a sufficient dose is meant that which will result in a desired effect, for example prevention, palliation, and/or cure of an animal or human disease, or modulation of endogenous levels of an agent of interest ("in vivo" gene therapy). The modulation may be generalized, i.e. obtained in a multiplicity of cell types or tissues, or the modulation may be selective, for example inducible and/or in only selected cell or tissue types.

Transfection of multiple tissues and cells other than those solely at or afferent to the site of introduction of the nucleic acid constructs into the host is obtained and expression is at a high level and in a large number of cells and cell types. The tissues which can be transformed include the lungs, heart, liver, bone marrow, spleen, lymph nodes, kidneys, thymus, skeletal muscle, ovary, uterus, stomach, small intestine, colon, pancreas, and brain in normal animals, as well as metastatic tumors and intravascular tumor emboli in tumor-bearing mammals. Particular cells which are transfected include macrophages, alveolar type I and type II cells, hepatocytes, airway epithelial cells, vascular endothelial cells, cardiac myocytes, myeloblasts, erythroblasts, B-lymphocytes and T-lymphocytes. The route of administration typically is into a circulating bodily fluid such as blood or cerebrospinal fluid, but other routes of administration also can be used. The constructs can be either naked nucleic acid or nucleic acid associated with a lipid carrier. Optionally, the lipid carrier molecule and/or construct may provide for targeting and/or expression in a particular cell type or types.

The nucleic acid constructs can be prepared from nucleic acid sequences which are synthetic, naturally derived or a combination thereof. The sequences can be obtained from a donor host homologous with an intended recipient host, or depending upon the nature of the nucleic acid sequence, it may be desirable to synthesize the sequence with host preferred codons. The host preferred codons may be determined from the codons of highest frequency in the proteins expressed in the largest amount in the particular host of interest. Where cloning is done in a bacterial host system, it may be beneficial to change codon choice to promote stability in the bacterial host system. Where the intended use is to treat disease resulting from an infectious organism, an appropriate source of sequence may be viral nucleic acid, either RNA or DNA.

Genes are high molecular weight, polyanionic olecules, for which carrier-mediated delivery is usually but not always required for DNA transfection of cells either in culture or in vivo. Cationic lipid carriers such as liposomes can be used to deliver transcriptional regulatory proteins. Further, liposomes themselves (unlike viral vectors) appear to be non-immunogenic in vivo. Liposome formulations, including those containing a cationic lipid, have been shown to be safe and well tolerated in human patients (Treat et al., (1990) *J. Natl. Cancer Instit.* 82:1706–1710). Although a wide variety of transfection techniques can produce high level expression of transgenes in cultured cells, only a few such methods, including those using liposomes, are compatible with in vivo gene delivery. Previous attempts at using either cationic liposomes or naked DNA to obtain in vivo transfection have resulted in transfection of a single tissue and/or transfection only of the tissue of introduction of exogenous DNA. This pattern of transfection suggests that rather than the DNA and/or liposomes being taken up by normal cellular mechanisms, cells in the tissue of introduction are damaged by the introduction method and are then able to take up some of the exogenous DNA which has been introduced.

Applicants surprisingly discovered changes which provide for both transfection of a wide variety of tissues and cell types and a high-level of transgene expression after systemic administration into a mammalian host. These changes include the use of DNA:cationic lipid carrier complexes, wherein the ratio of DNA to cationic lipid of the lipid carrier can significantly affect obtention of in vivo expression; use of a higher dose of complexes than has been used previously; use of an appropriate promoter element, for example one which is both strong and constitutively active, such as the HCMV-IE1 element where it is desired to provide enhanced expression in a wide variety of cell types in vivo; and placement of greater than 100 bp of an intron 5' to the coding region of the transgene or removal of the intron altogether to facilitate production of a desired gene product. Additionally, it has surprisingly been discovered that a number of tissues, including the lung, liver, spleen, kidney, lymph nodes and heart can be transformed following direct administration of high doses of naked DNA into a circulating bodily fluid, such as blood or cerebral spinal fluid. Alternatively, selective expression can be obtained in specific cell and tissue types and at a desired time (i.e. expression is inducible) by alterations in the components, particularly promoters and/or enhancers of the constructs used, or by the use of targeting moieties on the liposomes.

Most gene therapy strategies have relied on transgene insertion into retroviral or DNA virus vectors. Potential disadvantages of retroviruses, as compared to the use of naked DNA or the use of cationic lipid carriers, include the limited ability of retroviruses to mediate in vivo (as opposed to ex vivo) transgene expression; the inability of retrovirus vectors to transfect non-dividing cells; possible recombination events in replication-defective retrovirus vectors, resulting in infectious retroviruses; possible activation of oncogenes or inhibition of tumor suppressor genes due to the random insertion of the transgene into host cell genomic DNA; size limitations: less than 15 kb of DNA typically can be packaged in a retrovirus vector; and potential immunogenicity, leading to a host immune response against the vector. In addition, all ex vivo approaches require that the cells to be transfected be removed from the body and that they be maintained in culture for a period of time. While in culture, the cells may undergo deleterious or potentially dangerous phenotypic and/or genotypic changes. Adenoviral and other DNA viral vectors share several of the above potential limitations. Thus, the subject invention which does not use adenoviral or other DNA viral vectors has several advantages over existing techniques. Additionally, the subject invention offers ease of administration and results not achievable by other means.

The constructs for use in the invention include several forms, depending upon the intended use of the construct. Thus, the constructs include vectors, transcriptional cassettes, expression cassettes and plasmids. The transcriptional and translational initiation region (also sometimes referred to as a "romoter,"), preferably comprises a transcriptional initiation regulatory region and a translational initiation regulatory region of untranslated 5' sequences, "ribosome binding sites," responsible for binding mRNA to ribosomes and for translational initiation. It is preferred that all of the transcriptional and translational functional elements of the initiation control region are derived from or obtainable from the same gene. In some embodiments, the promoter will be modified by the addition of sequences, such as enhancers, or deletions of nonessential and/or undesired sequences. By "obtainable" is intended a promoter having a DNA sequence sufficiently similar to that of a native promoter to provide for the desired specificity of transcription of a DNA sequence of interest. It includes natural and synthetic sequences as well as sequences which may be a combination of synthetic and natural sequences.

For the transcriptional initiation region, or promoter element, any region may be used with the proviso that it provides the desired level of transcription of the DNA sequence of interest. The transcriptional initiation region may be native to or homologous to the host cell, and/or to the DNA sequence to be transcribed, or nonindigenous to the host cell or foreign or heterologous to the DNA sequence to be transcribed. By nonindigenous to the host cell is intended that the transcriptional initiation region is not normally found in the host into which the construct comprising the transcriptional initiation region is to be inserted. By foreign to the DNA sequence is intended a transcriptional initiation region that is not normally associated with the DNA sequence of interest. Efficient promoter elements for transcription initiation include the SV40 (simian virus 40) early promoter, the RSV (Rous sarcoma virus) promoter, the Adenovirus major late promoter, and the human CMV (cytomegalovirus) immediate early 1 promoter.

Inducible promoters also find use with the subject invention where it is desired to control the timing of transcription or the tissue or cell type in which the nucleic acid of interest is transcribed. Examples of inducible promoters include those obtainable from a β-interferon gene, a heat shock gene, a metallothionein gene or those obtainable from steroid hormone-responsive genes, including insect genes such as that encoding the ecdysone receptor. Such inducible promoters can be used to regulate transcription of the transgene by the use of external stimuli such as interferon or glucocorticoids. Since the arrangement of eukaryotic promoter elements is highly flexible, combinations of constitutive and inducible elements also can be used. Tandem arrays of two or more inducible promoter elements may increase the level of induction above baseline levels of transcription which can be achieved when compared to the level of induction above baseline which can be achieved with a single inducible element.

Generally, the transcriptional regulatory sequence comprises DNA up to about 1.5 kb 5' of the transcriptional start of a gene, but can be significantly smaller. As necessary, this regulatory sequence may be modified at the position corresponding to the first codon of the desired protein by site-directed mutagenesis (Kunkel, (1985) *Proc. Natl. Acad. Sci. (USA)*, 1:488–492) or by introduction of a convenient linker oligonucleotide by ligation, if a suitable restriction site is found near the N-terminal codon. In the ideal embodiment, a coding sequence with a compatible restriction site may be ligated at the position corresponding to codon #1 of the gene. This substitution may be inserted in such a way that it completely replaces the native coding sequence so that the substituted sequence is flanked at its 3' end by the gene terminator and polyadenylation signal.

Transcriptional enhancer elements optionally may be included in the transcription or expression cassette. By "transcriptional enhancer elements" is intended DNA sequences which are primary regulators of transcriptional activity and which can act to increase transcription from a promoter element, and generally do not have to be in the 5' orientation with respect to the promoter in order to enhance transcriptional activity. The combination of promoter and enhancer element(s) used in a particular cassette can be selected by one skilled in the art to maximize specific effects. Different enhancer elements can be used to produce a desired level of transgene transcription and/or expression in a wide variety of tissue and cell types. For example, the human CMV immediate early promoter-enhancer element can be used to produce high level transgene transcription and expression in many different tissues in vivo.

Examples of other enhancer elements which confer a high level of transcription on linked genes in a number of different cell types from many species include enhancers from SV40 and RSV-LTR. The SV40 and RSV-LTR are essentially constitutive. They can be combined with other enhancers which have specific effects, or the specific enhancers may be used alone. Thus, where specific control of transcription is desired, efficient enhancer elements that are active only in a tissue-, developmental-, or cell-specific fashion include immunoglobulin, interleukin-2 (IL-2) and β-globin enhancers are of interest. Tissue-, developmental-, or cell-specific enhancers can be used to obtain transgene transcription and/or expression in particular cell types, such as B-lymphocytes and T-lymphocytes, as well as myeloid, or erythroid progenitor cells. Alternatively, a tissue-specific promoter such as that derived from the human cystic fibrosis transmembrane conductance regulator (CFTR) gene can be fused to a very active, heterologous enhancer element, such as the SV40 enhancer, in order to confer both a high level of transcription and tissue-specific transgene transcription. In addition, the use of tissue-specific promoters, such as LCK, allow targeting of transgene transcription to T lymphocytes. Tissue specific transcription of the transgene can be important, particularly in cases where the results of transcription of the transgene in tissues other than the target tissue would be deleterious.

Tandem repeats of two or more enhancer elements or combinations of enhancer elements can significantly increase transgene expression when compared to the use of a single copy of an enhancer element; hence enhancer elements find use in the cassettes. The use of two different enhancer elements, which can be either from the same or from different sources flanking or within a single promoter can in some cases produce transgene expression in each tissue in which each individual enhancer acting alone would have an effect, thereby increasing the number of tissues in which transcription is obtained. In other cases, the presence of two different enhancer elements results in silencing of the enhancer effects. Evaluation of particular combinations of enhancer elements for a particular desired effect or tissue of expression is within the level of skill in the art.

Although generally it is not necessary to include an intron in the transcription and/or expression cassette, an intron optionally can be included which comprises a 5' splice site (donor site) and a 3' splice site (acceptor site) separated by a sufficient intervening sequence to produce high level extended in vivo transcription and/or expression of a transgene. Generally, an intervening sequence of about 100 bp produces the desired expression pattern and/or level, but the size of the sequence can be varied as needed to achieve a desired result. The optional intron placed 5' to the coding sequence results in high level extended in vivo expression of a transgene but generally is not necessary to obtain expression. Optimally, the 5' intron specifically lacks cryptic splice sites which result in aberrantly spliced mRNA sequences.

If used, the intron splice donor and splice acceptor sites, arranged from 5' to 3' respectively, are placed between the transcription initiation site and the translational start codon. Alternatively, the intervening sequence can be placed 3' to the translational stop codon and the transcriptional terminator or inside the coding region. The intron can be a hybrid intron with an intervening sequence or an intron taken from a genomic coding sequence. An intron 3' to the coding region, particularly one of less than 100 bp, or any intron which contains cryptic splice sites can under certain conditions substantially reduce the level of transgene expression produced in vivo. However, unexpectedly, a high level of in vivo expression of a transgene can be achieved using a vector that lacks an intron. Such vectors therefore are of particular interest for in vivo transfection.

Downstream from and under control of the transcriptional and/or translational initiation regulatory regions is a multiple cloning site for insertion of a nucleic acid sequence of interest which will provide for one or more alterations of host phenotype, for example to dramatically improve the treatment of acquired immune deficiency syndrome (AIDS), cystic fibrosis, cancer, heart disease, autoimmune diseases and a variety of life threatening infections. Conveniently, the multiple cloning site can be employed for a variety of nucleic acid sequences in an efficient manner. The nucleic acid sequence inserted in the cloning site can encode a ribozyme sequence or encode a polypeptide, for example, a protein having enzymatic activity, with the proviso that if the coding sequence encodes a polypeptide, it should lack cryptic splice sites which can block production of appropriate mRNA molecules and/or produce aberrantly spliced or abnormal mRNA molecules. The polypeptide can be one which is active intracellularly, a transmembrane protein, or it may be a secreted protein. It also can be a mutant protein, for example, which is normally secreted, but which has been altered to act intracellularly. The nucleic acid sequence can be DNA; it also can be a sequence complementary to a genomic sequence (an "antisense sequence"), where the genomic sequence may be one or more of an open reading frame, an intron, a non-coding leader sequence, or any other sequence where the complementary sequence will inhibit transcription, or messenger RNA processing, for example splicing, or translation.

For the treatment of AIDS, anti-TAT, REV, TAR or other critical anti-HIV sequences may be used, particularly for expression of the appropriate coding sequences in T lymphocytes, macrophages and monocytes which can be achieved following iv administration of the appropriate coding sequences. Thus, DNA sequences which code for mRNA (an antisense or ribozyme sequence such as one to HIV-REV or a BCR-ABL sequence) or code for proteins such as transdominant negative mutants which specifically prevent the integration of HIV genes into the host cell genomic DNA, replication of HIV sequences, translation of HIV proteins, processing of HIV mRNA, or virus packaging in human cells can be used.

Expression of wild-type conductance regulator (CFTR) gene in the lungs of cystic fibrosis patients can be used in the treatment of cystic fibrosis (see Collins, (1992) *Science* 256:774–783). CFTR cDNA can be obtained from Dr. Collins at University of Michigan or Dr. Tsui at Toronto Sick Children's Hospital.

Expression of wild-type p53 in tumors of cancer patients with absent or aberrant expression of this gene can be used as a means of treating these patients. p53 is obtainable from Dr. Vogelstein at John Hopkins Univ. Other methods of cancer treatment include transcription of antisense sequences to over-expressed, transforming oncogenes, such as myc or ras in tumors.

Viral pneumonias remain a major cause of death and disability of the very young and in the aged population. Proteins such as granulocyte macrophage colony stimulating factor (GM-CSF), which stimulates production of white blood cells from the bone marrow of immunocompromised patients can be useful in controlling the course of viral infections. In particular, GM-CSF delivered via gene transfer would serve with prophylactic modalities for those at risk for occurrence of viral pneumonia, as well as in therapeutic modalities for treatment of the infection. GM-CSF also has significant anti-tumor activity.

Other examples of nucleic acid sequences of interest, include those encoding the LDL (low density lipoprotein) receptor, which specifically lowers serum cholesterol, and which can reduce the risk of heart attack in individuals with elevated serum cholesterol levels; sequences such as an antisense IL-1 receptor sequence to down-regulate the IL-1 receptor as a treatment of conditions involving inflammation, including sepsis, rheumatoid arthritis and asthma; downregulation of the gene coding for apo(a), circulating levels of which are correlated with the risk of coronary artery disease (CAD); and genes which block activity of activated T cell clones which attack myelin in multiple sclerosis or other targets in autoimmune diseases. A T-cell lymphocyte clone activated to recognize and attack Myelin can be targeted by using an antisense sequence, ribozyme sequence or transgene coding for a transdominant negative mutant which specifically blocks surface expression on the T-cell of T-cell receptor components which mediate recognition and/or attack of myelin-sheathed cells. Other beneficial therapeutic nucleic acid sequences which can be expressed in appropriate cells in vivo using this invention include nucleic acid sequences encoding molecules which have superoxide dismutase activity or catalase activity to protect the lung from oxidant injury; endothelial prostaglandin synthase to produce prostacyclin and prostaglandin E2; and antiprotease alpha-l antitrypsin, and erythropoietin.

The termination region which is employed primarily will be one of convenience, since termination regions appear to be relatively interchangeable. The termination region may be native to the intended nucleic acid sequence of interest, or may be derived from another source. Convenient termination regions are available and include the 3' end of a gene terminator and polyadenylation signal from the same gene from which the 5' regulatory region is obtained. Alternatively, a terminator and polyadenylation signal from a different gene or genes may be employed with similar results. Specific sequences which regulate post-transcriptional mRNA stability may optionally be included. For example, certain polyA sequences (Volloch and Housman, (1981) *Cell* 23:509–514) and β-globin mRNA elements can increase mRNA stability, whereas certain AU-rich sequences in mRNA can decrease mRNA stability (Shyu et al., (1989) *Genes and Devel.* 3:60–72). In addition, AU regions in 3' non-coding regions may be used to destabilize mRNA if a short half-life mRNA is desirable for a particular application.

The construct may additionally include sequences for selection, such as a neomycin resistance gene or a dihydrofolate reductase gene and/or signal sequences to generate recombinant proteins that are targeted to different cellular compartments or secreted when the wild type sequence is not. Any of a variety of signal sequences may be used which are well-known to those skilled in the art. These signal sequences may allow generation of new vaccine strategies or produce soluble antagonists directed against specific cell surface receptors such as transformed oncogenes. The sequences for selection may be on a separate plasmid and cotransfected with the plasmid carrying the therapeutic nucleic acid. Where a carrier is used, the selection plasmid may be complexed to a different carrier or to the same carrier as the therapeutic plasmid.

In some cases, it may be desirable to use constructs that produce long term transgene effects in vivo, either by integration of the transgene into host cell genomic DNA at high levels or by persistence of the transgene in the nucleus of cells in vivo in stable, episomal form. When desired, integration of the transgene into genomic DNA of host cells in vivo may be facilitated by administering the transgene in a linearized form (either the coding region alone, or the coding region together with 5' and 3' regulatory sequences, but without any plasmid sequences present). It may be possible to further increase the incidence of transgene integration into genomic DNA by incorporating a purified retroviral enzyme, such as the HIV-1 integrase enzyme, into the lipid carrier-DNA complex. Appropriate flanking sequences are placed at the 5' and 3' ends of the transgene DNA. These flanking sequences have been shown to mediate integration of the HIV-1 DNA into host cell genomic DNA in the presence of HIV-1 integrase. Alternatively, duration of transgene expression in vivo can be prolonged by the use of constructs that contain non-transforming sequences of a virus such as Epstein-Barr virus, and sequences such as orip and EBNA-1, which appear to be sufficient to allow heterologous DNA to be replicated as a plasmid in mammalian cells (Burhans, et al., (1986) *Cell* 62:955–965).

The recombinant coding-sequence flanked at its 5' end by the promoter and regulatory sequences and at its 3' end by a terminator and regulatory sequences may be introduced into a suitable cloning plasmid (e.g., pUC18, pSP72) for use in direct DNA uptake in host cells following introduction into the host. It is a theory of the invention that the naked nucleic acid when introduced into the host is protected from degradation by nucleases by associating with lipid carriers in the blood, such as chylomicrons. Thus, more effective transfection may be achieved when lipid in the blood is at an elevated level after ingestion of food.

The nucleic acid construct also may be complexed with a carrier such as a lipid carrier, particularly a cationic lipid carriers to form a complex. By a complex is intended an association between a nucleic acid construct such as a plasmid containing an expression cassette or a transcriptional cassette and a lipid mixture. The physical form of the complex may be a liposome with nucleic acid complexed to the outside or entrapped within the liposome, or the complex may be in the form of interleaved lipid and nucleic acid, or the complex may be a mixture of any or all of the above physical forms. For intravenous administration, generally the complex is prepared by sonicating the lipid mixture to be used and then mixing the sonicated mixture with the nucleic acid in an appropriate DNA:lipid ratio in a physiologically acceptable diluent immediately prior to use. The lipid carriers can be prepared from a variety of cationic lipids, including DOTAP, DOTMA, DDAB, L-PE, and the like. Lipid carrier mixtures containing a cationic lipid, such as N-[1-(2,3-dioleyloxy) propyl]-N,N,N-triethylammonium chloride (DOTMA) also known as "lipofectin", dimethyl dioctadecyl ammonium bromide (DDAB), 1,2-dioleoyloxy-3-(trimethylammonio) propane (DOTAP) or L-lysinyl-phosphatidylethanolamine (L-PE) and a second lipid, such as dioleoylphosphatidylethanolamine (DOPE) or cholesterol (Chol), are of particular interest. DOTMA synthesis is described in Felgner, et al., (1987) *Proc. Nat. Acad. Sciences*, (*USA*) 84:7413–7417. DOTAP synthesis is described in Stamatatos, et al., *Biochemistry*, (1988) 27:3917–3925. DOTMA:DOPE lipid carriers can be purchased from, for example, BRL. DOTAP:DOPE lipid carriers can be purchased from Boehringer Mannheim. Cholesterol and DDAB are commercially available from Sigma Corporation. DOPE is commercially available from Avanti Polar Lipids. DDAB:DOPE can be purchased from Promega. Biodegradable cationic amphophiles also can be used (see, for example, copending PCT application attorney docket number MEBI-002/00WO filed Dec. 17, 1992).

Lipid carriers such as cationic liposomes can mediate high level cellular expression of transgenes or mRNA by delivering the nucleic acid into a wide variety of cells in culture. The use of specific cationic lipids can confer specific advantages for in vivo delivery of complexes. For example, iv injection of nucleic acid complexed to DOTAP-containing liposomes or ethyl-phosphatidylcholine (E-PC) lipid carriers can target transgene expression primarily to the lung. Furthermore, DOTAP, as well as L-PE and cholesterol ester β-alanine (CEBA) are fully metabolized by cells, whereas DOTMA cannot be fully metabolized by cells. Therefore, DOTAP, E-PC, and L-PE, but not DOTMA, are suitable for repeated injection into mammalian hosts. Additionally, using a lipid carrier comprising a cationic lipid and a second lipid, particularly cholesterol or DOPE can maximize transgene expression in vivo. Also, mixing a steroid, such as cholesterol, instead of DOPE, with DOTAP, DOTMA, or DDAB, substantially increases transgene expression in vivo.

Particular cells and tissues can be targeted, depending upon the route of administration and the site of administration. For example, a tissue which is closest to the site of injection in the direction of blood flow can be transfected in the absence of any specific targeting. Additionally, if desired, the lipid carriers may be modified to direct the complexes to particular types of cells using site-directing molecules. Thus antibodies or ligands for particular receptors or other cell surface proteins may be employed, with a target cell associated with a particular surface protein. For example, the AIDS virus is primarily directed to cells having the CD4 surface protein. By having anti-CD4 antibody bound to the surface of the lipid carrier, a nucleic acid lipid carrier complex can be directed primarily to T-helper cells.

A particular ligand or antibody can be conjugated to the lipid in accordance with conventional ways, either by conjugating the site-directing molecule to a lipid or by providing for a linking group on a lipid present in the bilayer for linking to a functionality of the site-directing compound. Such techniques are well known to those skilled in the art. Ligand-directed DNA-polycation complexes have been shown to transfect to hepatocytes in the liver after iv injection; the ability to transfect other cell types or tissue types by this approach has not been demonstrated.

Non-cationic lipid carriers, particularly pH sensitive liposomes, offer another potentially attractive approach to in vivo gene therapy. However, as compared to cationic liposomes, pH sensitive liposomes are less efficient in capturing DNA and delivering DNA intracellularly and may be inactivated in the presence of serum, thus limiting their iv use.

A number of factors can affect the amount of expression in transfected tissue and thus can be used to modify the level of expression to fit a particular purpose. Where a high level of expression is desired, all factors can be optimized, where less expression is desired, one or more parameters can be altered so that the desired level of expression is attained. For example, if high expression would exceed the therapeutic window, then less than optimum conditions can be used. The factors which can be modified are as follows:

Either the lipid composition of the complex or the mean diameter of the lipid carriers (when in particle form such as a liposome) injected can dramatically affect the level of transgene expression produced in vivo. Thus, the liposomal lipid compositions generally have a composition of 50% molar ratio of cationic lipid to non-cationic lipid, but may range from 5% to 100%. The diameter of the lipid carriers should generally be within the range of 100 nm to 10 $\mu$m. Cationic lipid carrier-DNA complexes wherein the lipid carriers range from 100 nm to several $\mu$m in diameter can produce significant levels of transgene expression after systemic introduction into a mammalian host.

The use of lipid carriers of greater than 500 nm (i.e. multilamellar vesicles (MLV) or large unilamellar vesicles (LUV)) can in certain cases significantly increase the level of transgene expression achieved in a mammalian host when compared to small unilamellar vesicles (SUV). MLV and LUV are prepared by vortexing rather than sonicating after addition of the aqueous material to the dry lipid film. Where it is desired to use particles, the resulting lipid carriers can be extruded under high pressure through sized polycarbonate membranes to achieve particular uniform size distributions for a particular use.

The use of particular nucleic acid to lipid carrier ratio also can increase the amount of transfection and/or the level of transcription and/or expression of a nucleic acid sequence of interest. The ratios used determine whether and to what level transgenes are expressed in vivo thus can be optimized, depending upon various factors including the nature of the construct, the size and lipid composition of the lipid carrier and whether it is MLV or SUV, the route of administration and the host mammal. As an example, using a reporter gene CAT (chloramphenicol acetyl transferase), an approximately 1:1 (range 0.5:1 to 2:1) DNA to lipid carrier ratio ($\mu$g DNA to nmoles of the cationic lipid) produces the highest levels of gene expression in a mouse in all organs after ip administration, and an approximately 1:4 ratio, (range 2:1 to 1:7) produces the highest levels of gene expression in all organs after iv administration. In addition to achieving a high level of transgene expression in a wide variety of tissues using optimal conditions, the majority of all cells present in the lung, spleen, lymph nodes and bone marrow are transfected in vivo, as well as the majority of all endothelial cells present in the heart.

The DNA:lipid carrier ratio also can affect at what level transgenes are expressed in mammalian hosts after systemic injection of the complexes. Several factors are important in order optimize the DNA:lipid carrier ratio for a particular expression level desired. Thus, specific DNA:lipid carrier ratios are required for each type of cationic lipid used as well as for each different lipid carrier size used. To optimize for maximum expression, for each lipid carrier composition used, DNA is be mixed together with the lipid carriers in multiple different ratios, ranging from 6:1 to 1:10 ($\mu$g DNA to rnmole cationic lipid), in order first to determine which ratios result in aggregation of the DNA:lipid carrier complexes. Ratios which result in aggregation cannot be used in vivo. The ratios which do not result in aggregation are tested in animal models to determine which of the DNA:lipid carrier ratios confers the desired level of transgene expression in vivo. For example, the optimal DNA:lipid carrier ratios for SUV for DOTMA:DOPE, DDAB:DOPE, DOTAP:DOPE, DOTAP:Cholesterol, L-PE:CEBA, DDAB:Cholesterol and L-PE:DOPE are 1:4, 1:3, (very low activity at all ratios), 1:6, 1:1, 1:5, and 2:1, respectively. DNA:lipid carrier complexes are made in appropriate physiologic solutions. The DNA:lipid carrier complexes are mixed in physiologic solutions (approximately 290 milliosmoles) which do not themselves induceaggregation of the DNA:lipid carrier complexes. The solutions include 5% dextrose in water or normal saline. Cell surface receptors for cationic lipid carriers can be used to both regulate and confer target cell specificity on transgene expression in mammalian hosts. Cationic lipid carrier:DNA complexes are internalized by cells by a classical receptor-mediated endocytosis (see FIG. 7) using cell surface receptors which contain specific binding sites for, and are able to internalize, cationic molecules. Using agents such as cytokines, growth factors, other soluble proteins and certain drugs, it is thus possible to selectively up or down regulate these cation-binding receptors. The rate of up or down regulation of these receptors by the appropriate agent will allow selection of specific cells for enhanced or reduced levels of transfection in vivo. Cell surface receptors for naked DNA also can be used both to regulate and to confer target cell specificity on transgenic expression in mammalian host.

The most frequent interaction between DOTMA lipid carriers, either uni- or multilamellar lipid carriers, complexed to plasmid DNA and the various cell types (for example, CV-1 monkey kidney cells, U937 human myelomonocytic leukemia cells, K562, MEL (murine erythroblastic leukemia cells), rat alveolar macrophages, and alveolar type II cells), is that of lipid carrier adhesion and internalization. This interaction is common to well-defined examples of receptor-mediated endocytosis. All cells which appear to have contacted cationic lipid carrier:DNA complexes ingest the complexes following binding of the complexes to the plasma membrane. All these cell types demonstrate the same classical receptor-mediated endocytic pathway of internalization.

The mammalian host may be any mammal, particularly a mammal having symptoms of a genetically-based disorder or an infectious disease which is amenable to gene-based therapy. Thus, the subject application finds use in domestic animals, feed stock, such as bovine, ovine, and porcine, as well as primates, particularly humans. The mammalian host may be pregnant, and the intended recipient of the gene-based therapy may be either the gravid female or the fetus or both.

In the method of the invention, transfection in vivo is obtained by introducing a therapeutic transcription or expression vector into the mammalian host, either as naked DNA or completed to lipid carriers, particularly cationic lipid carriers. The constructs may provide for integration into the host cell genome for stable maintenance of the transgene or for episomal expression of the transgene. The introduction into the mammalian host may be by any of several routes, including intravenous or intraperitoneal injection, intratracheally, intrathecally, parenterally, intraarticularly, intranasally, intramuscularly, topical, transdermal, application to any mucous membrane surface, corneal instillation, etc. Of particular interest is the introduction of a therapeutic expression vector into a circulating bodily fluid or into a body orifice or cavity, such as lung, colon, vagina, and the like. Thus, iv administration and intrathecal administration are of particular interest since the vector may be widely disseminated following such routes of administration, and aerosol administration finds use with introduction into a body orifice or cavity. Any physiologically acceptable medium may be employed for administering the DNA or lipid carriers, such as deionized water, saline, phosphate-buffered saline, 5% dextrose in water, and the like, depending upon the route of administration Other components may be included in the formulation such as buffers, stabilizers, biocides, etc. These components have found extensive exemplification in the literature and need not be described in particular here. Any diluent or components of diluents that would cause aggregation of the complexes should be avoided, including high salt, chelating agents, and the like.

The amount of naked DNA or complexes used will be an amount sufficient to provide for adequate dissemination to a variety of tissues after entry of the DNA or complexes into the bloodstream and to provide for a therapeutic level of expression in transfected tissues. A therapeutic level of expression is a sufficient amount of expression to, prevent, treat or palliate a disease or infection of the host mammal. In addition, the dose of the nucleic acid vector used must be sufficient to produce a desired level of transgene expression in the tissue or tisses of interest, in vivo for example, $\geq 1$ mg of an expression plasmid alone injected into a mouse results in a high level of expression of the CAT gene in multiple tissues. Other DNA sequences, such as adenovirus VA genes can be included in the administration medium and be co-transfected with the gene of interest. The presence of genes coding for the adenovirus VA gene product may significantly enhance the translation of mRNA transcribed from the plasmid if this is desired.

The level and tissues of expression of the recombinant gene may be determined at the MRNA level and/or at the level of polypeptide or protein. Gene product may be quantitated by measuring its biological activity in tissues. For example, enzymatic activity can be measured by biological assay or by identifying the gene product in transfected cells by immunostaining techniques such as probing with an antibody which specifically recognizes the gene product or a reporter gene product present in the expression cassette. Alternatively, potential therapeutic effects of the gene product can measured, for example where the DNA sequence of interest encodes GM-CSF, by determining the effects of gene expression on survival of lethally irradiated animals in which the GM-CSF transgene is expressed. Production of significant amounts of a transgene product will substantially prolong the survival of these mice.

Where expression of the polypeptide/protein or even the mRNA itself confers a changed biochemical phenotype upon the host, the presence of a new phenotype or absence of an old phenotype may be evaluated; for example, as a result of transfection of the host cells, there may be enhanced production of pre-existing desirable products formerly produced in insufficient quantities or there may be reduction or even suppression of an undesirable gene product using antisense, ribozyme or co-suppression technologies; in the case of suppression, areduction of the gene product may be determined. Typically, the therapeutic cassette is not integrated into the host cell genome. If necessary, the treatment can be repeated on an ad hoc basis depending upon the results achieved. If the treatment is repeated, the mammalian host can be monitored to ensure that there is no adverse immune or other response to the treatment.

As an example, in a clinical setting where it is desired to treat a particular disease state, both the biological efficacy of the treatment modality as well as the clinical efficacy need to be evaluated, if possible. For example, in the treatment of cystic fibrosis, there is s generalized epithelial dysfunction which manifests itself as abnormalities in the electrolyte and water content of luminal liquid or "secretions" of the airways, sweat glands, intestinal and reproductive tracts, and pancreas. The biological efficacy of gene therapy therefore can be evaluated by for example measuring the transepithelial electrical potential difference prior to treatment and following transaction. The evaluations can be done following transfection of nasal cells and also following transfection lung cells. Examples of techniques which can be used for measuring the bioelectric potential difference across respiratory epithelial and cystic fibrosis as described in Knowles, et al., (1981) *New England General of Medicine* 305:1489–1495; Knowles, et al., (1983) *General of Clinical Investigation* 71:1410–1417; and Knowles, et al., (1983) *Science* 221:1067–1070. The clinical efficacy, whether treatment of the underlying defect is effective in changing the course of disease, can be more difficult to measure. While the evaluation of the biological efficacy goes a long way as a surrogate end point for the clinical efficacy, and is not definitive. Thus, measuring a clinical endpoint such as the so-called "spirometry" factors which give an indication of lung function of a for example, a six-month period of time, may give an indication of a clinical efficacy of the treatment regimen. Typical measurements would include forced vital capacity (FVC) of the lung and forced expired volume in one second (FEV). An example of the type of clinical study which can be performed to evaluate the efficacy of gene therapy for cystic fibrosis is one which is being used for amiloride for the treatment of lung disease and cystic fibrosis: Knowles, et al., (1990) *New England General of Medicine* 322:1189–1194. Similarly, one killed in the art can evaluate the biological and linical efficacy of a particular gene therapy protocol.

The subject compositions can be provided for use in one or more procedures. Kits will usually include the DNA either as naked DNA or complexed to lipid carriers. Additionally, lipid carriers may be provided in a separate container for complexing with the provided DNA. The DNA either for direct administration or for complexing with lipid carriers, or the lipid carrier/DNA complexes may be present as concentrates which may be further diluted prior to use or they may be provided at the concentration of use, where the vials may include one or more dosages. Conveniently, single dosages may be provided in sterile vials so that the physician or veterinarian may employ the vials directly, where the vials will have the desired amount and concentration of agents. Thus, a vial may contain the DNA or the DNA/lipid carrier complexes in appropriate proportional amounts. When the vials contain the formulation for direct use, usually there will be no need for other reagents for use with the method.

The invention finds use in in vivo prevention, treatment and/or palliation of a number of diseases. In vivo replacement of a gene can be accomplished by techniques such as homologous recombination or initial knockout of the aberrant gene and subsequent replacement with the desired transgene. An additional benefit of expressing nucleic acids in appropriate cells in vivo using this invention, is that the encoded proteins would be processed and subject to post translational modification in the correct manner.

The following examples are offered by way of illustration and not by limitation.

EXAMPLES

Table of Contents

Example 1 Preparation of Plasmids for in vivo Gene Therapy
  pRSVCAT
  p5'PRL3-CAT
  pSIS-CAT
  pZN20 (see FIG. 5)
  pZN27 (see FIG. 9)
  pZN46 (see FIGS. 10 A,B)
  pZN32 (see FIG. 11)
  pZN51 (see FIG. 13)
  pZN60, pZN61, pZN62, pZN63 (see FIGS. 14, A, B, C)
  pCIS-CAT Example 2 Preparation of Lipid Carriers and DNA Complexing with Lipid Carriers
  Preparation of Lipid Carriers
  Plasmid Preparation
  Preparation of Lipid Carrier-Plasmid Complexes Example 3 Demonstration by Immunohistochemistry of CAT
  Gene Expression in the Lung after Intravenous (iv) Injection of pZN27-DDAB:Cholesterol Lipid Carrier Complexes (see FIG. 1)

Example 4 Expression of pCIS-CAT following Intraperitoneal Administration

Example 5 Demonstration of CAT Gene Expression in the spleen After Intravenous (iv) Injection of p5'PRL3-CAT:L-PE:CEBA Complexes Example 6 Injection of DOTMA:DOPE+pSIS-CAT Plasmid clearly did Not Produce Detectable CAT Gene Expression in vivo Example 7 Interaction of DNA:Lipid Carrier Complexes with Cell Surface Receptors (see FIG. 7)

Example 8 Demonstration that Mouse T Lymphocytes are Transfected in vivo (see FIGS. 2 A,B)

Figures 3, 6A:
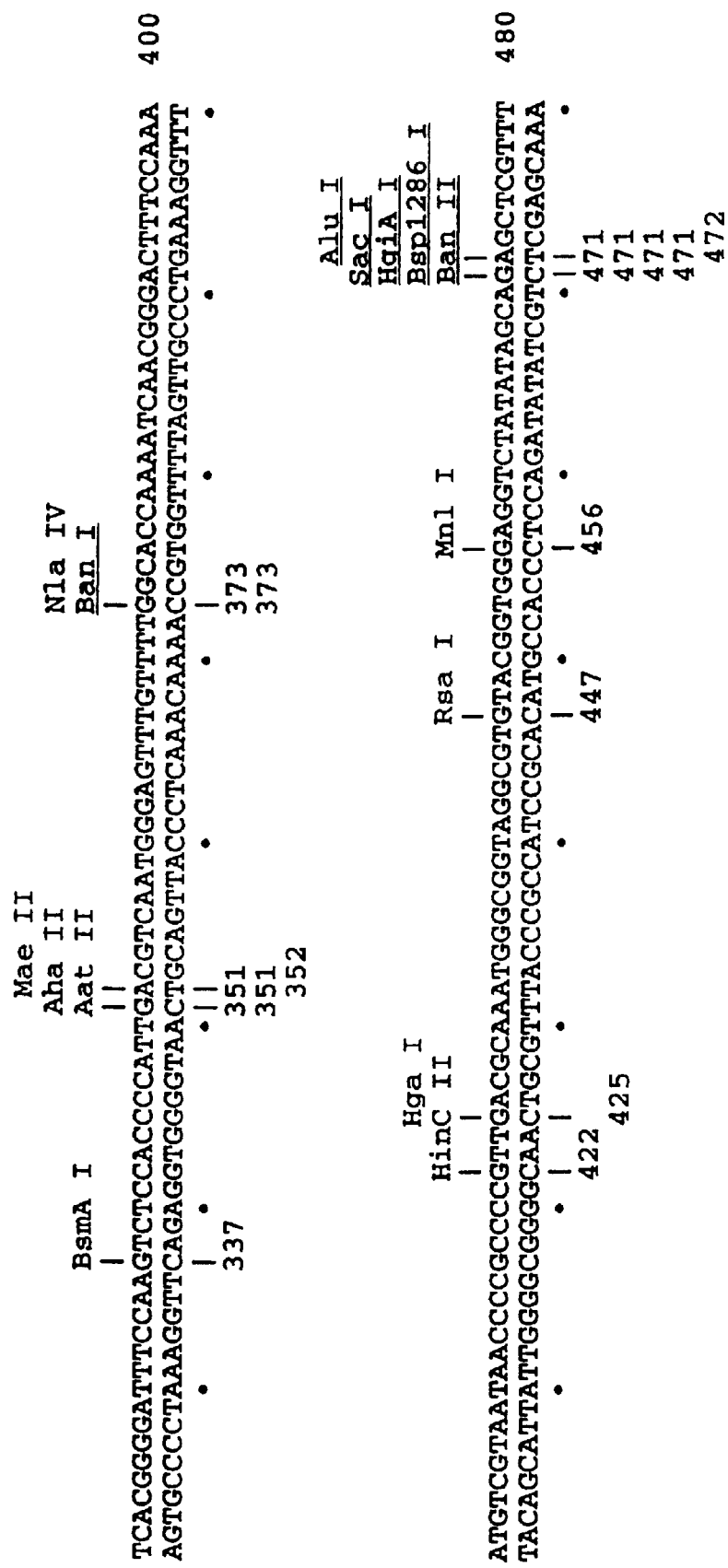
FIG. 6A shows a restriction map of the immediate early enhancer and promoter region of HCMV (Towne) and HCMV(AD169) is shown in FIG. 6C.
Figures 5, 6A:
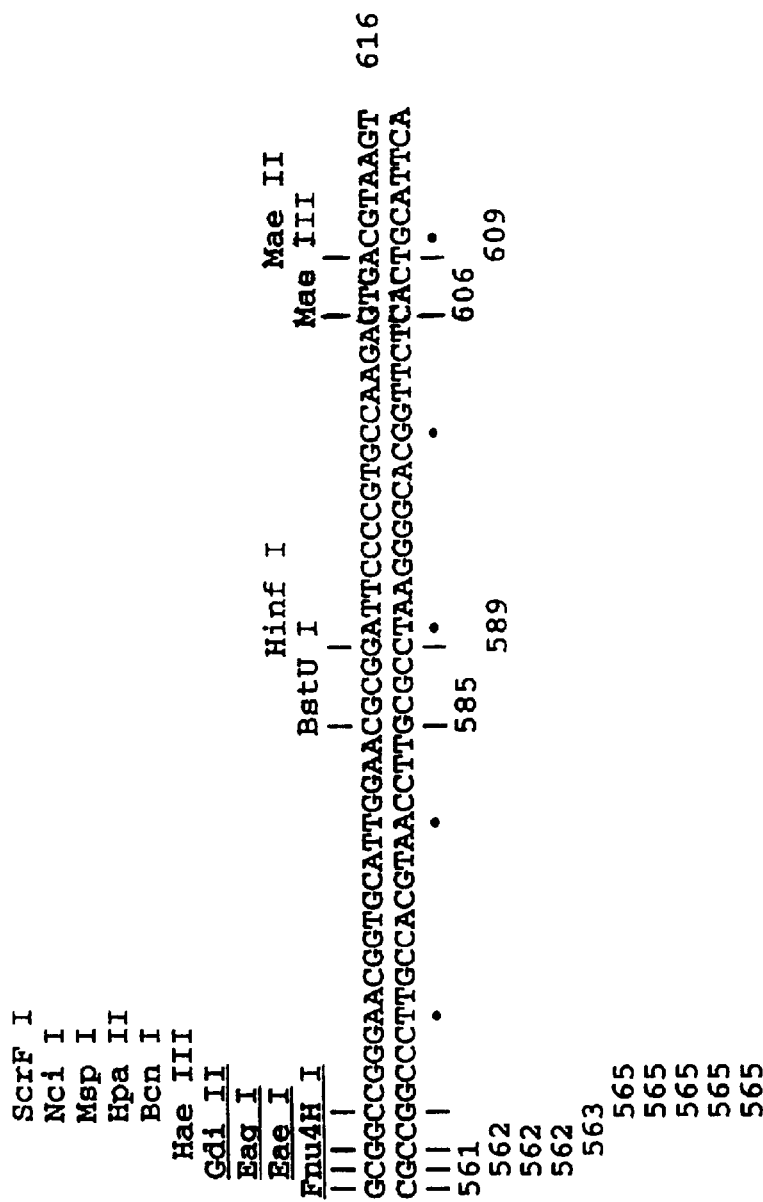
Figures 4, 6C:
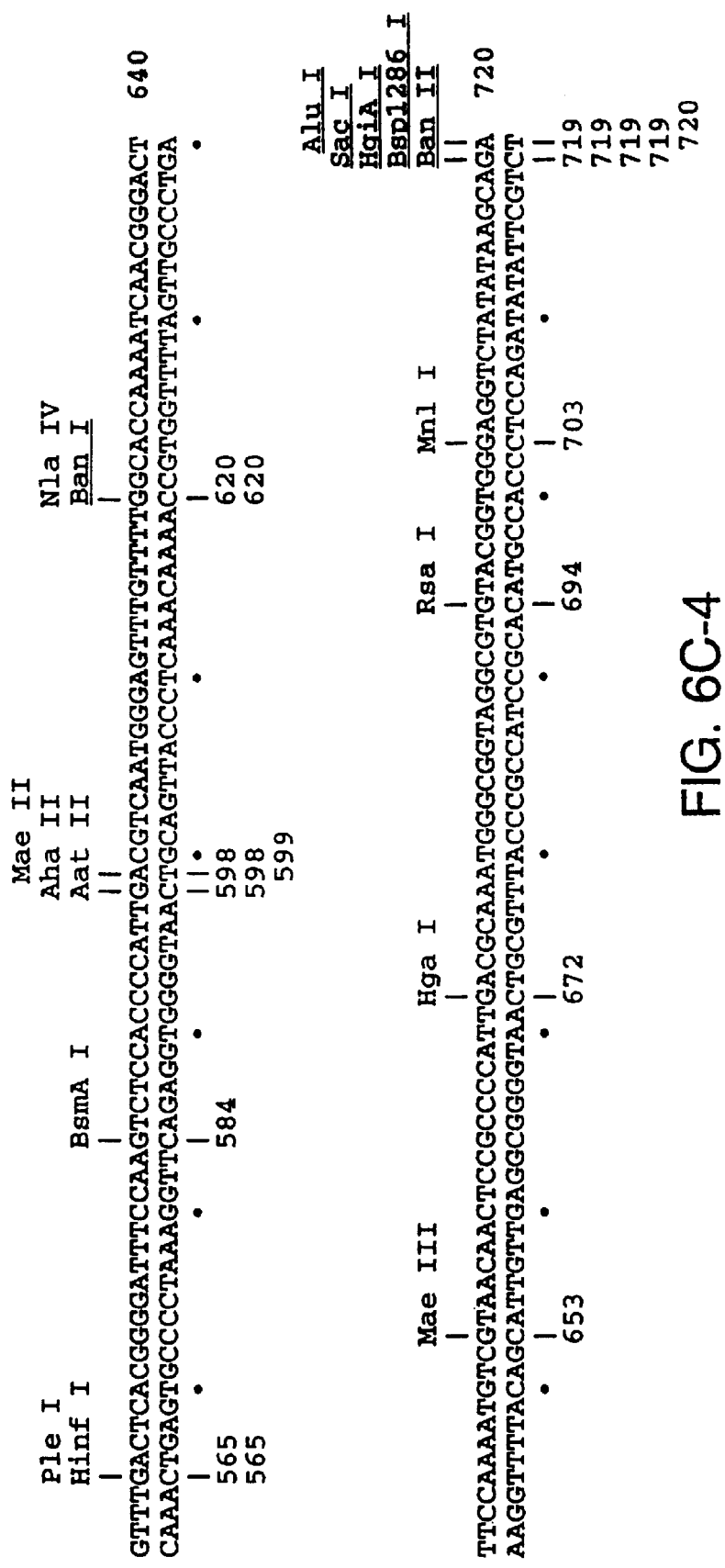
FIGS. 4A–4B show transfection of human T lymphocytes (CD4$^+$) by CAT expression plasmid-DNA complexes in culture. The lipid carrier composition was 1:1 molar ratio DDAB:DOPE small uni-lamellar vesicles (SUV). 25 µg of pZN27 complexed with 50 nmoles cationic lipid was added to 10 million cells in culture. Cells were incubated with anti CAT mouse monoclonal antibody, followed by Texas red-conjugated goat anti mouse IgG.
FIG. 6B shows a sequence comparison of the two HCMV promoters. The position of the NcoI site is indicated by an asterisk.

Example 9 Demonstration that Mouse Hematopoietic Bone Marrow-derived Cells are Transfected in vivo Example 10 Demonstration that Human CD4$^+$ Lymphocytes, freshly isolated from Normal Donors, are Transfected (see FIG. 4)

Figure 21:
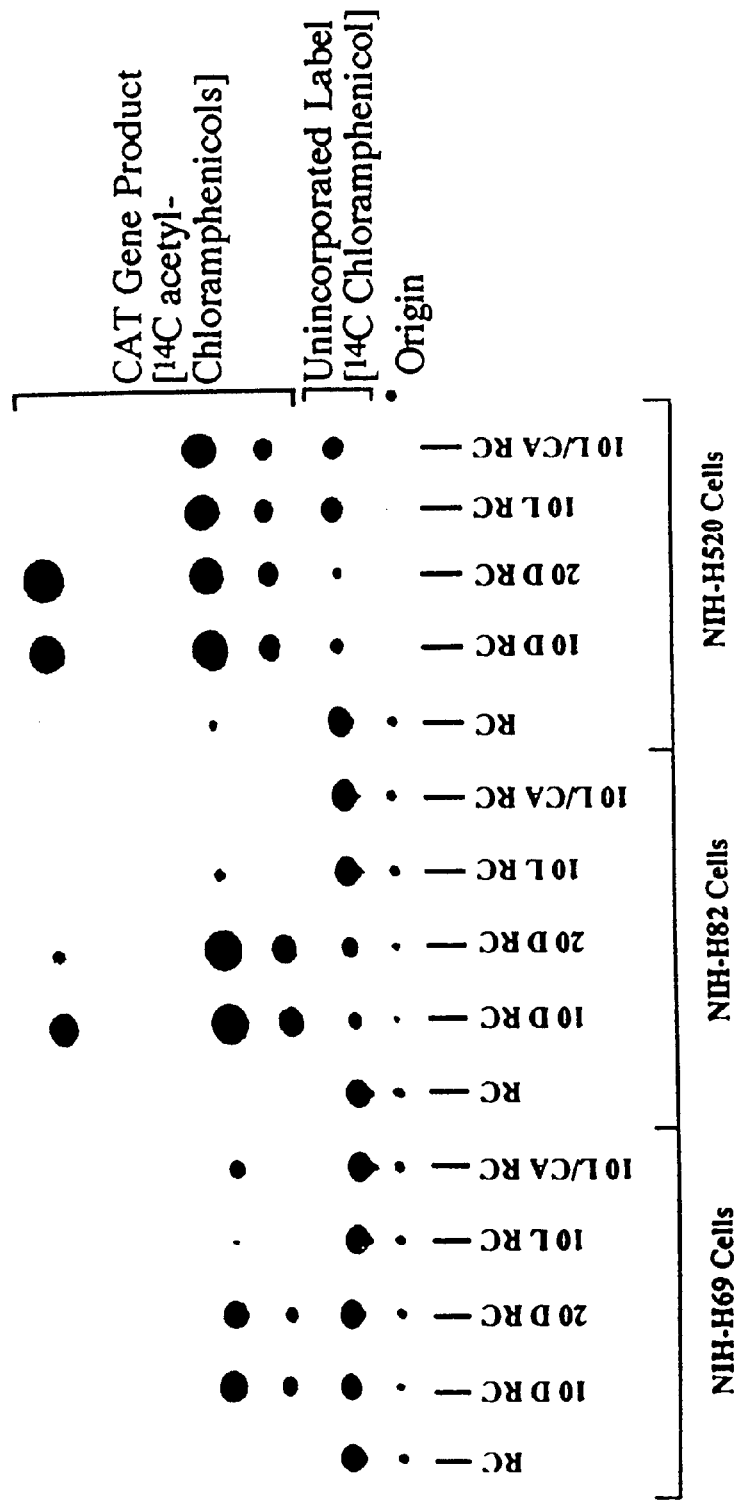
FIG. 21 shows human lung cancer cell line transfections. An autoradiograph of a TLC plate shows CAT activity in extracts from three different human lung cancer cell lines transfected using various cationic liposomes. The lung cancer cell lines NCI-H69, NCI-H82, and NCI-HS20 were plated at $2 \times 10^6$ cells/plate and transfected in suspension. Individual plates of cells were transfected with 5 µg of RSV-CAT (RC) alone or 5 µg of RSV-CAT complexed to a total of 10 or 20 nmole of pure DOTMA (D), pure L-PE (L), or L-PE/CEBA (L/CA) liposomes. The cells were harvested 48 h after transfection and assayed for CAT activity.

Example 11 Efficient Transfection of a variety of Human Lung Cancer Cell Lines using Cationic Liposome-mediated Delivery of DNA (see FIG. 21)

Figure 8A:
Figure 8B:

Example 12 Transfection of Lung Cancers in Mice by Intravenous Injection of Cationic Lipid Carrier:DNA Complexes (see FIG. 8 A, B)

Figure 12E:
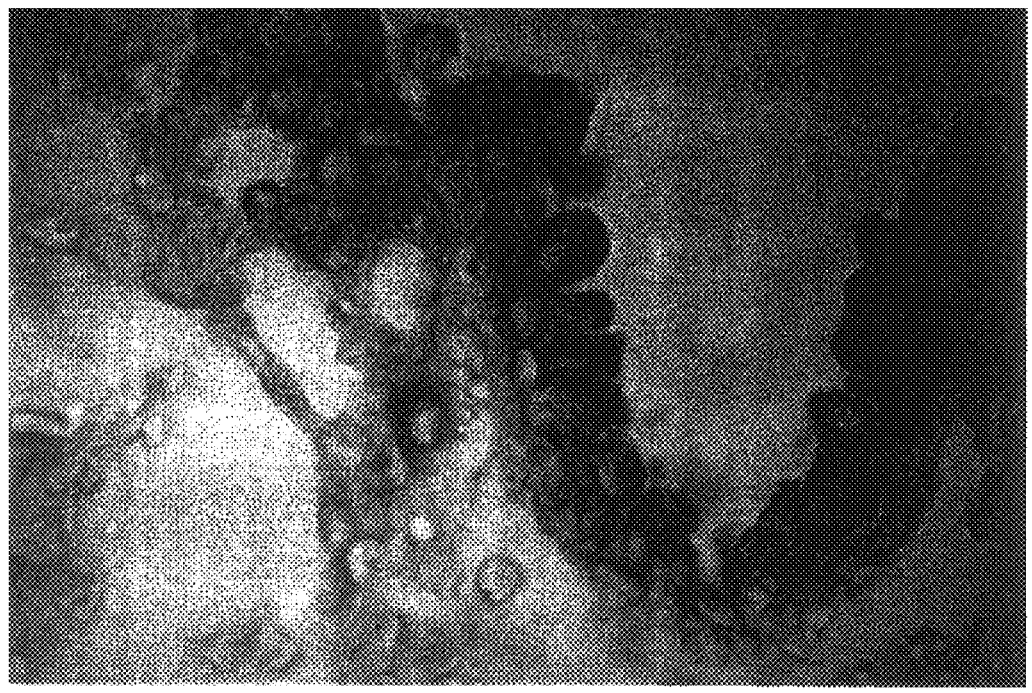

Example 13 Demonstration of High Level CAT Gene Expression in Multiple Tissues after Intravenous (iv) Injection of pZN27 alone, or pZN27:DDAB:Cholesterol SUV Complexes Example 14 Induction of High Levels of Human Interleukin-2 in the Spleen and Lymph Nodes of Mice by Intravenous Injection of Cationic Lipid Carriers Complexed to a CMV-Interleukin-2 Gene Example 15 Induction of High Level Expression of the Human CFTR Gene in Mice Treated by iv Administration of pZN32:Cationic Lipid Carrier Complexes (see FIG. 12E)

Figure 15:
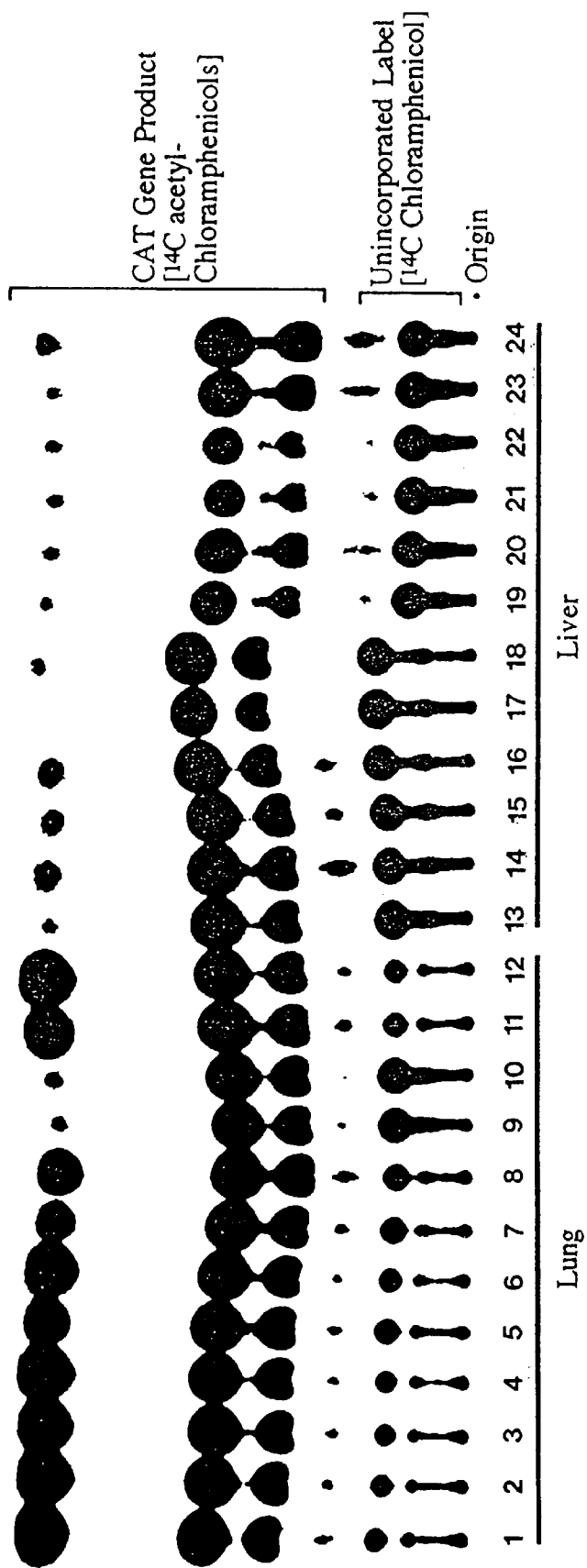
FIG. 15 shows an autoradiograph of the thin layer chromatograph of the a CAT assay for six different plasmids injected intravenously in mice. Lanes 1–12 show the CAT activity in lung tissue; Lanes 13–24 show the CAT activity in liver tissue. Lanes 1, 2, 13, 14-pZN51; lanes 3, 4, 15, 16-pZN60; lanes 5, 6, 17, 18-pZN61; lanes 7, 8, 19, 20-pZN62; lanes 9, 10, 21, 22-pZN63; lanes 11, 12, 23, 24-pZN27. Lipid carriers were DDAB:Cholesterol (1:1). Lipid carriers-DNA complexes were 5 nmoles cationic lipid to 1 µg DNA. 100 µg DNA was injected per mouse. Animals were sacrificed after 48 hrs. Each lane represents a single mouse. Chromatograph runs from bottom to top of Figure as shown. As shown by the brackets in FIG. 15, unreacted $^{14}$C chloramphenicol only migrates a short distance from the origin of the TLC plate. The $^{14}$C Acetylated chloramphenicol species migrate which result from CAT enzymatic activity further up the plate as shown by the brackets.

Example 16 Demonstration of CAT Gene Expression in Lung and Liver after Intravenous Injection of Different CAT Gene-Containing Plasmids (see FIG. 15)

Example 17 Generalized versus Tissue and Cell Type-specific CAT Gene Expression produced by iv Injection of CMV-CAT-Liposome or CFTR-CAT-Liposome Complexes, respectively (see FIG. 16 A–K)

Figure 19A:
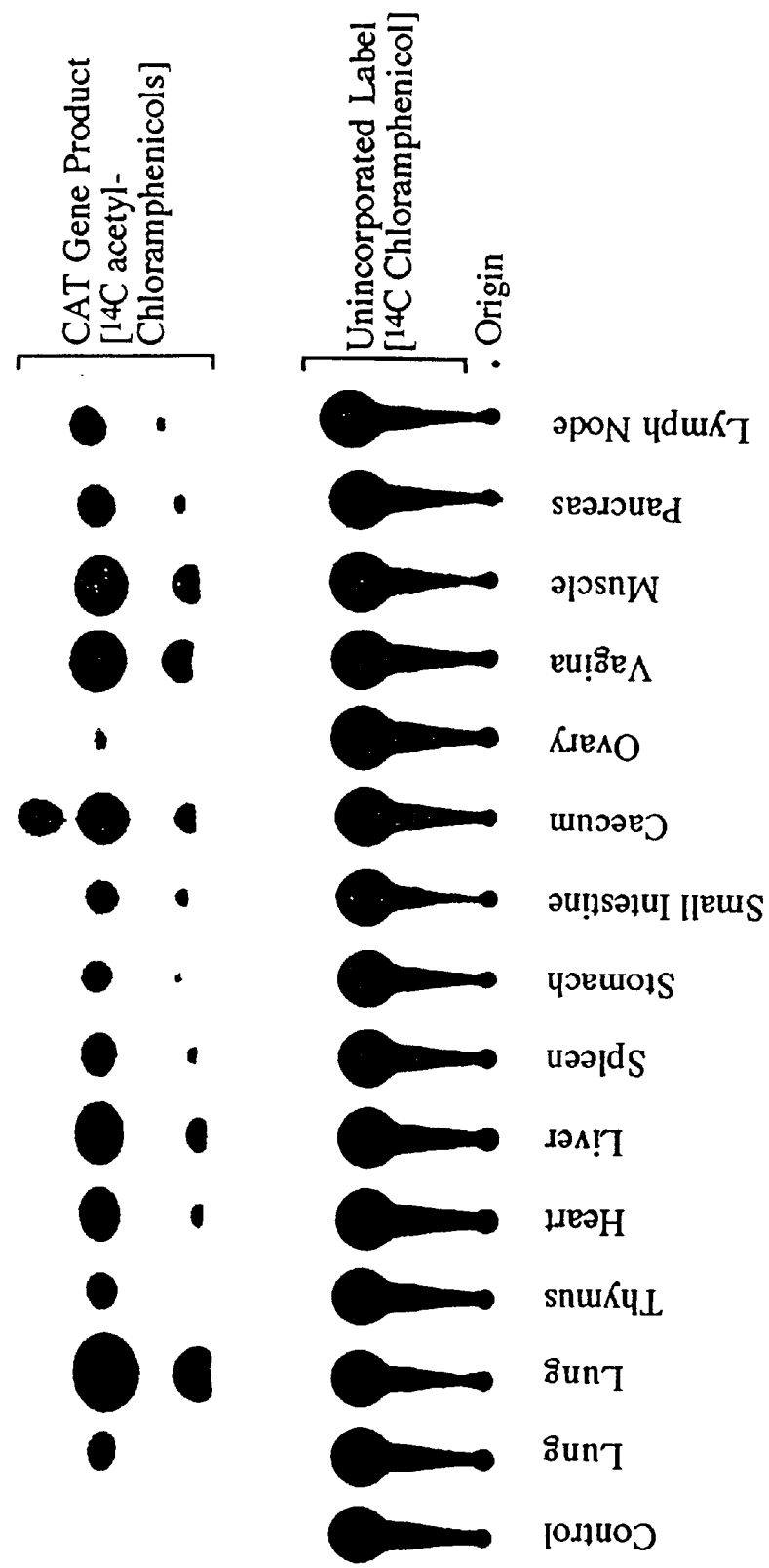
FIG. 19A shows an autoradiograph of a TLC plate showing CAT activity in animals after injection of pZN27 without any lipid carrier. One milligram was injected iv twice over a 4-hour period. Mice were sacrificed 24 hrs. later. The various tissues examined are indicated under each lane.
Figure 19B:
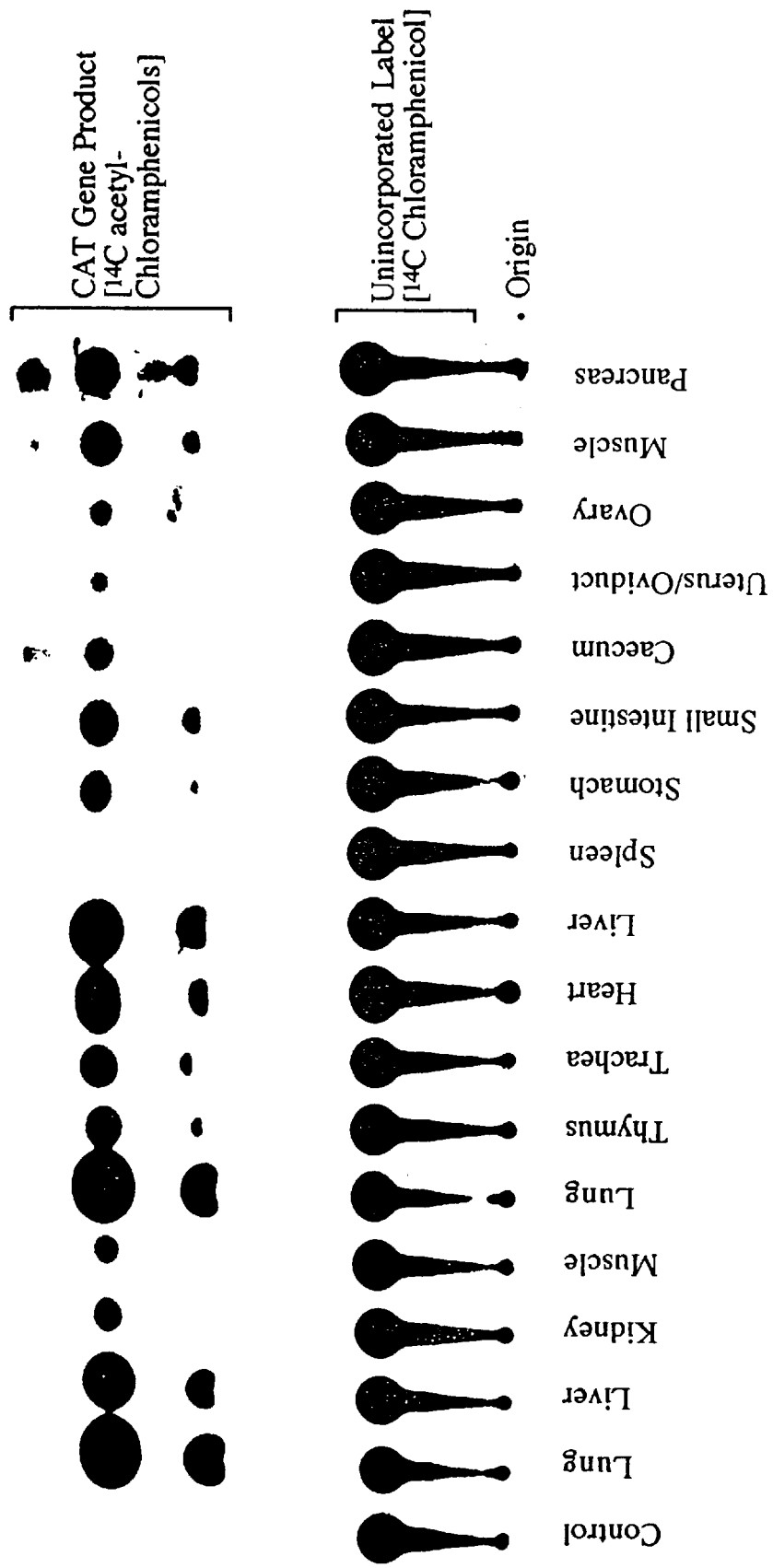
FIG. 19B shows an autoradiograph of a TLC plate showing CAT activity in an animal injected with pZN27 complexed with a lipid carrier. Lipid carrier was DDAB:Cholesterol 1 to 1 molar, 5 µg of plasmid complexed to 1 nmole of lipid. 100 µg was injected iv, and animals were sacrificed 24 hrs later. The various tissues examined are indicated under each lane.

Example 18 Comparison of Transfection Focusing on iv Injection of Plasmid alone with iv Injection of Plasmid Complexed to a Lipid Carrier (see FIG. 19 A,B)

Figure 17A:
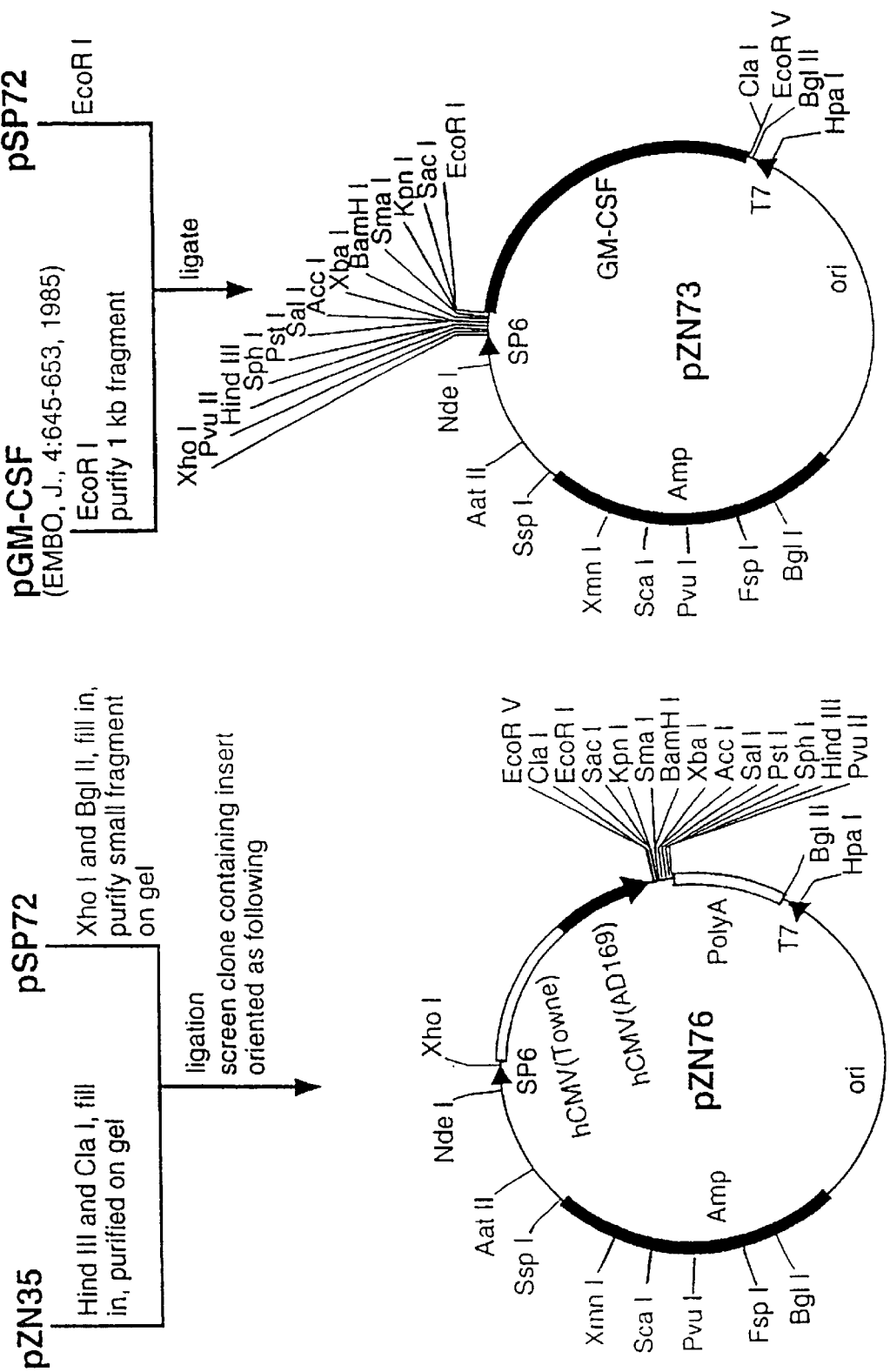
FIG. 17 shows the construction of plasmid pZN84, encoding murine GM-CSF.
Figure 17B:
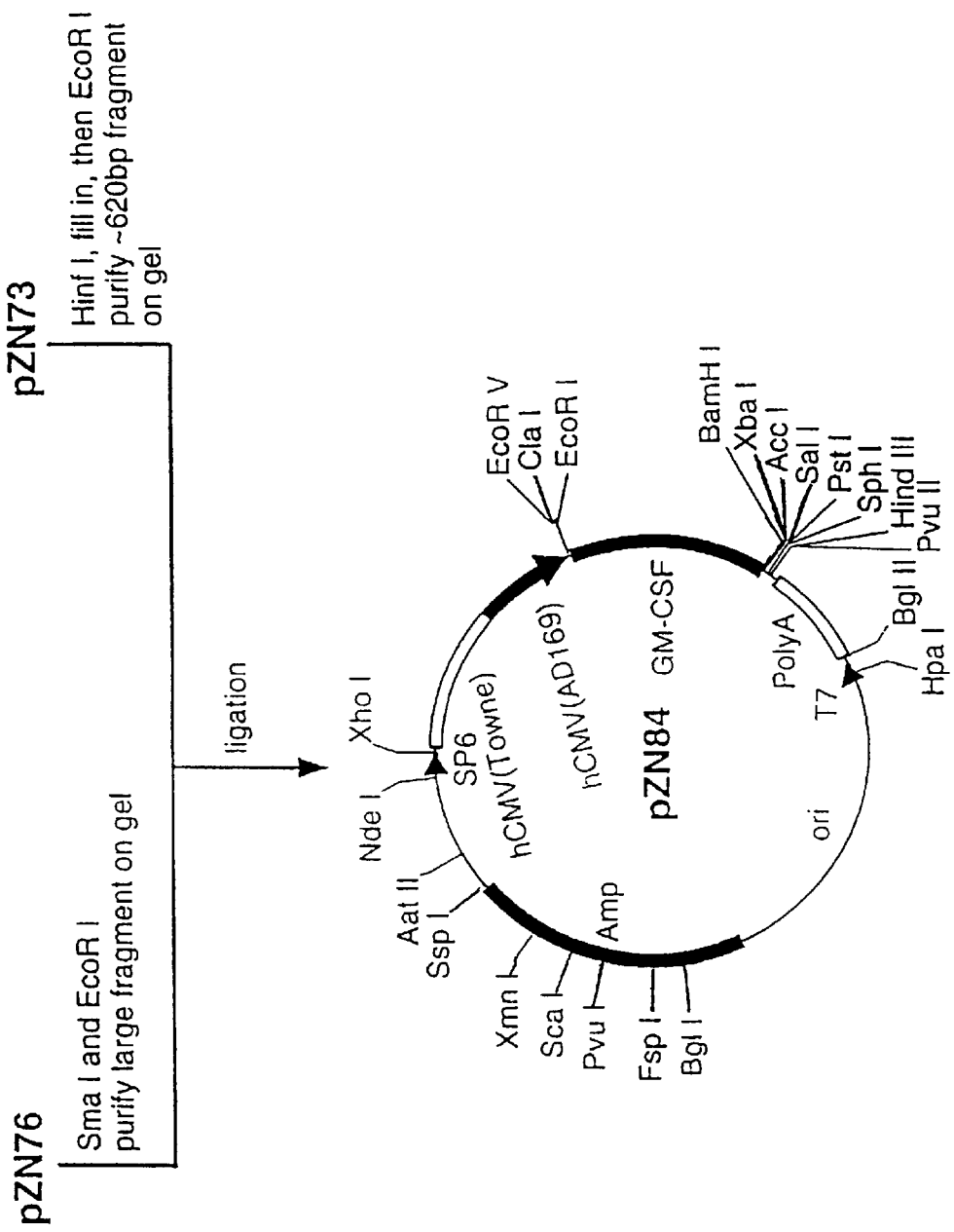
Figure 18:
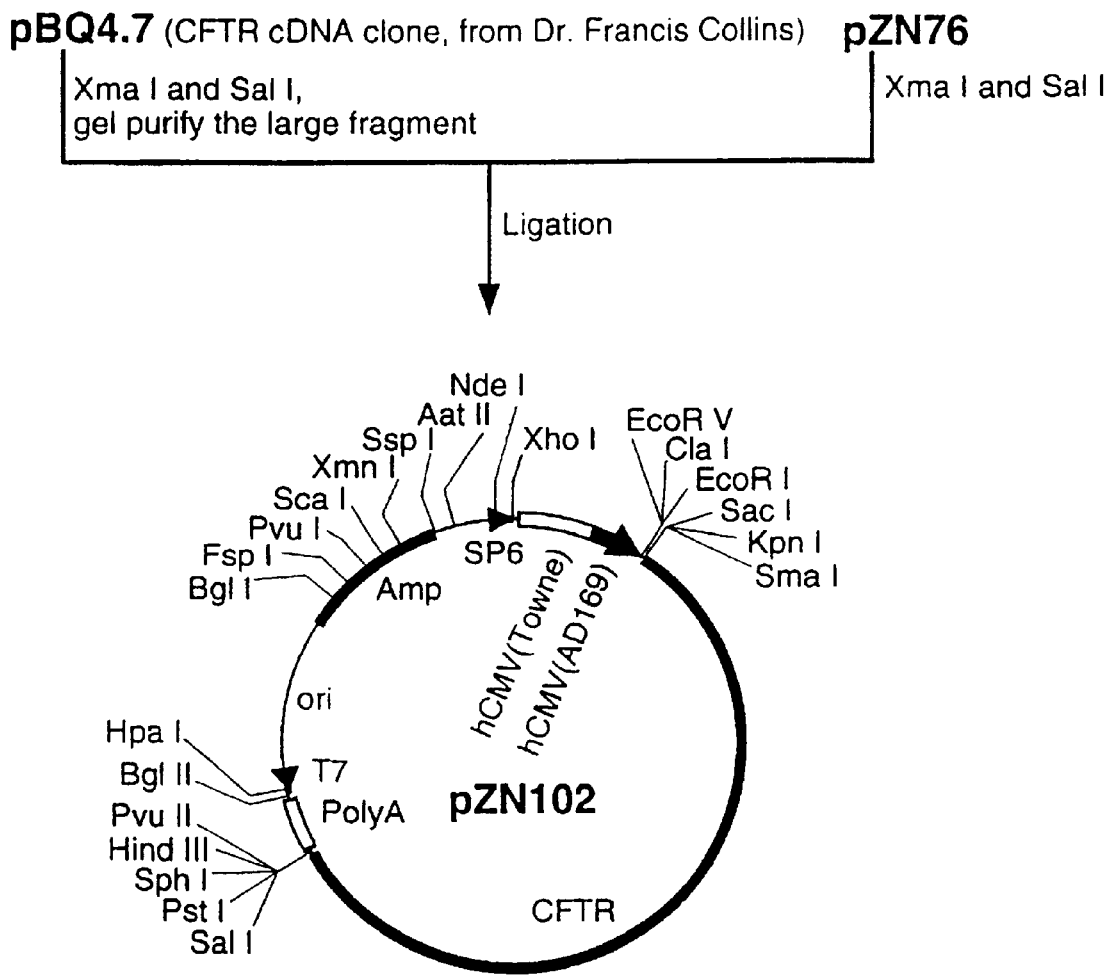
FIG. 18 shows the construction of pZN102, encoding human CFTR.

Example 19 IV Injection of GM-CSF Expression Plasmid-Cationic Liposome Complexes Produces Significant Antitumor Effects pZN84 (see FIG. 17)

Figure 22:
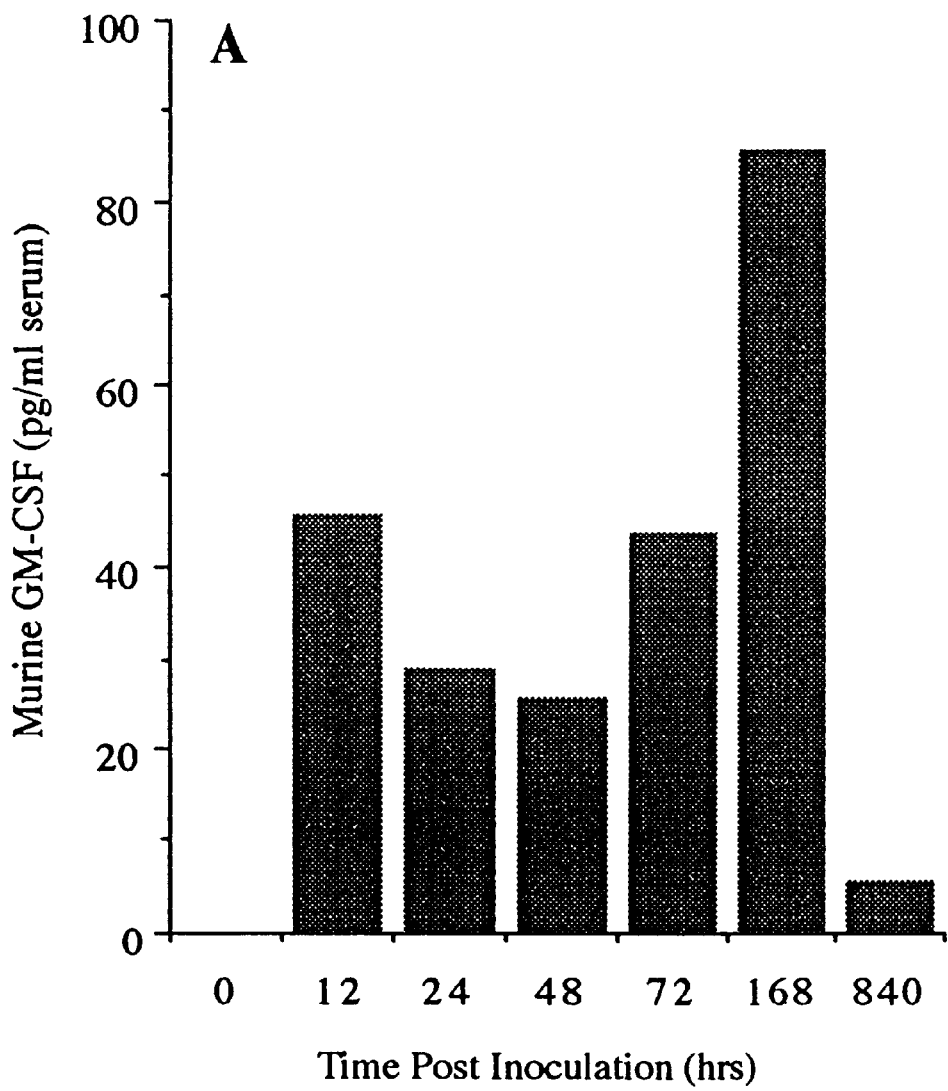
FIG. 22 shows serum murine GM-CSF levels in a single goat (A) injected iv with 1 mg of GM-CSF plasmid (pZN84) complexed with DDAB:Cholesterol liposome (1 µg plasmid to 1 nmole lipid). Serum samples were collected at 0, 12, 24, 48, 72, 168, and 840 hrs. after injection. Murine GM-CSF levels were measured by ELISA using a commercial kit (Endogen).
Figure 23:
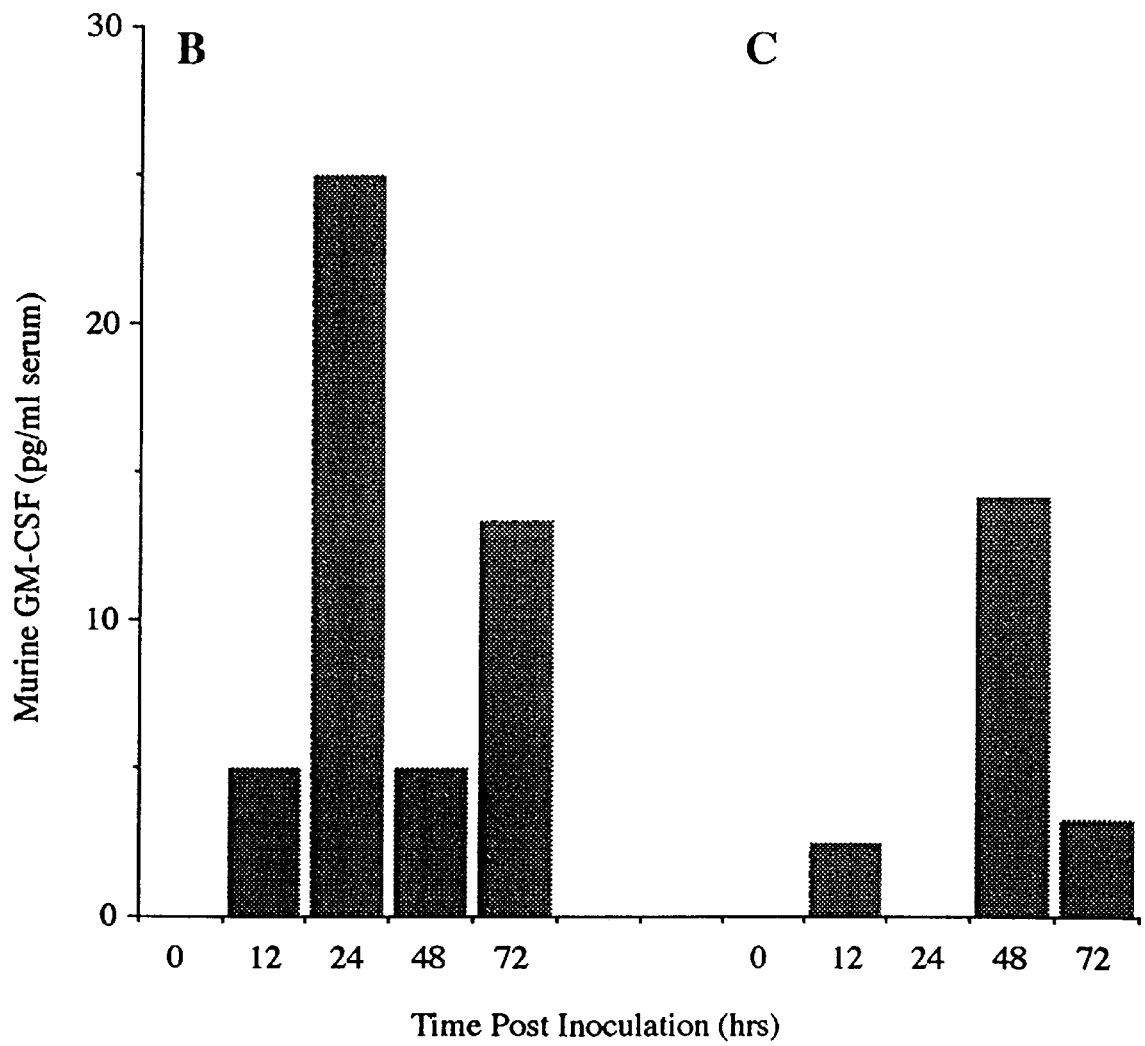
FIG. 23 show the serum murine GM-CSF levels in two additional goats (B and C) injected with pZN84 as per goat A.

Example 20 Prolonged, High Level Murine GM-CSF Gene Expression in in vivo after Intravenous (iv) injection of pZN84 complexed to DDAB:Cholesterol (1:1) Liposomes into Goats (see FIGS. 22, 23)

Figure 20:
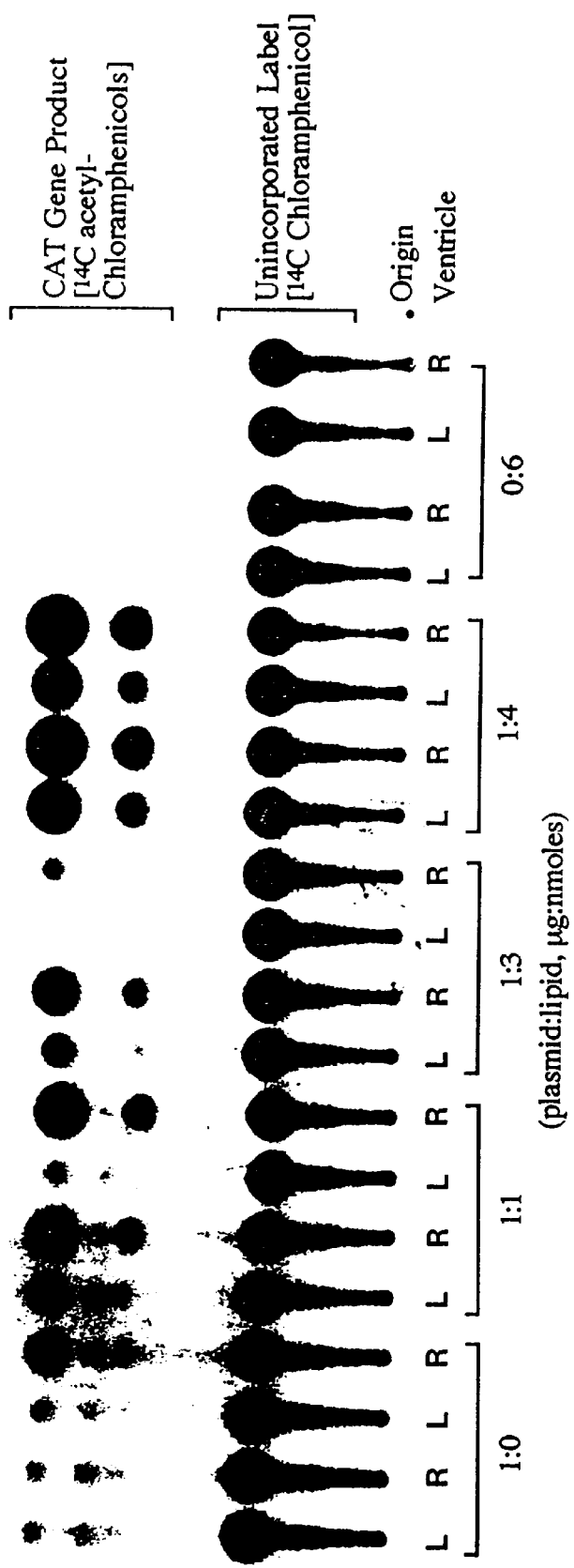
FIG. 20 shows an autoradiograph of a TLC plate of injection into the right (R) ventricle of pCIS-CAT complexed to DOTMA:DOPE (1:1) lipid carriers in the indicated ratios of plasmid:lipid. Animals were sacrificed 48 hrs. after the stereotactic injection of 2.5 µg. Each pair of lanes represents a single animal. The left (L) ventricle was not injected and therefore transfection of the left ventricles demonstrates that the entire brain is being transfected.

Example 21 Influence of Liposome-GM-CSF Plasmid Complex on the Course of Experimental Viral Pneumonia in Mice Example 22 High Level Expression of the CAT Gene in Mouse Brain produced by Injection of DNA alone or DNA-Cationic Liposome Complexes directly into the Central Nervous System (see FIG. 20).

Example 23 Demonstration of CAT Gene Expression in the Lung after Intravenous (iv) Injection of pRSV-CAT:L-PE:CEBA Complexes Example 24 Demonstration of CAT Gene Expression in Multiple Tissues after Intravenous (iv) Injection of pZN20-CAT:DDAB:DOPE Complexes Example 1

Preparation of Plasmids for in vivo Gene Therapy

Figure 9A:
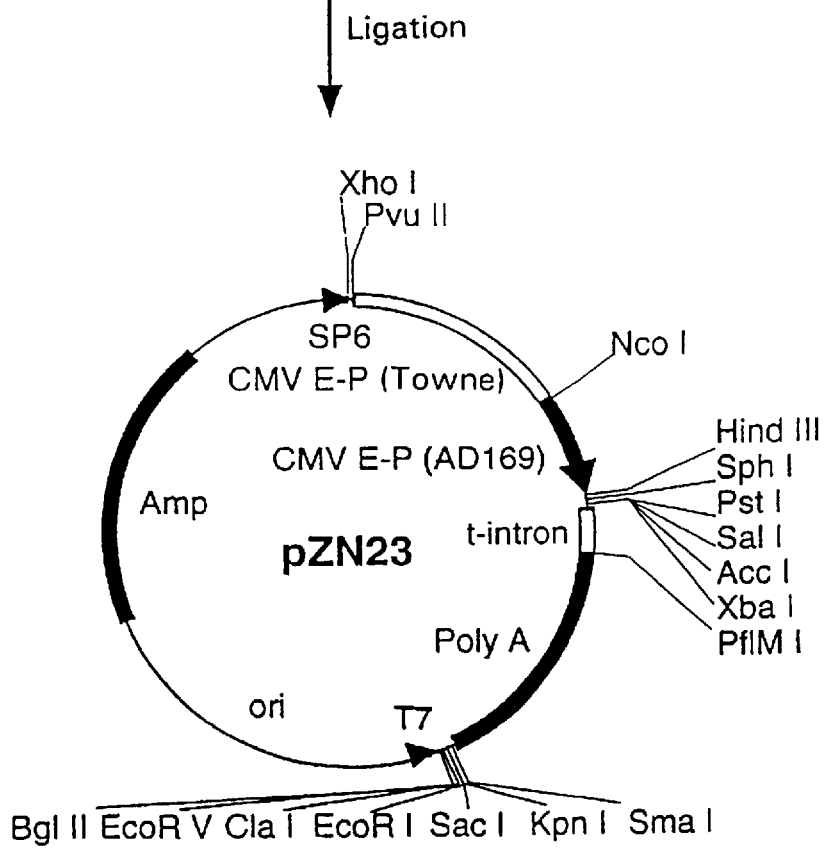
FIG. 9 shows the construction of plasmid pZN27, encoding CAT.
Figure 9B:
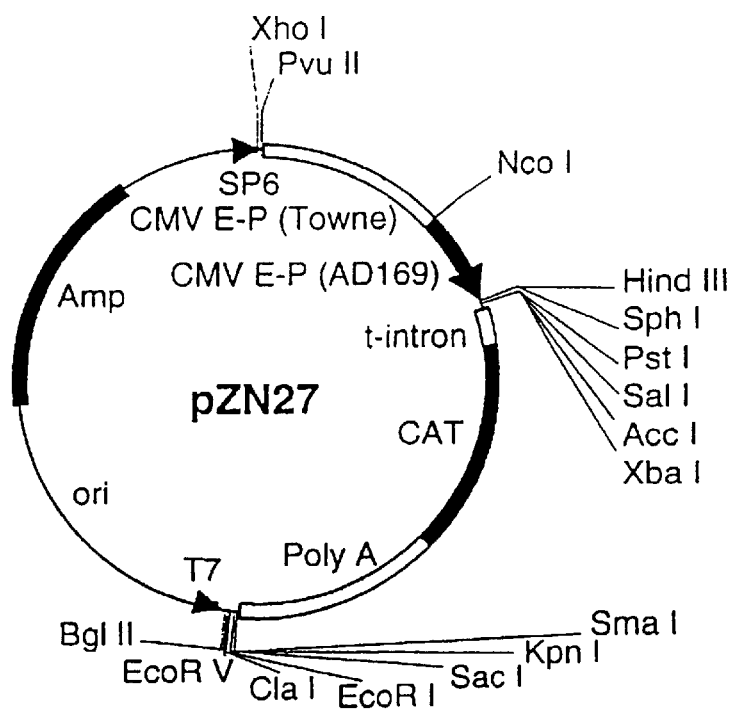
Figure 10A:
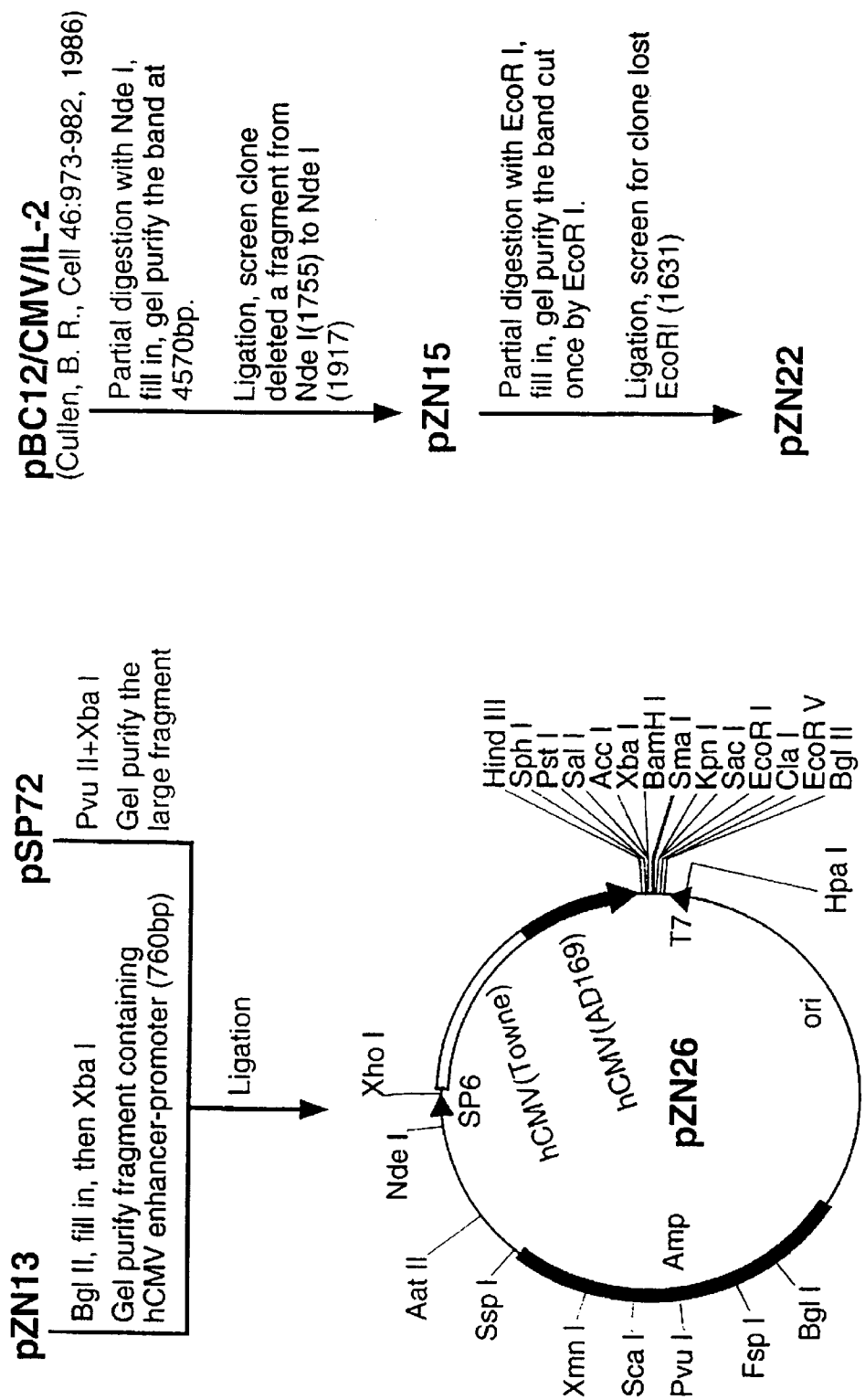
Figure 10B:
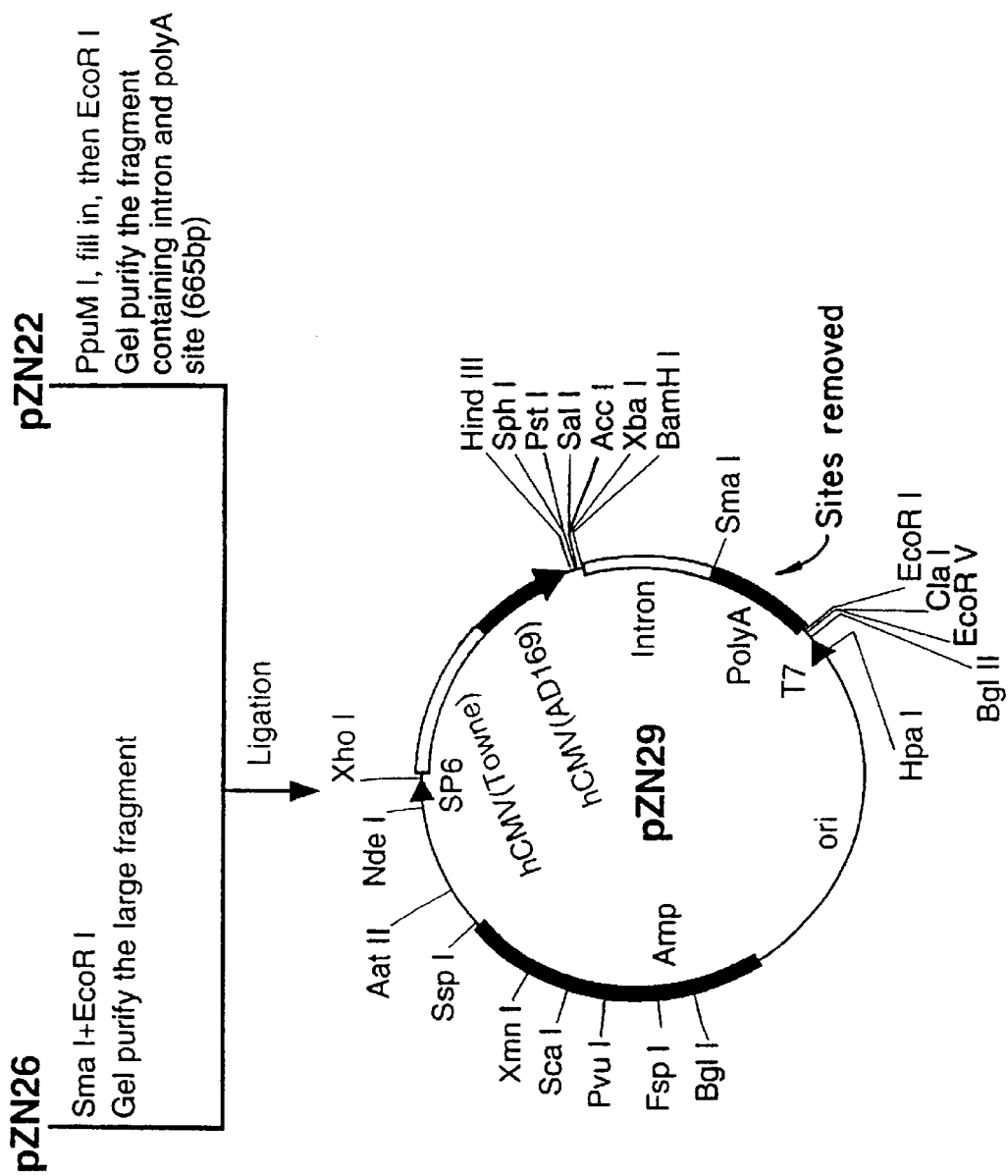
Figure 10C:
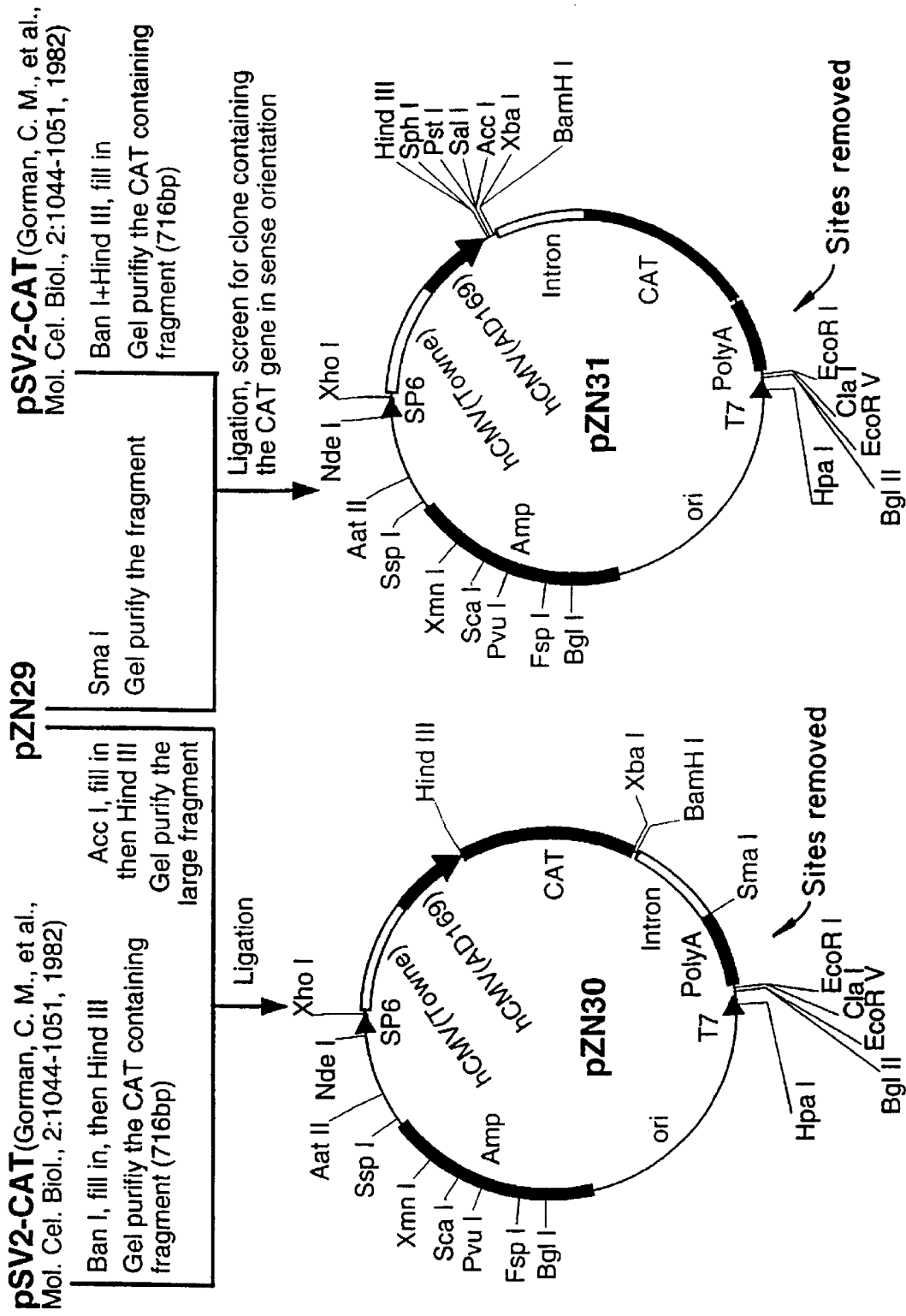
Figure 13A:
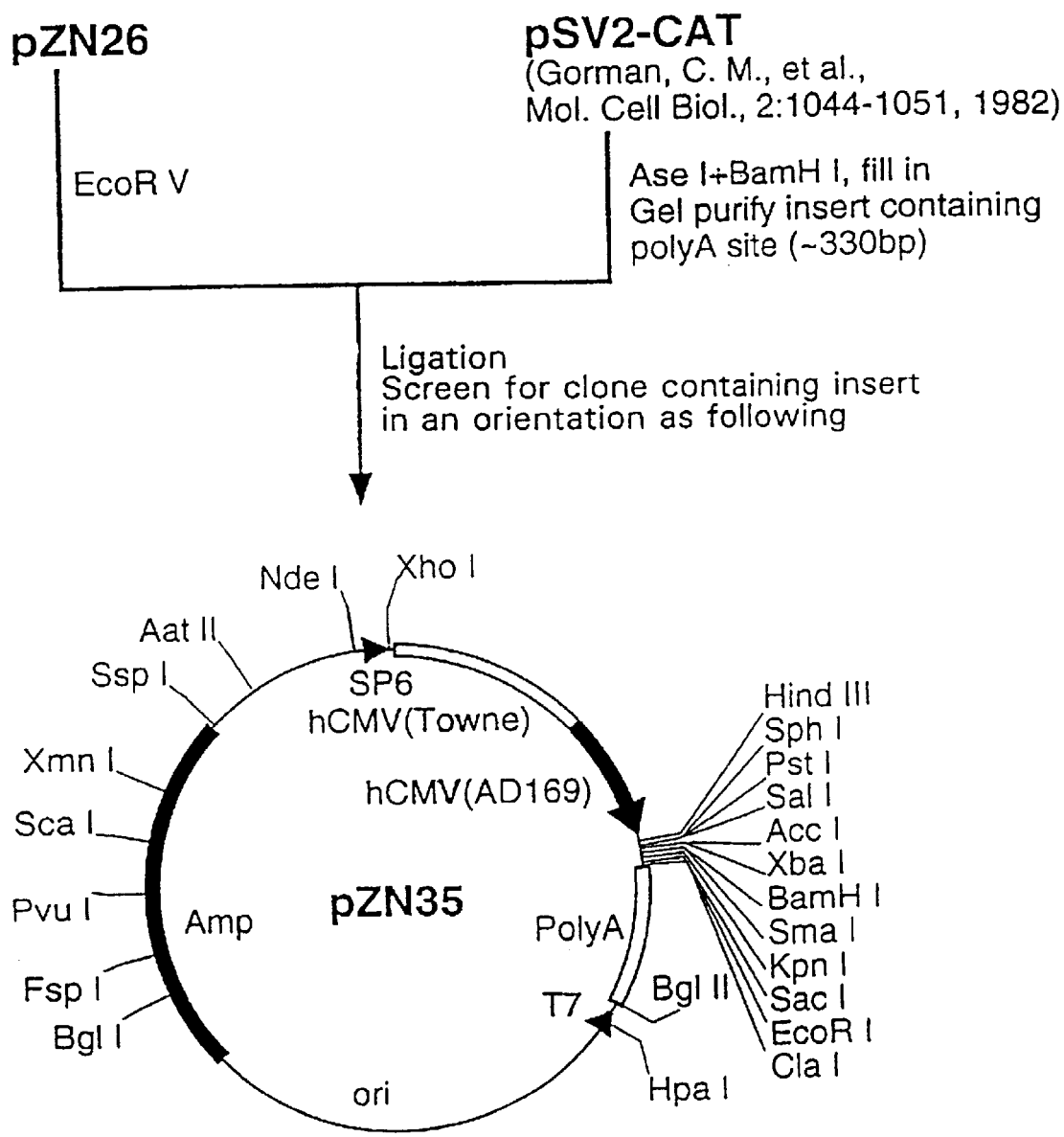
FIG. 13 shows the construction of plasmid pZN51, encoding CAT.
Figure 13B:
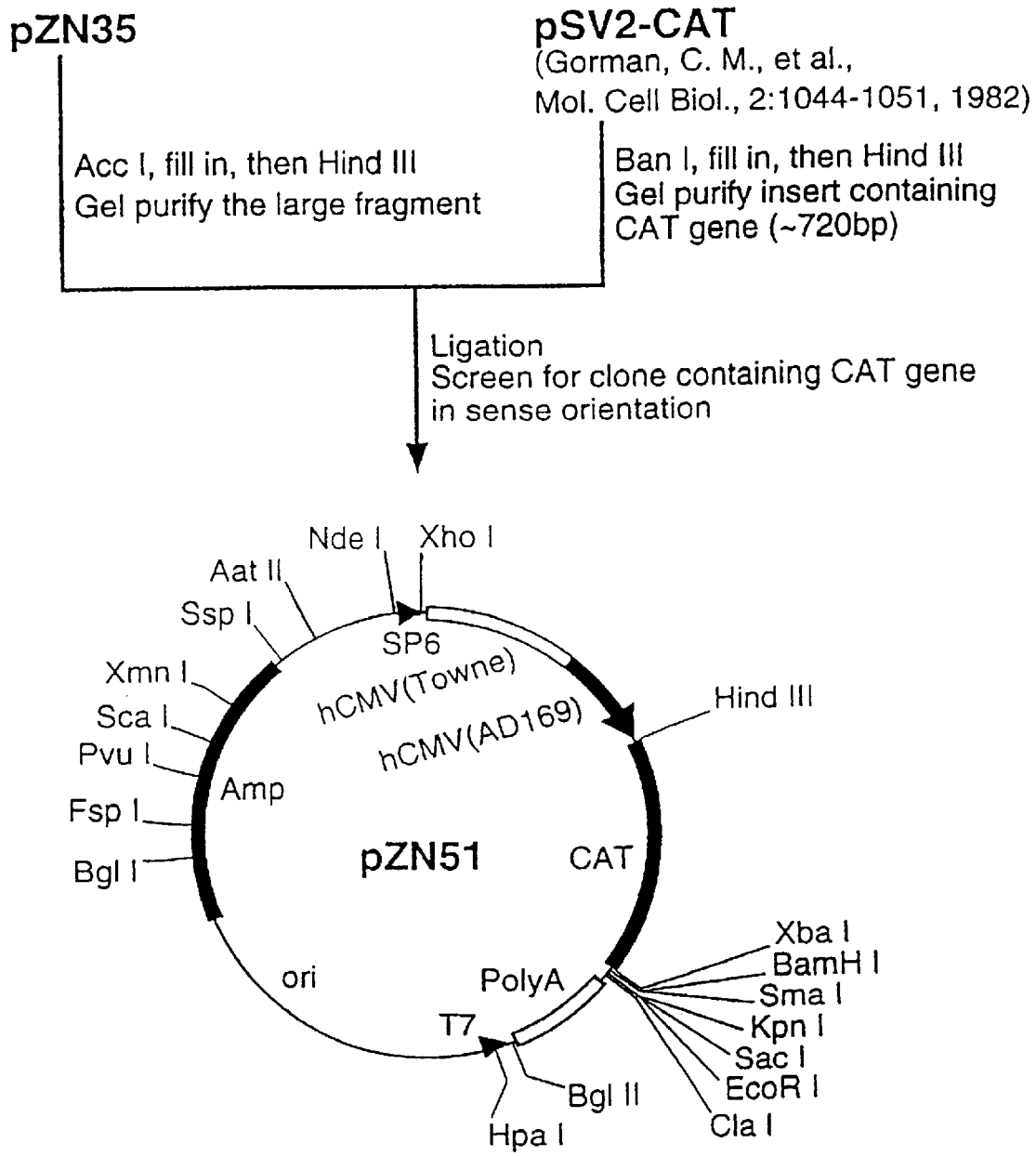
Figure 14A:
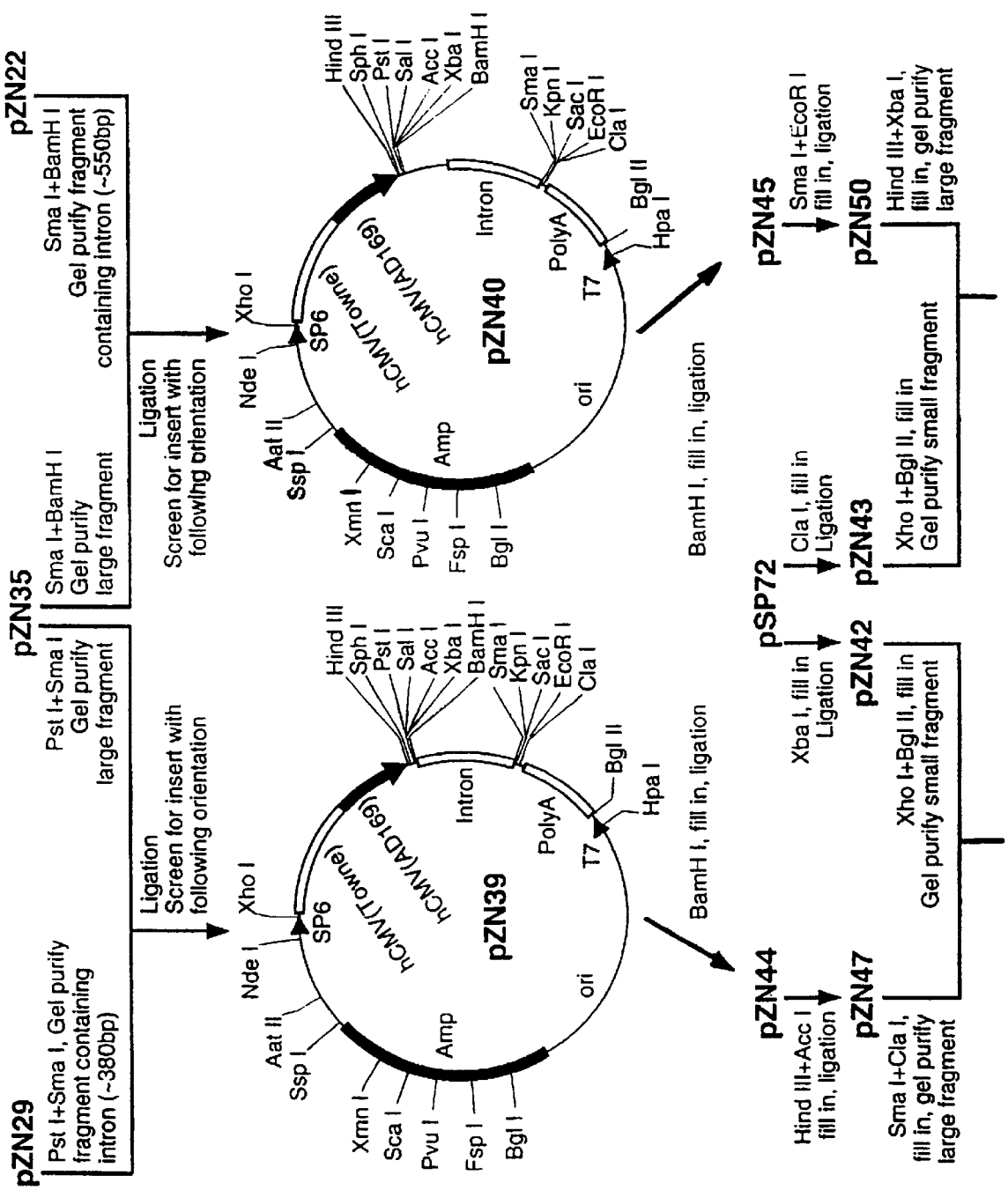
FIGS. 14A through 14C show the construction of intermediate plasmids pZN52, pZN54, pZN56 and pZN58.
Figure 14B:
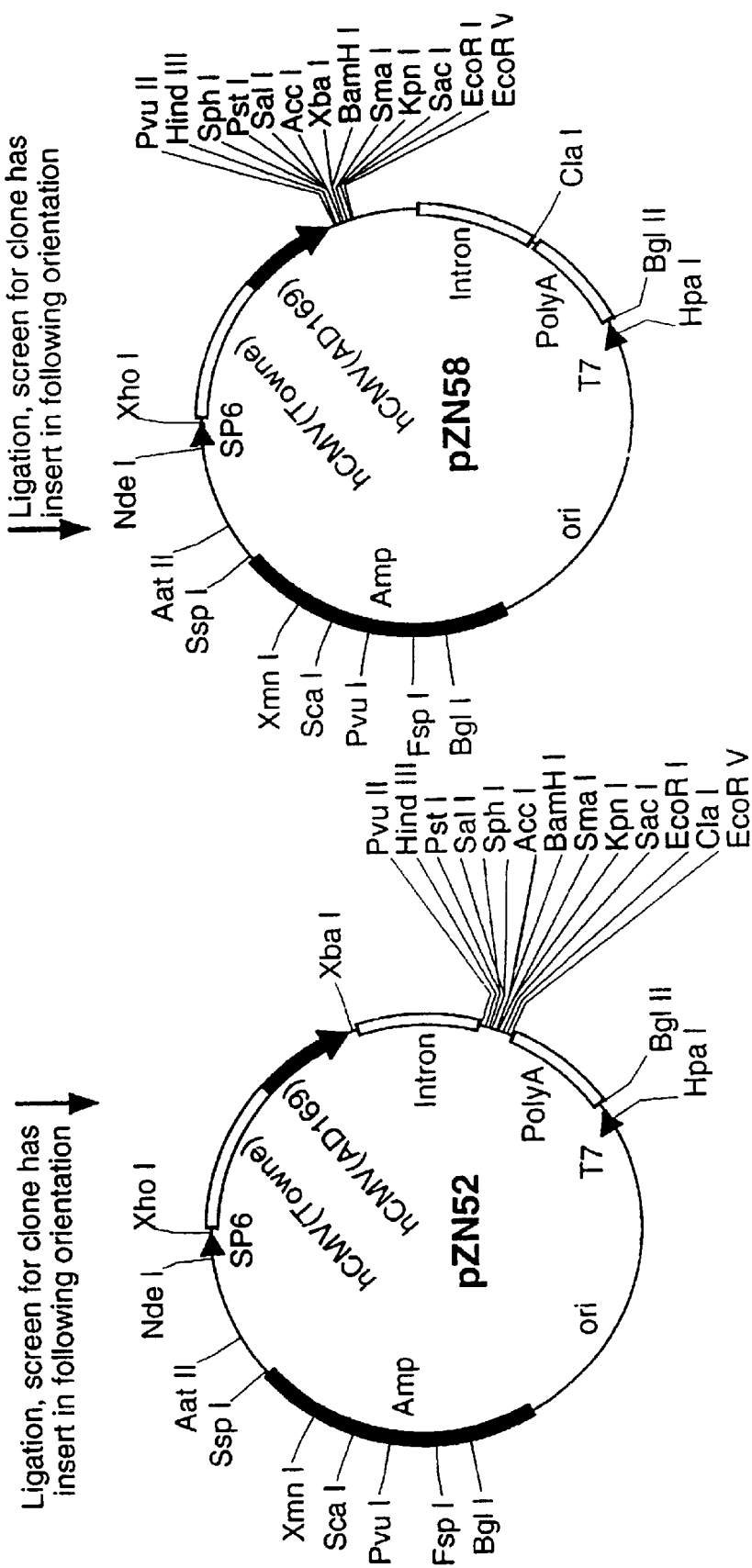
Figure 14C:
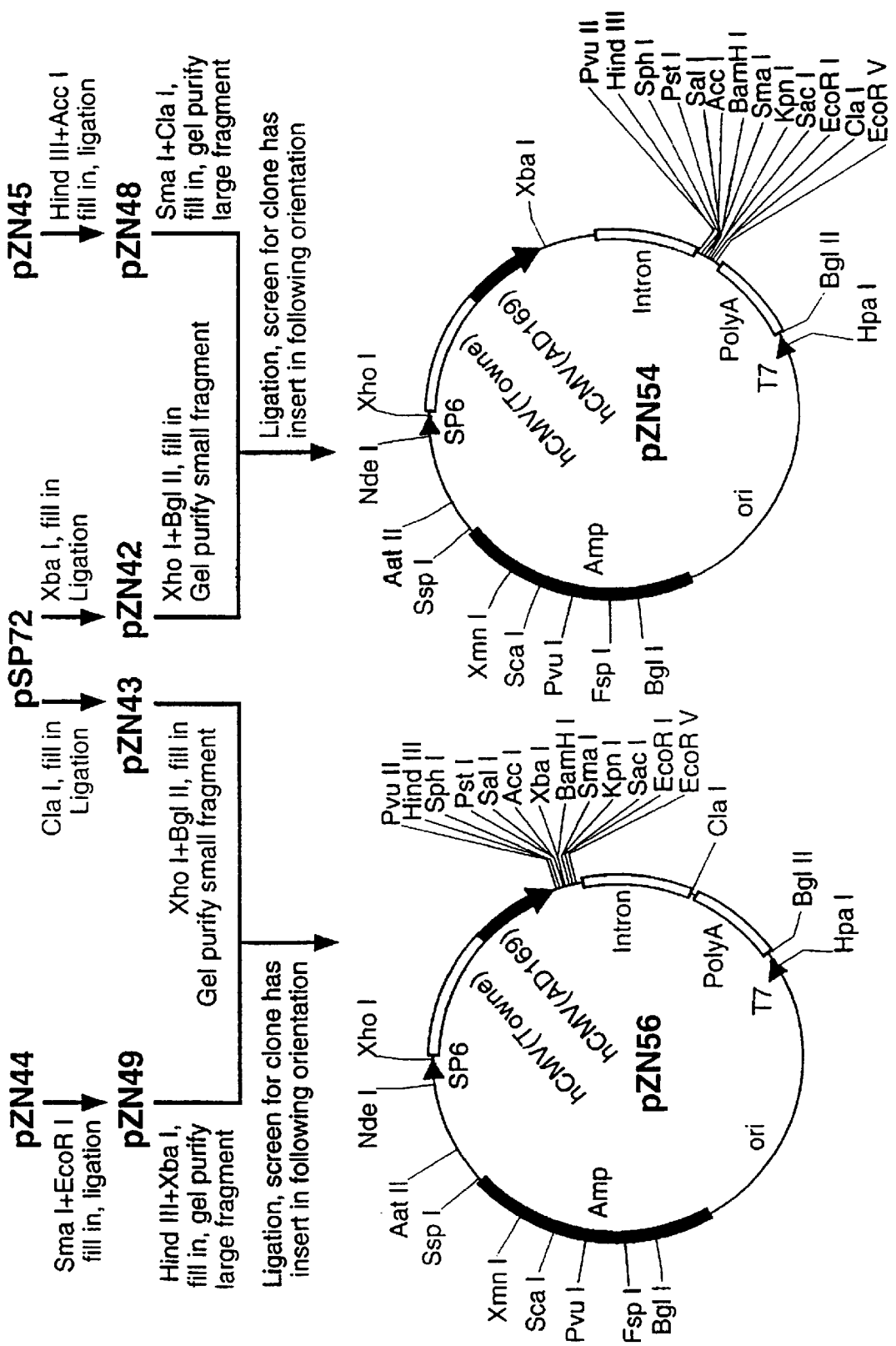
Figure 14D:
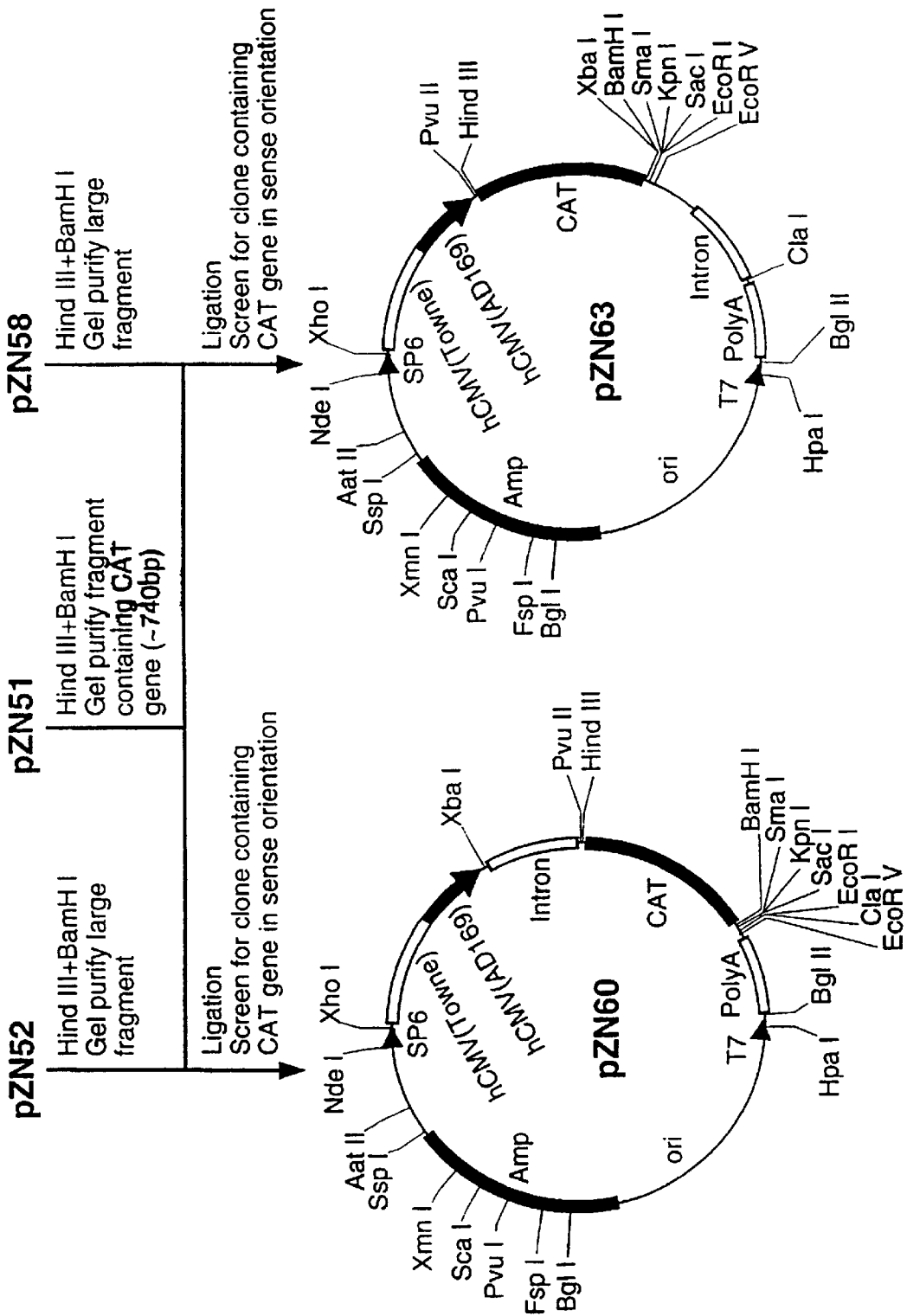
FIGS. 14D through 14E show the construction of the final plasmids, pZN60 through pZN63, from the intermediates.
Figure 14E:
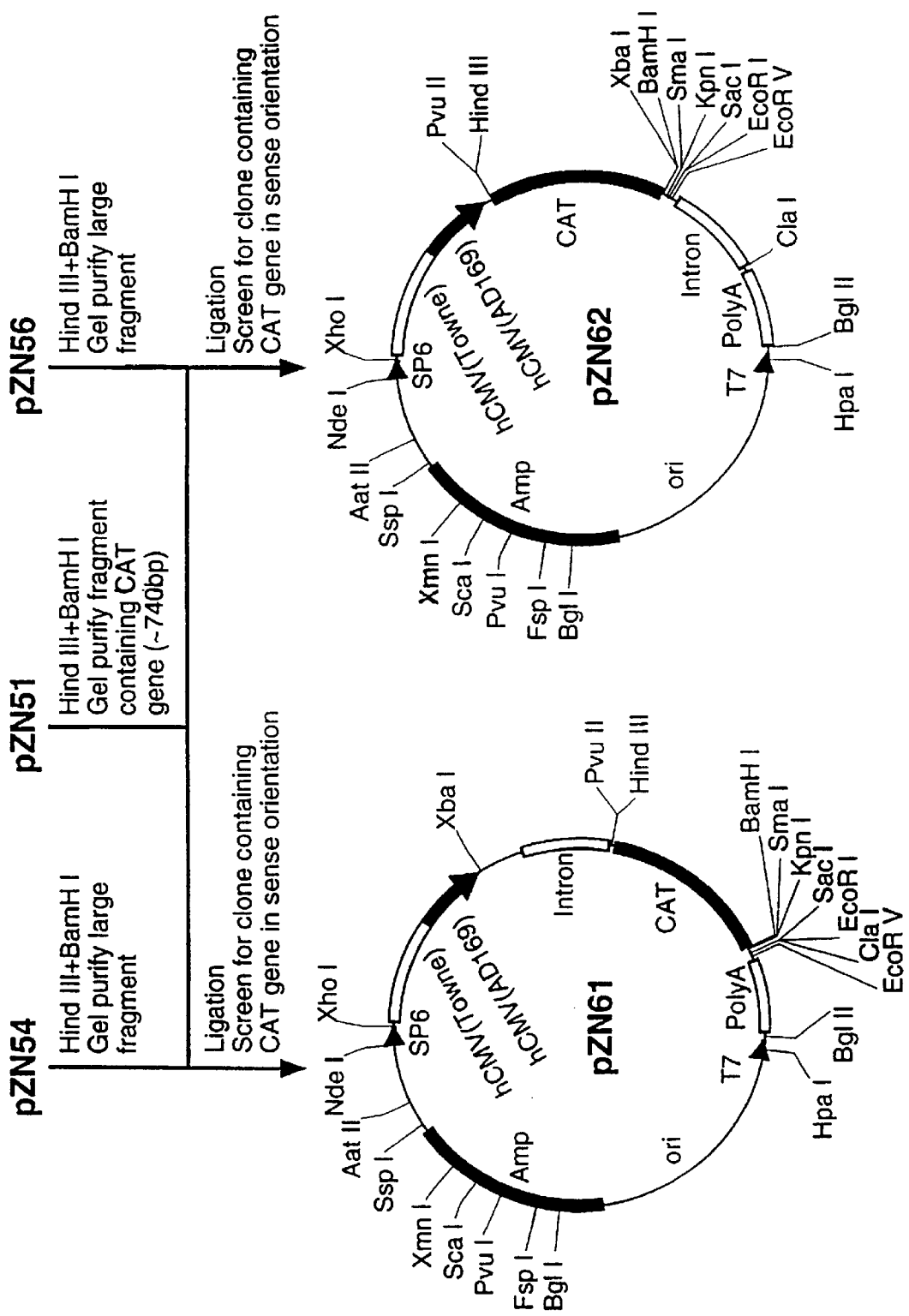

Details regarding the plasmids that have been used for transfection of mammalian cells are as follows.

pRSVCAT: construction of this plasmid is described in Gorman et al., (1982) *Proc. Nat. Acad. Sciences* (*USA*) 79:6777–6781. In the pRSVCAT plasmid, the 3'-RSVLTR is juxtaposed as a promoter upstream from CAT encoding sequences. The distance between the LTR transcriptional start site and the CAT initiation codon (the first AUG downstream from the start site) is about 70 bp.

p5'PRL3-CAT: construction of this plasmid is described in Sakai et al., (1988) *Genes and Development* 2:1144–1154.

pSIS-CAT: construction of this plasmid is described in Huang and Gorman, *Nucleic Acids Research*, (1990) 18:937–948.

pZN20: construction of this plasmid is illustrated in FIG. 5. The plasmid was prepared as follows. pCATwt760 (Stinski and Roehr, (1985) *J. Virol.* 55:431–441) was treated with HindIII and the fragment containing the HCMV IE 1 enhancer and promoter element purified. The isolated fragment was then cloned into the HindIII site of pSP72 (Promega) creating pZN9. Clones were screened in which the enhancer and promoter element is as shown in FIG. 5. Following partial HindIII digestion of pZN9, the blunt ends were filled in with DNA polymerase I Klenow fragment. The resulting clone pZN12 had lost the HindIII site 5' to the enhancer and promoter element. pZN12 was then treated with NcoI and HindIII and the large NcoI-HindIII fragment purified and ligated to a purified small NcoI-HindIII fragment from pBC12/CMV/IL-2 (Cullen, (1986) *Cell* 46:973–982. pBC12/CMV/IL-2 contains the HCMV promoter from the AD169 strain. The resulting clone was pZN13. pZN13 was partially digested with BamHI, filled in with DNA polymerase I Klenow fragment and the resulting clones screened for the clone which had lost the BamHI site at the 5' end of the enhancer and promoter element. The resulting clone was called pZN17. pZN17 was treated with HindIII and BamHI and the resulting HindIII-BamHI large fragment was purified and ligated to a purified small HindIII-BamHI fragment obtained from pSV2-CAT (Gorman, et al., (1982), *Molecular Cell Biology* 2:1044–1051). The resulting clone was pZN20. The full restriction map of HCMV (Towne) is shown in FIG. 6A. HCMV (AD169) is shown in FIG. 6C. A comparison of the two promoters is shown in FIG. 6B. Significantly more expression is obtained when a promoter from the AD169 strain is used as compared to one from the Towne strain. pZN20 contains a composite promoter which has the Towne sequence 5' of the NcoI site and the AD169 sequence 3' of the NcoI site. The NcoI site is indicated by the asterisk in FIG. 6B. pZN20 has this composite HCMV promoter followed by the CAT gene, SV40 t-intron and SV40 polyA adenylation site.

pZN27: Construction of this plasmid is illustrated in FIG. 9. pZN27 contains the composite HCMV promoter followed in order by the SV40 t-intron, the CAT coding sequence and the SV40 polyA adenylation site.

pZN46: Construction of this plasmid is shown in FIG. 10A and FIG. 10B. pZN46 contains the composite HCMV promoter, followed by the human IL-2 gene, rat preproinsulin 2 intron and polyA addition site from the rat preproinsulin 2 gene. These last three components were derived from the pBC12/CMV/IL-2 plasmid of Cullen (*Cell*, (1986) 46:973–982. The rat preproinsulin 2 intron was modified by deleting an internal 162 base pair NdeI fragment.

pZN32: Construction of this plasmid is shown in FIG. 11. pZN32 contains the composite HCMV promoter followed in order by the modified rat preproinsulin 2 intron described for pZN46, human CFTR cDNA, and rat preproinsulin 2 gene polyA addition site as described for pZN46. CFTR cDNA was obtained from pBQ4.7 from F. Collins (Univ. of Michigan).

pZN51: Construction of this plasmid is shown in FIG. 13. pZN51 contains the composite HCMV promoter followed by the CAT coding sequence and the SV40 polyA adenylation site.

pZN60, pZN61, pZN62, pZN63: Construction of these plasmids is shown in FIG. 14. pZN60 contains the HCMV composite promoter followed by the modified rat preproinsulin 2 intron, the CAT coding sequence, and the SV40 polyA addition site. pZN61 is identical to pZN60 but contains an additional 166 base pairs 5' to the intron. This additional DNA is the 166 base pairs immediately 5' of the intron in the pBC12/CMV/IL-2 plasmid and contains rat preproinsulin 2 gene coding sequence. pZN62 is similar to pZN60 except that the intron is 3' of the CAT coding sequence rather than 5' as in pZN60. pZN63 is identical to pZN62 except for the additional 166 base pairs 5', to the intron. This is the same additional sequence described for pZN61.

pCIS-CAT: This plasmid was made as described in Huang, M. T. F. and Gorman, C. M., (1990) *Nucl. Acids Res.* 18:937–947, with the exception that a CMV promoter and a hybrid intron sequence were used rather than the SV40 promoter in the plasmid pML.I.CAT, Gorman, et al., (1990) DNA Protein Eng. Tech., 2:3–10.

Example 2

Preparation of Lipid Carriers and DNA Complexing with Lipid Carriers

Lipid carriers containing a cationic lipid, such as N-[(1-2-3-dioleyloxy) propyl]-N,N,N-triethylammonium chloride (DOTMA), dimethyl dioctadecyl ammonium bromide (DDAB), or 1,2-dioleoyloxy-3-(trimethylammonio)propane (DOTAP) or L-lysinyl-phosphatidylethanolamine (L-PE) and a second lipid, such as dioleoylphosphatidylethanolamine (DOPE) or cholesterol, were prepared as follows.

Preparation of Lipid Carriers:

Lipids, e.g. DDAB, L-PE, cholesterol-ester-β-alanine (CEBA), DOTAP, and cholesterol (Chol) were dissolved in chloroform. Proper amounts of each lipid (determined by the desired molar ratio of each lipid in the final lipid carrier formulation usually 1 to 1 moles cationic lipid to moles non-cationic lipid but ranging from 5 to 1 up to 1 to 5) were mixed together and evaporated to dryness on a rotary evaporator. The lipid film was then resuspended by vortexing after the addition of 5% dextrose in water or lipid carrier buffer (25 mM Tris-HCl pH 7.4, 100 $\mu$M ZnCl$_2$, NaCl to isotonicity. To make a final lipid concentration of 20 mM of multi-lamellar vesicles (MLV). For the preparation of small unilamellar vesicles (SUV), the mixture was then sonicated in a bath sonicator for 15 min, and the lipid carriers were stored under argon at 4° C. until use.

Plasmid Preparation:

The E. coli strain HB101 which carried the plasmid was grown in TB at 37° C. The method of plasmid purification is a modification of the protocol of "lysis by alkali" and "purification of plasmid DNA by precipitation with polyethylene glycol" described by Sambrook et al., (1989) (*Molecular Cloning*, 2nd edition, Cold Spring Harbor Laboratory Press). The modification was that the precipitation of DNA by PEG was omitted. The final DNA preparation was dissolved in 10 mM Tris-HCl pH 8.0.

Preparation of Lipid Carrier-plasmid Complexes:

Plasmids were diluted separately in 5% dextrose in water solution to the desired concentration (usually 1 $\mu$g/$\mu$l). The lipid carriers were also diluted in 5% dextrose in water to the same volume as the plasmid.

The amounts of lipid carriers used were determined based on the ratio of nmoles of lipid to $\mu$g of plasmid added, e.g. for lipid carrier:plasmid=1:1, one nmole of cationic lipid is mixed with 1 $\mu$g of plasmid DNA. Plasmid and lipid carriers were then mixed together to form DNA:lipid carrier complexes.

Dose Injected.

At least 50 $\mu$g, and routinely 100 $\mu$g of plasmid DNA complexed to cationic lipid carriers were injected intravenously by tail vein per mouse. For injection of plasmid alone, at least 500 $\mu$g and routinely 2 mg of plasmid DNA were injected intravenously by tail vein per mouse.

Example 3

Demonstration by Immunohistochemistry of CAT Gene Expression in the Lung After Intravenous (iv) Injection of pZN27-DDAB: Cholesterol Lipid Carrier Complexes Lipid Carrier: DDAB:Cholesterol=1:1, stock 20 mM in Lipid Carrier Buffer.

Plasmid: pZN27.

DNA:Lipid carrier Ratio: lipid carrier:plasmid=5 nanomoles cationic lipid:1 $\mu$g DNA DNA dose: 100 $\mu$g plasmid DNA in 200 $\mu$l 5% dextrose in water was injected iv by tail vein per mouse.

Mice: ICR, female, 25 grams.

Immunohistochemical Staining to Detect CAT Protein in Lung Sections of Mice Treated in vivo.

Procedure: Forty eight hours after injection of the pZN27-DDAB:Cholesterol complexes, the lungs are removed, perfused with 33% O.C.T. Embedding Medium (Miles, Inc.), embedded in O.C.T. and snap frozen. Frozen tissues were sectioned at 6 $\mu$m, collected onto glass slides, fixed for 10 minutes in 4° C. acetone and then placed in 0.2% Triton X-100 to permeabilize membranes. Sections were then incubated for 12–48 hours with the monoclonal anti-CAT antibody (available from Dr. Parker Antin, Univ. of Arizona) or isotype negative control antibody at the appropriate dilution. After washing, a biotinylated antibody directed against the primary antibody (Zymed, S. San Francisco) was added for a minimum of 60 minutes, followed by application of the streptavidin-alkaline phosphatase complex (Zymed) for 60 minutes. The substrate-chromogen appropriate for the enzyme label was then applied, per the manufacturer's instructions. Slides were coverslipped in water-soluble mounting media for examination.

Results: The results are shown in FIG. 1 and demonstrate diffuse staining of the lung. The stain localizes to the alveolar walls, indicating that greater than 70% of pulmonary vascular endothelial cells, as well as alveolar lining cells, including type I and type II cells and alveolar macrophages are transfected by a single iv injection of DNA lipid carrier complexes. In addition, significant numbers of bronchiolar airway lining cells stain positively for CAT protein, and are therefore transfected in vivo by iv injection of lipid carrier:DNA complexes. Thus, the great majority of all cells in the lung transfected by an iv injection of pZN27-DDAB:Cholesterol complexes.

Example 4

Expression of pCIS-CAT Following Intraperitoneal Administration

Effect of the Amount of pCIS-CAT-cationic Lipid Carrier Complexes Injected ip on the Level of CAT Gene Expression in vivo.

Female ICR mice were injected ip with 1 ml of 5% dextrose in water containing 0.01, 0.1, or 1 mg of pCIS-CAT expression plasmid complexed with 0.01, 0.1 or 1 $\mu$moles, respectively, of DDAB:DOPE lipid carriers. Mice were sacrificed 48 hours later, the organs removed, and tissues were homogenized in 0.25M Tris-HCl buffer pH 7.8, using a hand-held homogenizer. Cytoplasmic extracts were made, normalized by protein content and the level of CAT activity then measured. The experiments comprise three animals per group and the results show the mean dpm±SEK of acetylated chloramphenicol.

Methods: Lipid carriers containing DDAB were prepared in 1:1 molar ratio with DOPE, as follows: 10 gmoles of DOPE dissolved in chloroform and 10 $\mu$moles of the cationic lipid, dissolved in ethanol were evaporated to dryness on a rotary evaporator. one ml sterile of water was added, and the mixture was sonicated in a bath sonicator (Laboratory Supply, Hicksville, N.Y.) for 20 min. Lipid carriers had mean diameters of approximately 100±25 nm. For CAT assay, cell extracts were made, and their protein content determined by the Coomassie Blue assay (BioRad, Richmond). One hundred $\mu$g of protein from the lung, spleen, liver, and heart extracts, and 50 $\mu$g of lymph node extract were reacted with $^{14}$C labeled chloramphenicol and chromatographed as previously described (Gorman, supra). To calculate dpm, both the acetylated and unacetylated species were cut from TLC plates and radioactivity counted in a scintillation counter.

Results: To assess potential dose-response relationships in vivo, animals were injected animals in groups of three with 0.01 mg, 0.1 mg, or 1 mg of pCIS-CAT plasmid complexed with 0.01 $\mu$mole, 0.1 $\mu$mole, or 1 $\mu$mole respectively of DDAB:DOPE lipid carriers. Both the 0.1 mg and 1 mg DNA doses produced highly significant levels of CAT protein ($p<0.005$) in all the organs assayed. Maximal levels of CAT gene expression in each organ were produced by the 1 mg DNA dose: increasing the DNA-lipid carrier dose 10 fold resulted in an approximately 2 fold increase in lymph node CAT levels and a 3 fold increase in the spleen.

Example 5

Demonstration of CAT Gene Expression in the Spleen After Intravenous (iv) Injection of p5'PRL3-CAT:L-PE:CEBA Complexes Lipid carrier: L-PE:CEBA=1:1, stock 20 mM in lipid carrier buffer.
Plasmid: p5'PRL3-CAT. (Sakai, et al., (1988) *Genes and Development* 2:1144-1154)
DNA:Lipid carrier Ratio: lipid carrier:plasmid=1 nmole cationic lipid: 1 µg plasmid DNA.
DNA dose: 200 µg plasmid DNA in 200 µl 5% dextrose in water was injected by tail vein per mouse.
Mice: Balb/c, female, 25 grams.

Tissue extraction procedure: Forty eight hours after tail vein injection, mice were sacrificed, whole spleens were homogenized in 1 ml of 0.25M Tris-HCl pH 7.8, 5 mM EDTA, 80 µg/ml PMSF and the resulting extract was centrifuged and then the supernatant was subjected to 3 cycles of freeze-thaw and then heated to 65° C. for 20 min.

CAT assay Drocedure: 100 µl of extract+10 µl of 20 mM acetyl CoA+4 µl of $^{14}$C-chloramphenicol (25 µCi/ml, 55 mCi/mmole, Amersham) were incubated together at 37° C. for 6 hr. At 3 hours, an additional 10 µl of acetyl CoA was added.

Results:

This experiment showed that a significant level of CAT activity was present in the spleen extract of the treated animal, but not in the extract of control spleen, taken from an animal injected with lipid carrier alone.

Example 6

Injection of DOTMA:DOPE+pSIS-CAT Plasmid Clearly Did Not Produce

Detectable CAT Gene Expression in vivo
Lipid carrier: DOTMA:DOPE=1:1, in 5% dextrose in water
Plasmid: pSIS-CAT (Huang, and Gorman, (1990) *Nucleic Acids Research* 18:937–947).
Ratio: Cationic lipid:plasmid=4 nmoles: 1 µg, dose: 100 µg DNA in 200 µl 5% dextrose in water.
Mouse: ICR, female, 25 grams.
Injection: tail vein.
Tissue collection and processing: Mice were sacrificed at day 2 and day 6, and lung, spleen, liver, and heart were collected. The whole organs were homogenized in 0.5 ml, except livers which were homogenized in 2.0 ml, of 0.25M Tris-HCl pH 7.8, 5 mM EDTA, 2 µg/ml aprotinin, 1 µg/ml E-64, and 0.5 µg/ml leupeptin (all protease inhibitors purchased from Boehringer Mannheim). Extracts were subjected to three cycles of freeze-thaw, then heated to 65° C. for 10 min.
CAT assay: 100 µl of extracts for each assay with 0.3 µCi of $^{14}$C-chloramphenicol and 10 µl of 20 mM acetyl CoA at 37° C. for either 5 hrs or 24.5 hrs, and the materials were then extracted using ethyl acetate and analyzed on TLC plates.
Results:

There were no acetylated chloramphenicol species presented as determined by comparing the extracts from treated animals with that from control animals. Thus, under similar experimental conditions that produce high level expression of pZN27, the use of the pSIS-CAT expression vector does not result in any detectable expression of the linked-CAT gene in any of the tissues assayed in vivo. The lack of expression of pSIS-CAT in vivo may be due either to a different promoter-enhancer element (SV40) or to a different intron sequence when compared to the pZN27 vector, which yields high level in vivo expression.

Example 7

Interaction Of DNA: Lipid Carrier Complexes With Cell Surface Receptors

Cells and cell culture: CV-1 (African green monkey kidney), U937 (human myelocytic leukemia), murine erythroleukemia (MEL) cells, and K562 cells (human erythroleukemia cells were obtained from the American Type Culture Collection (Rockville, Md.). CV-1 and MEL cells were maintained in Dulbecco minimum essential medium DME-H-21 with 5% fetal bovine serum (FBS) at 37° C. and 7% $CO_2$. Rat alveolar type II cells and rat alveolar macrophages were isolated and purified as previously described. (Debs et al., (1987) *Amer. Rev. Respiratory Disease* 135:731–737; Dobbs, (1986) *Amer. Rev. Respiratory Disease* 13:141–145) Type II cells were maintained in DME-H-16 with 5% FBS at 37° C. and 7% $CO_2$. Twenty nmole of DOTMA:DOPE lipid carriers complexed to 20 µg of pRSV-CAT plasmid DNA were added to 2 million cells growing in 60 mm Falcon plastic dishes (either SUV or MLV), and fixed for EM at time points from 15 minutes to 2 hours thereafter.
Fixation and Processing for Electron Microscopy DOTMA lipid carriers and cells in tissue culture or freshly isolated from blood or pulmonary alveoli were fixed in 1.5% glutaraldehyde in 0.1 molar sodium cacodylate buffer containing 1% sucrose, pH 7.4, at room temperature for 1 hr. Following tannic acid and uranyl acetate enhancement, tissue was dehydrated in a graded series of alcohols and embedded in epoxy 812 resin (Ernest F. Fullam, Inc., Latham, N.Y.) sectioned on an MT 2 microtome using diamond knives and examined with a Jeol 100CX transmission electron microscope operating at 80 kV. Electron photomicrographs of the internalization of lipid complexes in CV-1 monkey kidney cells are shown in FIG. 7. The arrows in panel (a) show particles binding to clathrin-coated pits; in panel (b), the arrows show where the particles have been ingested and are present in endosomes.

The most frequent interaction between DOTMA lipid carriers, either uni- or multilamellar lipid carriers, complexed to plasmid DNA and the various cell types (CV-1 monkey kidney cells, U937 human myelomonocytic leukemia cells, K562, MEL erythroblastic leukemia cells, rat alveolar macrophages, and alveolar type II cells), is that of lipid carrier adhesion and internalization in a typical coated vesicle pathway (FIG. 7a–f). This interaction is common to well defined examples of receptor-mediated endocytosis. All cells which appear to have contacted cationic lipid carrier:DNA complexes ingest the complexes after binding to the plasma membrane. All these cell types (derived from rodent, monkey and human cells, demonstrated the same classical receptor-mediated endocytic pathway of internalization. DNA-cationic liposome complexes were generally taken up by human cells as well as or better than nonhuman and particularly rodent cells of similar lineage.

Example 8

Demonstration that Mouse T Lymphocytes are Transfected in vivo

Female ICR mice were injected ip with 1 ml of 5% dextrose in water containing 1 mg of a pZN27 plasmid complexed to 1 µmole of DDAB:DOPE (1:1 molar, SUV) lipid carriers. Mice were sacrificed 48 hrs. later, the spleen and lymph nodes were removed, and rendered into single cell suspensions by homogenizing in serum containing medium. The cells were then incubated with FITC-conjugated anti-Thy 1.2 antibody (provided by Dr. J. Beck, San Francisco Veterans Administration Medical Center) and sorted by FACS. The Thy 1.2+ T lymphocyte fraction was cytospun onto microscope slides and fixed and probed for the presence of intracellular CAT protein after permeabilizing the cells using 0.25% Triton X-100. The cells were incubated with an anti-CAT monoclonal antibody (gift from Dr. P. Antin, Univ. of Arizona) for 1 hr. at 20° C. and then stained with a Texas Red-conjugated goat-anti-mouse IgG for 1 hr. at 20° C. FIG. 2A shows a field of T lymphocytes by phase contrast microscopy and 2B shows the same field viewed by fluorescence microscopy. These results demonstrate that more than 70% of Thy 1.2+ T lymphocytes are transfected in vivo (as shown by the red fluorescence), by a single ip injection of pZN27:DDAB:DOPE complexes. Thy 1.2+ lymphocytes from untreated mice do not show immunofluorescent staining as shown in 2D; a phase contrast micrograph of the same field is shown in 2C.

Example 9

Demonstration that Mouse Hematopoietic Bone Marrow-Derived
Cells are Transfected in vivo.

Female ICR mice were injected ip with 1 ml of 5% dextrose in water containing 1 mg of a pZN27 plasmid complexed to 1 μmole of DDAB:DOPE SUV lipid carriers. Mice were sacrificed 48 hrs. later, bone marrow-derived hematopoietic cells were then obtained by perfusing the femur cavity with RPMI-1640 medium and then homogenizing clumps to obtain a single cell suspension. Bone marrow cells were then centrifuged onto glass slides and fluorescently stained as described in Example 8. This experiment demonstrated that approximately 20% of mouse bone marrow hematopoietic cells (including cells that on the basis of morphology are primitive myeloblastic and erythroblastic precursor cells) were transfected in vivo by a single ip dose of pZN27:DDAB:DOPE complexes.

Example 10

Demonstration that Human CD4+ T Lymphocytes, Freshly Isolated from Normal Donors, are Transfected in vitro Buffy coat preparations were freshly isolated from normal human donors by gradient centrifugation. The cells were then panned using an anti-CD3 (Becton-Dickinson, Mountain View, Calif.) monoclonal antibody to isolate the CD3+ T lymphocyte fraction. These cells were then transfected using the following protocol: 10 million cells were plated on 100 mm dishes and then 25 μg of pZN27 complexed to 50 nmoles of DDAB:DOPE (1:1) SUV lipid carriers were added for 48 hours. Control cells were not transfected. The cells were then incubated with a FITC-conjugated monoclonal anti-CD4 antibody (Becton-Dickinson) and sorted by FACS. The resulting CD4+ T lymphocytes were cytospun onto microscope slides and fixed and probed for the presence of intracellular CAT protein after permeabilizing the cells using 0.25% Triton x-100. The cells were incubated with an anti-CAT monoclonal antibody for 1 hr at 20° C. and then stained with a Texas Red conjugated goat anti-mouse IgG for 1 hr at 20° C.
Results:
Results are shown in FIG. 4 and demonstrate that at least 70% of freshly isolated human CD4+ T lymphocytes are transfected after exposure to pZN27:DDAB:DOPE complexes in culture as shown by the red fluorescence of cells in 4B. Control untransfected cells showed no fluorescence.

These results suggest that this approach may dramatically improve the therapy of diseases including AIDS and cancer.

As the above results show, high level transgene expression has been achieved in heart, kidney, lymph nodes, bone marrow cells, liver, lung and spleen after systemic (iv or ip) transgene administration. Transfection of the heart, kidney, lymph nodes or bone marrow cells individually after systemic (iv or ip) transgene administration into adults has not previously been accomplished. Transfection of T lymphocytes, lung airway or alveolar cell types, cardiac endothelial lining cells and cardiac muscle cells, and bone marrow hematopoietic precursor cells in vivo by systemic administration of DNA has not been shown previously. Specifically, greater than 50% of T lymphocytes, lung airway epithelial, alveolar and vascular endothelial cell types, cardiac endothelial lining cells and bone marrow hematopoietic precursor cells (including about 70% of blast cells) are transfected in vivo, following one iv or ip injection of CAT expression plasmid-cationic lipid carrier complexes. Transfection of a high percentage of all the cells present in any single tissue has not been reported previously.

Example 11

Efficient Transfection of a Variety of Human Lung Cancer Cell Lines using Cationic Liposome-mediated Delivery of DNA Method:
Cell Culture: NCI-H69, NCI-H82, and NCI-H520 cells were used. H69 and H520 cells were grown in RPMI-1640 with 10% fetal bovine serum (FBS) and H82 cells were grown in Dulbecco's minimum essential medium (DME)-H21 with 10% FBS.
Liposome preparation: Liposomes were prepared as follows: a total of 4 μmoles of lipid dissolved in chloroform, (or in ethanol (DOTMA)) were evaporated to dryness on a rotary evaporator. One ml of 50 mM Tris, 0.5 mM EDTA, 50 mM NaCl, 100 μM $ZnCl_2$ buffer per 20 mmoles of lipid was added, and the mixture was sonicated in a bath sonicator (Laboratory Supply Co., Hicksville, N.Y.) for 20 min. The resulting liposomes have an approximate mean diameter of 100±25 nm. The following liposome preparations were used: pure DOTMA, DOTMA:Cholesterol in a 2 to 1 molar ratio, pure L-PE or L-PE:CEBA in a 6 to 4 molar ratio.
Cellular transfection: For transfection of cells, $2 \times 10^6$ cells in 4 ml of serum-free medium were plated in 100 mm plastic petri dishes (Falcon, Oxnard, Calif.). The plasmid DNA-liposome complex was prepared by first adding 1) DNA and then 2), liposomes and mixing gently. The complex was then suspended in 1 ml of serum-free medium and added to the cells. Four hours later, the cells were washed twice, resuspended in 10 ml of serum-containing medium, and subsequently harvested, 44 hours later. Just prior to harvesting, the cells were washed 2 times, and the plates were then scraped with a rubber policeman. The cells were centrifuged at 1,000×g for 5 min, and 0.135 ml of 0.25 M Tris buffer pH 7.5, 5 mm EDTA was added to each pellet. The cells were freeze-thawed 3×, heated at 65° C. for 10 min, and spun at 12,500×g for 10 min. The supernatant was assayed for protein and 20 μg of supernatant protein per sample was used to measure CAT activity, as described in Example 4.
Results: The results demonstrate the ability of cationic liposomes to mediate high level transfection of two different human small cell lung cancer lines (H69 and H82) and a squamous cell lung cancer line (H520). All three lines were very efficiently transfected by RSV-CAT when complexed to 3 different cationic liposome formulations (FIG. 21). These human cell lines were transfected either as, or more effi-

Example 12

Transfection of Lung Cancers in Mice by Intravenous Injection of Cationic Lipid Carrier:DNA Complexes Mouse: C57/black 6, female, 25 grams.
Cancer: B16, mouse melanoma line which is highly metastatic to lung. The cell line was grown in RPMI 1640 medium supplemented with 5% fetal calf serum.
Lipid carrier: DOTAP:Cholesterol=1.1, 10 mM in 5% dextrose in water.
Plasmid: pZN20.
Ratio: Cationic lipid:DNA=6 nmoles:1 µg, 100 µg in 200 µl of 5% dextrose in water were injected by tail vein into each mouse.
Inoculation of Cancer Cell Line into Mice and Administration of CAT Expression Plasmid-cationic Lipid Carrier Complexes:

B16 cells were trypsinized off the plates and 50,000 cells were inoculated into each mouse by intravenous injection into the tail vein. Two weeks after injection, cationic lipid carrier-DNA complexes were injected via tail vein. Lungs were collected 48 hours postinjection, infused with 33% O.C.T., frozen in a dry ice-ethanol bath, cryosectioned, and processed for immunohistochemical analysis to detect intracellular CAT protein.
Immunohistochemical Analysis: Procedure:

Organs were removed, appropriately trimmed, embedded in OCT and snap frozen. Frozen tissues were sectioned at 6 µm, collected onto glass slides, fixed for 10 minutes in 4° C. acetone and then placed in 0.2% Triton X-100 to permeabilize membranes. Sections were then incubated for 12–48 hours with the monoclonal anti-CAT antibody or isotype negative control antibody at the appropriate dilution. After washing, a biotinylated antibody directed against the primary antibody (Zymed, S. San Francisco) was added for a minimum of 60 minutes, followed by application of the streptavidin-peroxidase complex (Zymed) for 60 minutes and then application of the substrate-chromogen appropriate for the enzyme label used. Slides can then be counter-stained in dilute hematoxylin or left unstained and coverslipped in water-soluble mounting media for examination.
Results:

Immunohistochemical analysis are shown in FIG. 8 and demonstrate that B-16 melanoma lung tumors (8A, indicated by arrows) as well as intravascular tumor emboli (8B, indicated by arrows) are efficiently transfected after iv injection of DNA-lipid carrier complexes. Both lung tumors and intravascular tumor emboli show intense staining, indicating efficient, a generalized transfection in vivo. Tumor bearing mice, which did not receive an injection of DNA-lipid carrier complexes, show no CAT activity in the lung or in any lung tumor cells (8C). The ability to transfect tumors present within mammalian hosts by systemic administration of a cloned gene has not previously been demonstrated.

Example 13

Demonstration of High Level CAT Gene Expression in Multiple Tissues After Intravenous (iv) Injection of pZN27 Alone, or pZN27:DDAB:Cholesterol SUV Complexes Lipid carrier: DDAB:Cholesterol=1:1, stock 10 mm in 5% dextrose. After addition of 5% dextrose to the dried lipid film, the SUV were prepared by sonication in a bath sonicator for 20 minutes.
Plasmid: pZN27.
DNA:Lipid carrier Ratio: Cationic lipid:plasmid DNA=5 nanomoles:1 µg DNA.
DNA dose:

pZN27 alone: Individual mice received 500 µg, 1 mg, 2 mg, or 500 µg, followed 4 hours later by a second 500 µg dose, respectively of pZN27 in 200 ml 5% dextrose in water by tail vein injection.

pZN27 complexed to lipid carriers: 100 µg plasmid DNA complexed to 500 nanomoles to DDAB:Cholesterol SUV lipid carriers in 200 µl 5% dextrose in water was injected by tail vein per mouse.
Mice: ICR, female, 25 grams.
Tissue extraction procedure: Each organ was homogenized in 0.3 ml of 0.25 M Tris-HCl pH 7.8, 5 mM EDTA, and the resulting extract was centrifuged and the supernatant was then subjected to 3 cycles of freeze-thaw and then heated to 65° C. for 20 min.
CAT assay procedure: The protein concentration of each tissue extract was quantitated using a Coomassie Blue-based protein assay (BioRad, Richmond), and same amount of total protein from each tissue extract was added in the CAT assay, together with 10 µl of 20 mM acetyl CoA+12 µl of $^{14}$C-chloramphenicol (25 µCi/ml, 55 mCi/mmole, Amersham)), at 37° C. for 13 hrs.
Results:

Significant levels of CAT gene expression were seen in each of the 6 different tissues assayed (lung, heart, liver, kidney, spleen, and lymph nodes) after injection of either pZN27 alone, or pZN27 complexed to DDAB:Cholesterol lipid carriers. Expression of a transgene in multiple tissues in vivo after systemic injection of a naked expression plasmid previously has not been demonstrated.

Example 14

Induction of High Levels of Human Interleukin-2 in the Spleen and Lymph nodes of Mice by Intravenous Injection of Cationic Lipid Carriers Complexed to a CMV-Interleukin-2 Gene Mouse: C57/black 6, female, 25 grams.
Cancer: B16, mouse melanoma line which is highly metastatic to lung. The cell line was grown in RPMI-1640, 5% fetal calf serum.
Lipid carrier: DDAB:Cholesterol=1.1, 10 mM in 5% dextrose in water.
Plasmid: pZN46 (the HCMV promoter enhancer fused to the human interleukin-2 coding sequence).
Ratio: Cationic lipid:DNA=5 nmoles:1 µg DNA in 200 µl of 5% dextrose in water administered per injection.
Inoculation of the Tumor Cell Line into Mice and Administration of a Human Interleukin-2 Expression Plasmid-cationic Lipid Carrier Complexes B16 cells were trypsinized off the plates, and 50,000 cells were inoculated into each mouse by intravenous injection into the tail vein. Starting 2 days after the tumor cell injection, cationic lipid carrier-DNA complexes were injected via tail vein 2 times per week for a total of 2 weeks. The animals were sacrificed 2 weeks post tumor cell injection, the spleen and lymph nodes were removed, rendered into single cell suspensions using a tissue grinder, and then cultured for 24 hours in RPMI-1640, 10% fetal calf serum in 100 mm plastic dishes in a 37° C. incubator. After 24 hours the supernatant was collected and the concentration of human interleukin-2 in the supernatant was determined using a human IL-2 ELISA.
Results:

One hundred picograms of human IL-2/ml per ml was present in the spleen cell supernatant and 91 pg/ml IL-2 was present in the lymph node cell supernatant from the mouse which was injected with the pZN46-DDAB:Cholesterol lipid carrier complexes. No human IL-2 was detected in either spleen cell or lymph node cell supernatants derived from mice which received an identical injection of B-16 melanoma cells, but which did not receive the pZN46-DDAB:Cholesterol lipid carrier complexes. Thus, substituting the human IL-2 gene coding region for the CAT gene coding region in a HCMV expression plasmid resulted in high level expression of the IL-2 gene in vivo and the production of large amounts of a secreted human IL-2 protein in a mouse.

Example 15

Induction of High Level Expression of the Human CFTR Gene in Mice Treated by iv Administration of pZN32:Cationic Lipid Carrier Complexes Mice: ICR female, 25 grams
Lipid carrier: DDAB:Cholesterol=1:1 SUV, 10 mM in 5% dextrose in water
Plasmid: pZN32 (the HCMV promoter enhancer fused to the human CFTR coding sequence)
Ratio: Cationic lipid:DNA=5 nmoles:1 $\mu$g plasmid DNA.
Dose: A total of 100 $\mu$g of plasmid DNA in 200 $\mu$l of 5% dextrose in water administered per iv tail vein injection.
Procedure:

Forty-eight hours after injection the mice were sacrificed, the lungs were removed and trimmed, embedded in OCT, and snap frozen. Frozen tissues were sectioned at 6 $\mu$m, collected onto glass slides, and the fixed for 10 minutes in 4% acetone. Immmunolocalization of CFTR was then performed using the affinity purified rabbit polyclonal anti-CFTR antibody, $\alpha$-1468 (Cohn, et al., (1991) *Biochem. Biophys. Res. Comm.* 181:36–43). The procedure used was identical to the one described in Marino et al., (1991) *J. Clin. Invest.* 88:712 with the following variation. After washing, a biotinylated antibody directed against the rabbit polyclonal antibody (Zymed) was added for 60 minutes, followed by application of the streptavidin phosphatase complex (Zymed) for 60 minutes and then application of the substrate-chromogen. Slides were then coverslipped in water-soluble mounting media for examination.

Results:

Photomicrographs of frozen sections (viewed at different magnifications) of mouse lung 48 hours following iv injection to pZN32-DDAB:Cholesterol (1:1) liposome complexes and lung from untreated control are shown in FIGS. 12A–E. As demonstrated by the intense staining with the polyclonal anti-CFTR antibody, $\alpha$-1468, the overwhelming majority of the airways were transfected with the human CFTR gene. In 12A, 12C and 12E. by visual inspection, essentially all the cells in transfected airways stain positively, demonstrating that the overwhelming majority of airway cells are transfected with the human CFTR gene in vivo with a single iv dose of pZN32 complexed to DDAB-cholesterol (1:1) liposome-treated and control animals could not be distinguished histologically. Significant expression of the human CFTR gene is present in at least 50% of all the airways and at least 50% of all of the airway lining cells (by visual inspection) in mouse lungs for at least 60 days following a single iv dose of pZN32 complexed to DDAB-Cholesterol (1:1) liposomes. Frozen sections of mouse lungs from control animals (12B and 12D) do not show any detectable staining for CFTR, confirming that all the CFTR expression present in 12A, 12C and 12E is due to transfection of lung cells with the human CFTR gene.

As shown by the above results, a single iv dose of an expression construct, containing a gene of interest, complexed to cationic liposomes transfects the majority of the cells lining the conducting airways of the lung, the gene product is present in the lung for at least 60 days, the expression appears to be airway cell-specific, and there is no histological evidence of damage following exposure. This is important because liposomes are well tolerated and non-immunogenic. Furthermore, the appearance, behavior, and life span of mice treated with intravenously injected pZN32:DDAB-Cholesterol (1:1) complexed appear normal, and are indistinguishable from untreated, normal control animals. This lack of toxicity, as demonstrated by analysis of appearance, behavior, life span and detailed histologic analysis of a wide variety of tissues from these animals demonstrates the lack of toxicity produced by in vivo delivery of pZN32-DDAB:Cholesterol complexes. Additionally, the effects of repeated iv administration of the DNA/liposome complexes is effective and is non-toxic. The cationic liposome-mediated DNA delivery by iv injection provides high level, lung-specific transgene expression in vivo.

Example 16

Demonstration of CAT Gene Expression in Lung and Liver After Intravenous Injection of Different CAT Gene-Containing Plasmids Lipid carrier: DDAB:Cholesterol=1:1, stock 5 mM in 5% dextrose in water.
Plasmids: Plasmids are indicated below.
DNA-Lipid carrier Ratio: Cationic lipid: plasmid DNA=1 nanomole: 1 $\mu$g
Dose: 100 $\mu$l DNA in 200 $\mu$l volume injected intravenously by tail vein injection.
Mice: ICR, female, 25 g
Procedure: The animals were sacrificed 24 hours after injection. The tissue extraction procedure and CAT assay were as described in Example 4 except that the CAT assay was incubated for 3 hr at 37° C. and 2.0 mM paraoxon (Lai, et al., (1988) *Carcinogenesis* 9:1295–1302) was added to the liver samples. The results are shown in FIG. 15. Lanes 1–12 are lung samples, lanes 13–24 are liver samples. Lanes 1, 2, 13, 14 are pZN51; lanes 3, 4, 15, 16 are pZN60; lanes 5, 6, 17, 18 are pZN61; lanes 7, 8, 19, 20 are pZN62; lanes 9, 10, 21, 22 are pZN63; and lanes 11, 12, 23, 24 are pZN27.
Results:

pZN51, which does not contain an intron, is expressed as well as, or better than, plasmids containing an intron either 3' or 5' to the coding sequence.

Example 17

Generalized Versus Tissue and Cell Type-specific CAT Gene Expression Produced by iv Injection of CMV-CAT-liposome or CFTR-CAT-liposome Complexes Respectively Mouse: ICR female, 25 grams.
Liposome: DDAB:Cholesterol=1:1 SUV, 10 mm in 5% dextrose in water.
Plasmid: 1) pZN27 or 2) pBE3.8CAT (see Chou et al., (1991) *J. Biol Chem* 266:24471–24476, for construction).
Experimental conditions: Mice in groups of 3 received either (a), no treatment, or (b), a single iv tail vein injection of DDAB:Cholesterol liposomes complexed to 100 $\mu$g of) a 3.8 kb sequence of the 5' upstream region of the human CFTR gene fused to the CAT gene (pBE3.8CAT) or (c) pZN27. Mice were sacrificed 24 hours later and CAT activity assayed in lung, liver, spleen, lymph nodes, kidney and heart, as described in Example 4. Immunohistochemical analysis of lung section from each of the groups was performed as described in Example 3.

Figure 16A:
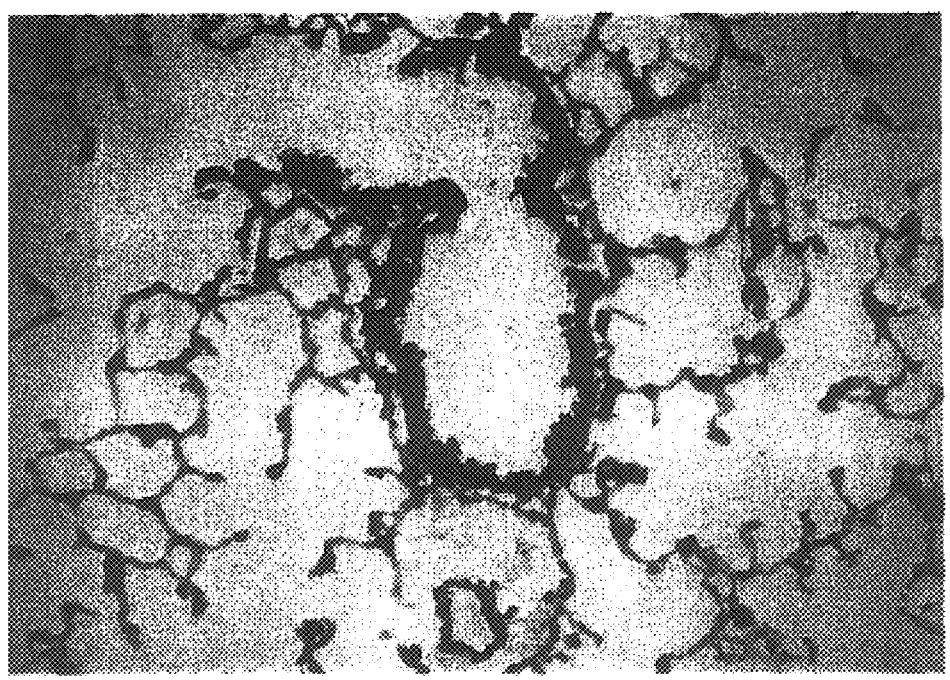
Figure 16B:
Figure 16D:
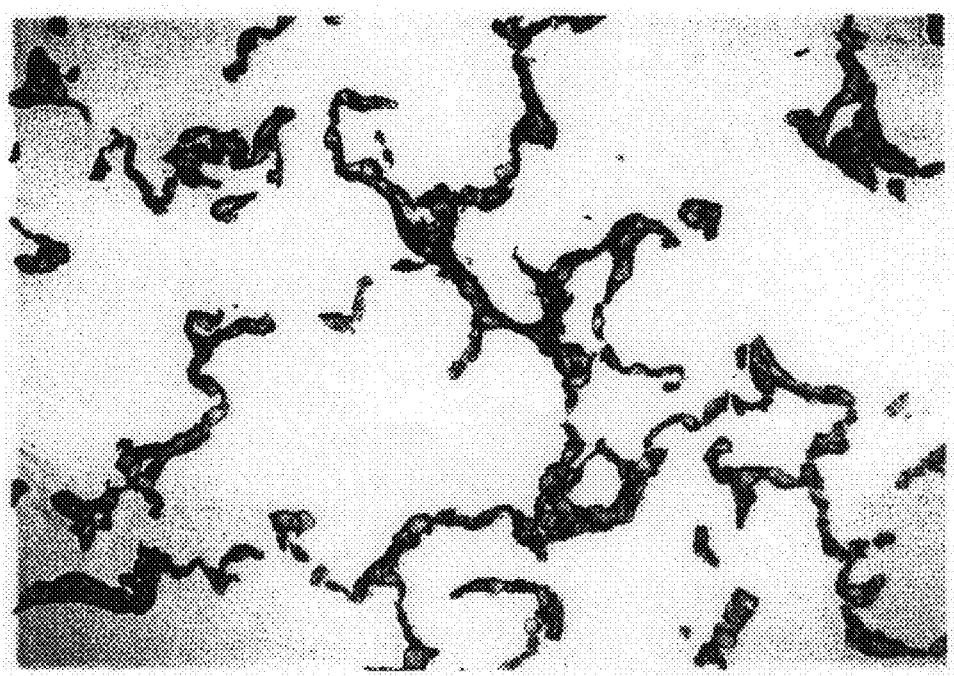
Figure 16E:
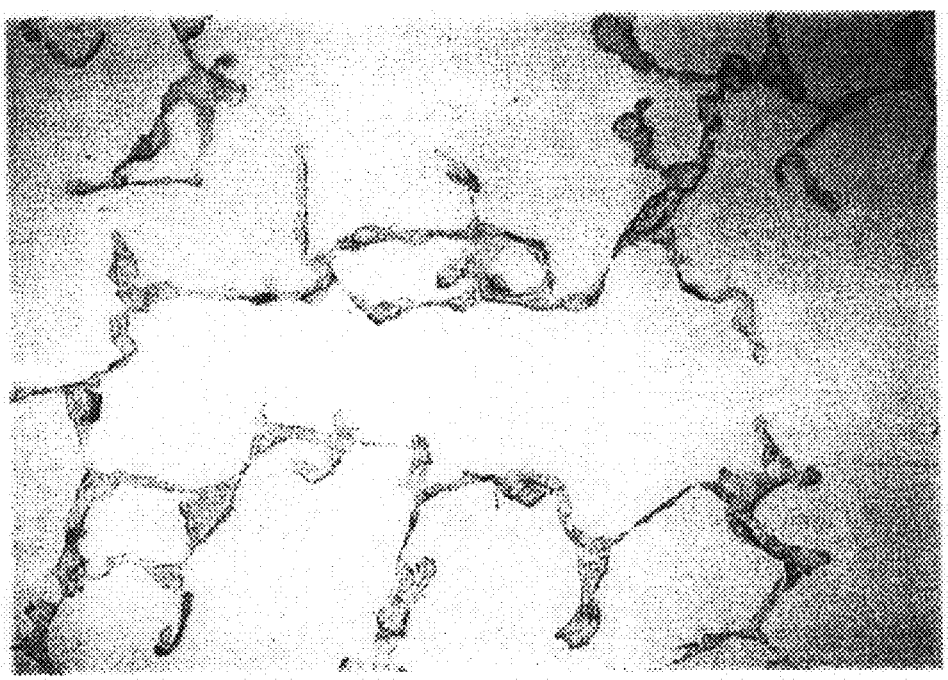

Results:

Immunohistochemical staining of frozen lung sections from these mice showed that iv injection of CMV-CAT-liposome complexes produced high levels of red staining, indicating CAT gene expression in endothelial, alveolar and airway cells within the lung (16A). In contrast, CFTR-CAT-liposome complexes produced CAT gene expression primarily localized in airway epithelial cells (16B). This approximates the pattern of endogenous CFTR gene expression in rat lung, as determined by in situ hybridization studies (Trezise and Buchwald, (1991) Nature 353:434–437. A lung section from an uninjected mouse does not show red staining, indicating that CAT gene expression is present only in transfected cells (FIG. 16C). FIG. 16D is a high magnification photomicrograph of alveoli from a CMV-CAT treated mouse and shows a high level of CAT gene expression in both alveolar cells and lung endothelial cells. A high magnification photomicrograph of alveoli from CFTR-,CAT treated mice (FIG. 16E) shows no significant CAT gene expression in either alveolar or endothelial cells, demonstrating that the CFTR promoter targets transgene expression to airway epithelial cells. This is the first demonstration that transgenes can be expressed within mouse lung in either a generalized or cell type-specific fashion depending on the regulatory element used, after iv injection.

CAT assay demonstrated that CMV-CAT produced significant CAT gene expression in the lung, liver, heart, spleen, lymph nodes and kidney, whereas CFTR-CAT produced lung-specific gene expression. Photographs of autoradiographic analysis of each tissue are shown in FIG. 16 (F–K). Thus, the CMV promoter induces expression of a linked gene in a wide range of tissues, whereas the 5' flanking region of the human CFTR gene directs tissue-specific transgene expression after iv, liposome-based administration.

Example 18

Comparison of Transfection Focusing on iv Injection of Plasmid Alone with iv Injection of Plasmid Complexed to a Lipid Carrier Demonstration of Widespread, High Level CAT Gene Expression in in vivo After Intravenous (iv) Injection of pZN27 Alone.

Plasmid: pZN27.

DNA:Liposome Ratio: Plasmid DNA alone, without liposomes, was injected.

DNA dose: 1 mg plasmid DNA in 200 µl 5% dextrose in water was injected times 2 over a 4 hour period by tail vein per mouse. Mice were sacrificed 24 hours later and 17 different tissues were assayed for CAT gene activity.

Mice: ICR, female, 25 grams.

Tissue extraction procedure: Each organ was homogenized in 0.3 ml of 0.25 M Tris-HCl pH 7.8, 5 mM EDTA, and the resulting extract was centrifuged and then subjected to 3 cycles of freeze-thaw and then treated to 65° C. for 20 min.

CAT assay procedure: The protein concentration of each tissue extract was quantitated using a ninhydrin-based protein assay (BioRad, Richmond), and the same amount of total protein from each tissue extract was added in the CAT assay, together with 10 µl of 20 mM acetyl CoA+12 µl of $^{14}$C-chloramphenicol (25 µCi/ml, 55 mCi/mmole, Amersham), at 37° C. for 13 hrs.

Results: An autoradiograph of this experiment is shown in 19A. Compared to control levels (lane 1), iv injection of pZN27 alone produced highly significant levels of CAT gene expression in the following tissues: lung, thymus, esophagus, heart, liver, spleen, stomach, small intestine, caecum, ovary, vagina, skeletal muscle, pancreas and lymph nodes. Thus, iv injection of the pZN27 expression plasmid alone can efficiently transfect a very large and diverse number of tissues in the body.

Demonstration of Widespread, High Level CAT Gene Expression in vivo After Intravenous (iv) Injection of pZN27 Completed to DDAB:Cholesterol (1:1) Liposomes.

Plasmid: pZN27.

Liposome: DDAB:Cholesterol=1:1, stock 10 mM in 5% dextrose.

DNA:Liposome Ratio: liposome:plasmid 5 nmoles:1 µg

DNA dose: 100 µg plasmid DNA in 200 µl 5% dextrose in water was injected by tail vein per mouse. Mice were sacrificed 24 hours later and 17 different tissues were assayed for CAT gene activity.

Mice: ICR, female, 25 grams.

Tissue extraction procedure: Each organ was homogenized in 0.3 ml of 0.25 M Tris-HCl pH 7.8, 5 mM EDTA, and the resulting extract was centrifuged and then subjected to 3 cycles of freeze-thaw and then treated to 65° C. for 20 min.

CAT assay procedure: The protein concentration of each tissue extract was quantitated using a ninhydrin-based protein assay (BioRad, Richmond), and same amount of total protein from each tissue extract was added in the CAT assay, together with 10 µl of 20 mM acetyl CoA+12 µl of $^{14}$C-chloramphenicol (25 µCi/ml, 55 mCi/mmole, Amersham), at 37° C. for 13 hrs.

Results: An autoradiograph of this experiment is presented in FIG. 19B. Compared to control levels (lane 1), iv injection of pZN27:DDAB:Cholesterol complexes produced high levels of CAT gene expression in the following tissues: lung, thymus, esophagus, heart, liver, spleen, stomach, small intestine, large intestine, caecum, uterus, ovary, vagina, skeletal muscle, pancreas and lymph nodes. Thus, iv injection of pZN27:DDAB:Cholesterol complexes can efficiently transfect a very large and diverse number of tissues in the body.

Example 19

IV Injection of GM-CSF Expression Plasmid-Cationic Liposome Complexes Produces Significant Antitumor Effects Mouse: C57/black 6, female, 25 grams.

Cancer: B16, mouse melanoma line which is highly metastatic to lung. The cell line was grown in RPMI-1640, 5% fetal calf serum.

Liposome: DDAB:Cholesterol=1:1, 10 mM in 5% dextrose in water. Twenty five thousand B-16 cells were injected iv by tail vein.

Plasmid: pZN84 (the HCMV promoter enhancer fused to the murine GM-CSF coding sequence as shown in FIG. 17).

Ratio: Cationic lipid:DNA=5 nmoles:1 µg. A total of 100 µg of plasmid DNA in 200 µl of 5% dextrose in water administered per injection.

Experimental outline: Mice in groups of eight received a single iv tail vein injection of 2.5×10$^4$ B-16 melanoma cells. Group 1 received no treatment, group 2 received bi-weekly injections of 100 µg of pZN84 complexed to DDAB:Cholesterol liposomes, beginning 4 days prior to tumor cell injection and continuing for 2 weeks following tumor injection. All mice were sacrificed 3 weeks following tumor cell injection and surface lung tumor nodules which were black and macroscopic were counted using a dissecting microscope.

Results:

Control animals had 64.5±19.7 (S.E.M.) nodules per lung. In contrast, the GM-CSF-liposome-treated animals had 11.9±3.6 tumor nodules per lung (p<0.01 versus the control group, as assessed by Student's t test). Thus, iv injection of a cytokine gene produced a highly significant antitumor effect. This is the first demonstration that iv injection of a gene can produce anti-tumor activity in vivo.

Example 20

Prolonged, High Level Murine GM-CSF Gene Expression in vivo After Intravenous (iv) Injection of pZN84 Complexed to DDAB:Cholesterol (1:1) Liposomes into Goats Animals: Goats: female, 110 pounds
Plasmid: pZN84
Liposome: DDAB:Cholesterol=1:1, stock 10 mM in 5% dextrose
DNA:Liposome Ratio:Liposome: plasmid=5:1
DNA dose: 1.0 mg plasmid DNA in 5 ml 5% dextrose in water was injected by jugular vein per goat.
Blood Sampling: Blood was drawn just prior to injection of pZNB84 liposome complexes, and at 12, 24, 48, 72, 168 and 840 hours post-injection.
Murine GM-CSF ELISA assay procedure: Murine GM-CSF was measured in these serum samples using a commercial murine GM-CSF ELISA kit provided by Endogen. There is no cross reactivity between goat and murine GM-CSF by ELISA.
Results: As shown in FIGS. 22 and 23 (Goats A, B and C), as compared to control levels, iv injection of pZN84:DDAB:Cholesterol complexes produced high sustained circulating levels of mouse GM-CSF protein for at least 168 hours following injection. However, by 840 hrs (35 days) GM-CSF levels were substantially reduced (FIG. 27, Goat A). No mouse GM-CSF protein was detected in the circulation of a goat which received 1 mg of the CAT gene (pZN51) complexed to DDAB:Cholesterol liposomes by the identical iv injection protocol. The goat receiving the CAT gene did express CAT antigen on the majority of its circulating white blood cells at 24 hours after injection, as determined by immunostaining for CAT antigen. No CAT antigen was detected in the white blood cells of the goats which were injected with GM-CSF gene-liposome complexes. Thus, iv injection of pZN84:DDAB:Cholesterol complexes can produce high level expression of the murine GM-CSF gene for prolonged periods in goats. IV injection of pZN51:DDAB:Cholesterol complexes can produce high levels of the CAT gene product in the majority of all circulating white blood cells in goats.

Example 21

Influence of Liposome-GM-CSF Plasmid Complex on the Course of Experimental Viral Pneumonia in Mice Endogenous cytokines are believed to be included in the host response to a viral infection. It is therefore of interest to determine whether increased expression of a single cytokine, GM-CSF would influence the time course of viral pneumonia. The effect of delivering the murine GM-CSF plasmid-liposome complex via two different routes on the host response to a Sendai virus challenge is tested. The plasmid-liposome complex is delivered iv to one group of mice, and intranasally (in) to a second group. Dose, time of delivery, virus challenge dose and endpoints are the same for both groups. Dose of plasmid-liposome complex is 100 µg/mouse/dose. Dosing for both protocols occurs on the following scale:

| Group challenge | Initial PL* dose Endpoints | 2nd PL dose | Virus |
|---|---|---|---|
| IV Route days 3, 7, 10 | day-3 | day 0 | day 0 |
| IN Route days 3, 7, 10 | day-3 | day 0 | day 0 |

*PL - plasmid-liposome

Each experimental group consists of the following:
murine GM-CSF plasmid-liposome+virus: 3 mice
CAT plasmid-liposome+virus: 3 mice
Untreated+virus: 3 mice This results in 9 mice per timepoint (27 total for each experiment, 54 total mice). All animal procedures are performed via NIH and AAALAC guidelines including use of appropriate analgesia.

Virus challenge is administered intranasally with Sendai virus strain 771076, a strain known to be pathogenic in mice. Endpoints include the following (these have been shown to useful endpoints for Sendai pneumonia):

1. lung weight vs. body weight and brain weight
2. lung histopathology
3. quantitative virus recovery
4. Sendai specific antibody response
5. lung GM-CSF
6. lung TNF Example 22

High Level Expression of the CAT Gene in Mouse Brain Produced by Injection of DNA Alone or DNA-cationic Liposome Complexes Directly into the Central Nervous System Mice: ICR, female, 25 grams
Plasmid: pCIS-CAT
Liposome: DOTMA:DOPE (1:1)
For each mouse injected, 2.5 µg DNA was diluted in 5% dextrose, then mixed with liposomes diluted to the same volume in 5% dextrose. Five microliters were injected stereotactically into the right ventricle of each mouse.

| Ratio: | Plasmid:lipid = 1:0 (1 mg DNA:0 µmoles DOTMA) |
|---|---|
| | Plasmid:lipid = 1:1 (1 mg DNA:1 µmoles DOTMA) |
| | Plasmid:lipid = 1:3 (1 mg DNA:3 µmoles DOTMA) |
| | Plasmid:lipid = 1:4 (1 mg DNA:4 µmoles DOTMA) |
| | Plasmid:lipid = 1:6 (1 mg DNA:6 µmoles DOTMA) |

Mice were sacrificed 48 hr. post injection. Brains were removed and separated into left and right hemispheres. Each hemisphere was homogenized in 250 µl 0.25 M Tris pH 7.8, 5 mM EDTA followed by three cycles of freeze-thaw then 10 min. at 65° C.

The amounts of extracts used for CAT assay were normalized to protein levels. 0.3 ml of $^{14}$C-chloramphenicol was used for each assay. Assays were carried out at 37° C. overnight. The reaction products were separated on TLC plate and exposed to film, as described in Example 4.

Results: These results demonstrate that high level expression of a heterologous gene can be produced throughout the brain by injection of DNA-liposome complexes (at appropriate ratios) directly into the central nervous system. They also demonstrate that injection of an expression plasmid alone can produce significant transgene expression in the brain. The results are shown in FIG. 20.

Example 23

Demonstration of CAT Gene Expression in the Lung After Intravenous (iv) Injection of pRSV-CAT:L-PE:CEBA Complexes Lipid carrier: L-PE:CEBA=1:1, stock 20 mM in lipid carrier buffer.

Plasmid: pRSV-CAT.

DNA:Lipid carrier Ratio: Lipid carrier:plasmid=1 nanomole cationic lipid: 1 µg plasmid DNA.

DNA dose: 100 µg plasmid DNA in 200 µl 5% dextrose in water was injected by tail vein per mouse.

Mice: Balb/c, female, 25 grams.

Tissue extraction procedure: Forty eight hours after tail vein injection, the animals were sacrificed, whole lung was homogenized in 1 ml of 0.25M Tris-HCl pH 7.8, 5 mM EDTA, 80 µg/ml PMSF and the resulting extract was centrifuged and then the supernatant was subjected to 3 cycles of freeze-thaw and then heated to 65° C. for 20 min.

CAT assay procedure: 100 µl of extract+10 µl of 20 mM acetyl CoA+4 µl of $^{14}$C-chloramphenicol (25 µCi/ml, 55 mCi/mmole, Amersham) were incubated together at 37° C. for 6 hr. At 3 hours, an additional 10 µl of acetyl CoA was added.

Results:

This experiment showed that a significant level of CAT activity (indicative of expression of the transgene) was present in the lung of the animal injected with lipid carrier:DNA complexes, but not present in the lungs from control animals.

Example 24

Demonstration of CAT Gene Expression in Multiple Tissues After Intravenous (iv Injection of pZN20-CAT:DDAB:DOPE Complexes Lipid carrier: DDAB:DOPE=1:1, stock 10 mM in 5% dextrose.

Plasmid: pZN20.

DNA:Lipid carrier Ratio: Lipid carrier:plasmid=(A) 3 nmole cationic lipid:

1 µg plasmid DNA (SUV). (B) 6 nmole cationic lipid: 1 µg plasmid DNA (MLV).

DNA dose: 100 µg plasmid DNA in 200 µl 5% dextrose in water was injected by tail vein per mouse. Three mice each received this dose of MLV:pZN20 and 3 mice each this dose of SUV:pZN20.

Tissue extraction procedure: Each organ was homogenized in 0.3 ml of 0.25 M Tris-HCl pH 7.8, 5 mM EDTA, and the resulting extract was centrifuged and then the supernatant was subjected to 3 cycles of freeze-thaw and then heated to 65° C. for 20 min.

CAT assay procedure: The protein concentration of each tissue extract was quantitated using a Coomassie Blue-based protein assay (BioRad, Richmond, Calif.), and the same amount of total protein from each tissue extract was added in the CAT assay, together with 10 µl of 20 mM acetyl CoA+12 µl of $^{14}$C-chloramphenicol (25 µCi/ml, 55 mCi/mmole, Amersham), at 37° C. for 13 hrs.

Results:

This experiment demonstrated that iv injection of pZN20:DDAB:DOPE complexes gave significant levels of CAT gene expression in each of 6 different tissues including lung, heart, liver, spleen, kidney and lymph nodes. Furthermore, MLV lipid carriers mediated equal or higher levels of in vivo transgene expression than did SUV lipid carriers composed of the same lipids.

Example 25

Production of Vaccines

The subject invention may find general utility in the production of vaccine, in vivo, for a variety of diseases. It has been shown that chimeric, genetically-engineered proteins of antigen fragments linked to granulocyte-macrophage colony-stimulating factor (GM-CSF), augment antigen presentation and increase immune response to the antigen when injected in vivo (Tao and Levy, (1993) *Nature* 362:755–758. Thus a nucleic acid sequence coding for a particular antigen may be fused to the nucleic acid coding for GM-CSF and expressed in appropriate cells in vivo using this invention. This approach could dramatically improve the control of proliferation of malignant cells in the treatment of cancer. Other uses would include in vivo vaccine production against a variety of viral and other infectious diseases, particularly those diseases in which an immune response has been unsuccessful or weak by conventional vaccine strategies. of particular interest would be those diseases, such as HIV, which are characterized by proteins with hypervariable domains. Nucleic acid sequences encoding a variety of possible hypervariable domain sequences could be fused to GM-CSF and expressed simultaneously in vivo to elicit an immune response against many different strains of the virus.

Example 26

Treatment of Tumor Proliferation

Nucleic Acid Sequences Such as Those Coding for Protein 53 may be useful in Treating Tumor Proliferation Sequences coding for the tumor suppressor protein p53 may be expressed intracellularly in vivo using appropriate expression vector-lipid complexes. Such complexes can be conveniently targeted to tumor cells by appropriate antibodies or ligands conjugated to the lipid complexes. Initial information regarding transfection of cells is developed using cultured cells, such as the tumor cell line K562. Once p53 gene expression is verified in K562 cells and the optimal vector have been identified, the following in vivo anti-tumor experiment is conducted. SCID mice receive approximately 25 million K562 cells per mouse by intraperitoneal injection. Approximately three (3) weeks after injection, tumor-bearing mice in groups of ten (10) receive the following: no treatment/control group; p53 vector liposome complexes by intravenous injection; p53 vector liposome complexes by intraperitoneal injection; reported gene vector liposome complexes. The anti-tumor effects of the expression of p53 is then be assessed based upon survival of the mice.

Example 27

Erythropoiesis, the production of red blood cells, can cause continuously throughout the life span to offset cell destruction. Erythropoiesis is a very precisely controlled physiological mechanism and having sufficient numbers of red blood cells to be available in the blood for proper tissue oxygenation, but not so many that the cells would impede circulation. The formation of red blood cells occurs in the bone marrow and is under the control of the hormone erythropoietin. Because of erythropoietin is essential in the process of red blood cells formation, the hormone has potential use for application in both the diagnosis of the treatment of blood disorders characterized by low or defective red blood cell production. Gene therapy using the coding sequence for erythropoietin does find use in a variety of disease states, disorders and states of hematologic irregularity including anemia, in particularly correction of anamia of a type associated with chronic renal failure and the like. A nucleic acid sequence coding for a polypeptide having EPO activity is inserted into an appropriate transcription or expression cassette and introduced into a host mammal as naked DNA or complexed with an appropriate liquid carrier. Monitoring of the production of active EPO polypeptide can be performed as, described for example in U.S. Pat. No. 4,703,008.

As shown by the above results, a plurality of tissues can be transformed following systemic administration of transgenes, either complexed to a lipid carrier or as naked nucleic acid. Expression of exogenous DNA following intravenous injection of a cationic lipid carrier/exogenous DNA complex into a mammalian host has been shown in multiple tissues, including T lymphocytes, metastatic tumors and intravascular tumor emboli. Expression of exogenous DNA in multiple different tissues, including those of the reticuloendothelial system has been obtained following intravenous injection of an expression plasmid as naked DNA. The ability to transfect T lymphocytes in vivo will have a dramatic impact on the treatment of AIDS, cancer, multiple sclerosis, and arthritis. In vivo transfection of cardiac endothelial cells will have a dramatic impact on the treatment of heart disease and heart attacks. In vivo transfection of lung cells will have a dramatic impact on the treatment of cystic fibrosis, asthma, emphysema and lung cancer. In vivo transfection of bone marrow cells will have a dramatic impact on the treatment of cancer, blood diseases and infections.

The in vivo gene therapy delivery technology as described above is non-toxic in animals and transgene expression has been shown to last for at least 60 days after a single administration. The transgene does not appear to integrate into host cell DNA at detectable levels in vivo as measured by Southern analysis, suggesting that this technique for gene therapy will not cause problems for the host mammal by altering the expression of normal cellular genes activating cancer-causing oncogenes, or turning off cancer-preventing tumor suppressor genes. Additionally, transgene expression after systemic administration of a DNA expression vector alone has been shown; transgene expression was produced in the lung for at least three weeks after a single administration of a DNA expression vector without a carrier system.

Systematic injection of heterologous genes into adult animals can produce very high level transgene expression in a wide range of tissues, and transfect the majority (>70%) of all cells present in many of these tissues as demonstrated above. In contrast, previous studies attempting direct transfer of heterologous genes into adult animals have reported transfection limited to one or a few tissues, low levels of transgene expression in these tissues and (whenever histochemical analysis was included) transfection limited to less than 1% of the cells present in transfected tissues.

In addition to transfecting the majority of all cells present in the lung, using the methods and constructs described above, high level transgene expression has been obtained in a wide variety of other tissues and cell types. These include:

Transfection of the majority of all cells present in the spleen and lymph nodes, including transfection of greater than 70% of all the T lymphocytes. The ability to efficiently transfect T lymphocytes in vivo permitting for the first time specific molecular approaches to both anti-HIV therapy and to selective modulation of the immune response.

Efficient transfection of visceral tumors and of intravascular tumor emboli after iv injection of DNA into tumor-bearing hosts. Previously, gene transfer studies involving cancer have been restricted solely to ex vivo approaches. Our work now permits direct transfection with transgenes which provide tumor suppressor, anti-oncogene and/or anti-metastases activity within tumors in tumor-bearing hosts.

Transfection of the majority of cardiac vascular endothelial cells, as well as bone marrow-derived hematopoietic cells, including the great majority of blast cells present in the bone marrow, by systemic delivery of heterologous genes. These results create dramatic and new means for controlling ischemic heart disease and hematopoiesis at the molecular level.

Demonstration of the ability to produce high level in vivo expression of a variety of biologically important transgenes, as exemplified by human CFTR, IL-2 and GM-CSF.

All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of introducing a nucleic acid into cells of a mammal, said method comprising introducing the nucleic acid into the mammal systemically, wherein:

the nucleic acid is complexed to a lipid carrier comprising cationic lipids and a steroid, the carrier having a mean diameter of less than about 10 microns, resulting in a nucleic acid-lipid carrier complex;

the nucleic acid-lipid carrier complexes are substantially free of macroaggregates prior to said systemic introduction;

the nucleic acid to lipid carrier ratio is less than 6:1 micrograms nucleic acid to nanomoles cationic lipid; and the nucleic acid comprises a DNA expression cassette comprising a promoter and a DNA subsequence encoding a protein.

2. The method of claim 1, wherein the steroid is cholesterol.

3. The method of claim 1, wherein the nucleic acid:cationic lipid carrier ratio is about 1:6 μg nucleic acid:nmoles cationic lipid and the lipid carrier comprises DOTAP and cholesterol.

4. A method of introducing a nucleic acid into a mammal, said method comprising introducing the nucleic acid into the mammal systemically, wherein:
the nucleic acid is complexed to a lipid carrier consisting essentially of cationic lipids and steroids, said carrier having a mean diameter of less than about 10 microns, wherein the molar ratio of cationic lipids to steroids ranges from about 1:19 to about 1:1, resulting in a nucleic acid lipid carrier complex;
the nucleic acid-lipid carrier complexes are administered in a form substantially free of macroaggregates;
the nucleic acid to lipid carrier ratio is less than 6:1 micrograms nucleic acid to nanomoles cationic lipid; and the nucleic acid comprises a DNA expression cassette comprising a promoter and a DNA subsequence encoding a protein.

5. The method of claim 4, wherein the non-cationic lipid is a steroid.

6. The method of claim 4, wherein the molar ratio of cationic lipids to steroids is about 1:1.

7. The method of claim 1, or 4, whereby the nucleic acid is introduced into cells of at least two tissues in the mammal.

8. The method of claim 1, or 4, whereby the nucleic acid is introduced into cells of at least two tissues in the mammal and expressed in said at least two tissues.

9. The method of claim 1, or 4, wherein the lipid carrier is an MLV.

10. The method of claim 1, or 4, wherein the lipid carrier is an MLV with a mean diameter of at least about 500 nm.

11. The method of claim 1, or 4, wherein the lipid carrier is an SUV.

12. The method of claim 1, wherein the lipid carrier comprises DOPE.

13. The method of claim 1, or 4, wherein the promoter is an HCMV promoter.

14. The method of claim 1, or 4, wherein the nucleic acid is a DNA plasmid.

15. The method of claim 1, or 4, wherein the nucleic acid:lipid carrier does not aggregate in an aqueous solution comprising 5% dextrose.

16. The method of claim 1, or 4, wherein the nucleic acid does not comprise an intron.

17. The method of claim 1, or 4, wherein the nucleic acid is a DNA expression cassette comprising a 5' intron.

18. The method of claim 1, or 4, wherein at least about 50 μg of the nucleic acid is introduced into the mammal.

19. The method of claim 1, or 4, wherein the nucleic acid is a DNA purified without PEG prior to complexing to said lipid carrier.

20. The method of claim 1, or 4, wherein the size of the nucleic acid:lipid carrier complex is at least about 500 nm.

21. The method of claim 1, or 4, wherein the nucleic acid is linear.

22. The method of claim 1, or 4, wherein the nucleic acid is introduced into said mammal intravenously.

23. The method of claim 1, or 4, wherein the nucleic acid is introduced into said mammal intraperitoneally.

24. The method of claim 23, wherein the lipid carrier comprises cholesterol.

25. The method of claim 1, or 4, wherein the nucleic acid:cationic lipid carrier ratio is between about 1:1 and about 1:6 μg nucleic acid:nmoles cationic lipid.

26. The method of claim 1, or 4, wherein the nucleic acid:cationic lipid carrier ratio is about 1:1 to about 1:5 μg nucleic acid:nmoles cationic lipid and the cationic lipid carrier comprises DDAB.

27. The method of claim 1, or 4, wherein the nucleic acid:cationic lipid carrier ratio is about 1:1 μg nucleic acid:nmoles cationic lipid and the lipid carrier comprises LPE and CEBA.

28. The method of claim 1, or 4, wherein the nucleic acid:cationic lipid carrier ratio is about 1:5 μg nucleic acid: nmoles cationic lipid and the lipid carrier comprises DDAB and cholesterol.

29. The method of claim 1, or 4, wherein a cell into which nucleic acid is introduced is selected from the group consisting of a mammalian T cell, a lung cell, a liver cell, a vascular endothelial cell, and a cell of lymph node.

30. The method of claim 1, or 4, wherein said lipid carriers have a mean diameter ranging in size from about 100 nm to 10 μm.

31. The method of claim 1, or 4, wherein the cationic lipid comprises a lipid other than DOTMA.

32. The method of claim 1, or 4, wherein said lipid carriers do not comprise DOTMA.

33. The method of claim 1, or 4, wherein the DNA expression cassette to lipid carrier ratio is greater than 1:3 micrograms DNA to nanomoles cationic lipid.

34. A mammalian transformation complex comprising:
a cationic lipid and a non-cationic lipid forming a lipid complex ranging in size from 100 nm to 10 microns in diameter; combined with nucleic acid in a ratio of less than 6:1 micrograms nucleic acid to nanomoles cationic lipid;
an excipient for in vivo systemic administration; and,
wherein said non-cationic lipid comprises cholesterol and said complex is substantially free of macroaggregates in vitro, the complex transforms a cell in vivo following systemic administration, and wherein the nucleic acid comprises a DNA expression cassette comprising a promoter and a DNA subsequence encoding a protein.

35. The mammalian transformation complex of claim 34, wherein the nucleic acid is DNA.

36. A method of making a nucleic acid:lipid complex for systemic administration to a mammal comprising:
mixing a nucleic acid and a lipid carrier to provide a non-aggregating nucleic acid:lipid carrier complex having a mean diameter of less than about 10 microns, wherein the lipid carrier comprises cationic lipids and a steroid, the nucleic acid to lipid carrier ratio is less than 6:1 micrograms DNA to nanomoles cationic lipid, and wherein the nucleic acid comprises a DNA expression cassette comprising a promoter and a DNA subsequence encoding a protein; and,
diluting the complex with a pharmaceutically acceptable excipient.

37. The method of claim 36, wherein the steroid is cholesterol.

38. The method of claim 36, wherein the nucleic acid:cationic lipid carrier ratio is about 1:6 μg nucleic acid:nmoles cationic lipid and the lipid carrier comprises DOTAP and cholesterol.

* * * * *